United States Patent
Shinohara et al.

(10) Patent No.: US 10,378,011 B2
(45) Date of Patent: Aug. 13, 2019

(54) OLIGONUCLEOTIDE

(71) Applicant: Kyowa Hakko Kirin Co., Ltd., Tokyo (JP)

(72) Inventors: Fumikazu Shinohara, Tokyo (JP); Asana Makino, Tokyo (JP); Junichiro Yamamoto, Tokyo (JP); Taiji Oashi, Tokyo (JP); Michihiko Suzuki, Tokyo (JP); Jun-ichi Saito, Tokyo (JP); Takahiro Nakajima, Tokyo (JP); Tomoyuki Nishikawa, Tokyo (JP); Masayoshi Nakoji, Tokyo (JP); Yuichi Takahashi, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 0 days.

(21) Appl. No.: 14/423,749

(22) PCT Filed: Sep. 2, 2013

(86) PCT No.: PCT/JP2013/073569
§ 371 (c)(1),
(2) Date: Feb. 25, 2015

(87) PCT Pub. No.: WO2014/034934
PCT Pub. Date: Mar. 6, 2014

(65) Prior Publication Data
US 2015/0376611 A1 Dec. 31, 2015

Related U.S. Application Data

(60) Provisional application No. 61/695,566, filed on Aug. 31, 2012.

(30) Foreign Application Priority Data

May 20, 2013 (JP) .................................. 2013-105947

(51) Int. Cl.
*C07H 21/04* (2006.01)
*C12N 15/11* (2006.01)
(Continued)

(52) U.S. Cl.
CPC .......... *C12N 15/113* (2013.01); *A61K 31/713* (2013.01); *C07H 21/02* (2013.01);
(Continued)

(58) Field of Classification Search
CPC .... A61K 31/713; C07H 21/02; C12N 15/113; C12N 15/111; C12N 2330/30;
(Continued)

(56) References Cited

U.S. PATENT DOCUMENTS 5,457,187 A * 10/1995 Gmeiner ................ C07H 21/00 536/25.5
5,530,110 A * 6/1996 Sowers ................ C07H 19/056 536/28.54
(Continued)

FOREIGN PATENT DOCUMENTS

JP 53-63399 6/1978
JP 59-156297 9/1984
(Continued)

OTHER PUBLICATIONS

Herdewijn, "Heterocyclic Modifications of Oligonucleotides and Antisense Technology", Antisense & Nucleic Acid Drug Development, 2000, vol. 10, pp. 297-310.
(Continued)

*Primary Examiner* — Lawrence E Crane
(74) *Attorney, Agent, or Firm* — Wenderoth, Lind & Ponack, L.L.P.

(57) ABSTRACT

An oligonucleotide having improved affinity for AGO2 is disclosed. The oligonucleotide has a nucleotide residue or a nucleoside residue represented by formula (I) wherein $X^1$ is an oxygen atom or the like, $R^1$ is formula (IIA), wherein $R^{5A}$ is halogen or the like, and $R^{6A}$ is a hydrogen atom or the like, or formula (IVA) wherein $Y^{3A}$ is a nitrogen atom or the like, and $Y^{4A}$ is CH or the like, or the like, $R^2$ is a hydrogen atom, hydroxy, halogen, or optionally substituted lower alkoxy, and $R^3$ is a hydrogen atom or the like at the 5' end thereof, and the nucleotide residue or the nucleoside residue binds to an adjacent nucleotide residue through the oxygen atom at position 3. A method for improving the knockdown activity of an oligonucleotide wherein the oligonucleotide has a knockdown activity against an mRNA encoding a protein involved in a disease.

(I)

(IIA)

(Continued)

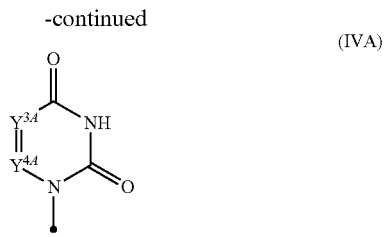

(IVA)

10 Claims, 3 Drawing Sheets

Specification includes a Sequence Listing.

(51) Int. Cl.
C12N 15/113 (2010.01)
A61K 31/713 (2006.01)
C07H 21/02 (2006.01)

(52) U.S. Cl.
CPC ........ C12N 15/111 (2013.01); C12N 2310/14 (2013.01); C12N 2310/32 (2013.01); C12N 2310/33 (2013.01); C12N 2320/50 (2013.01); C12N 2320/51 (2013.01); C12N 2330/30 (2013.01)

(58) Field of Classification Search
CPC ............ C12N 2310/33; C12N 2310/32; C12N 2310/14; C12N 2320/50; C12N 2320/51
See application file for complete search history.

(56) References Cited

U.S. PATENT DOCUMENTS

| | | | | | |
|---|---|---|---|---|---|
| 5,614,505 | A | * | 3/1997 | Gmeiner | C07H 21/00 514/50 |
| 5,663,321 | A | * | 9/1997 | Gmeiner | C07H 21/00 424/152.1 |
| 5,663,323 | A | * | 9/1997 | Sowers | C07H 19/056 536/25.3 |
| 5,741,900 | A | * | 4/1998 | Gmeiner | C07H 21/00 536/25.3 |
| 5,906,918 | A | | 5/1999 | Box et al. | |
| 8,518,908 | B2 | * | 8/2013 | Hrdlicka | C07H 19/06 514/43 |
| 8,912,318 | B2 | * | 12/2014 | Hrdlicka | C07H 19/06 536/27.1 |
| 9,056,886 | B2 | * | 6/2015 | Lee | C07H 21/00 |
| 9,506,886 | B1 | * | 11/2016 | Woodbury | A61F 13/42 |
| 2011/0087015 | A1 | | 4/2011 | Hirano et al. | |
| 2013/0102652 | A1 | | 4/2013 | Burrows et al. | |
| 2014/0330004 | A1 | | 11/2014 | Shinohara et al. | |
| 2014/0343129 | A1 | | 11/2014 | de Fougerolles et al. | |
| 2015/0376611 | A1 | | 12/2015 | Shinohara et al. | |
| 2016/0256573 | A1 | | 9/2016 | de Fougerolles et al. | |

FOREIGN PATENT DOCUMENTS

| | | |
|---|---|---|
| WO | 95/21184 | 8/1995 |
| WO | 03/004603 | 1/2003 |
| WO | 2006/112872 | 10/2006 |
| WO | 2011/119674 | 9/2011 |
| WO | 2013/090186 | 6/2013 |
| WO | 2014/034934 | 3/2014 |

OTHER PUBLICATIONS

Chiu et al., "siRNA function in RNAi: A chemical modification analysis", RNA, 2003, vol. 9. No. 9, pp. 1034-1048.

Terrazas et al., "RNA major groove modifications improve siRNA stability and biological activity", Nucleic Acids Research, 2009, vol. 37, No. 2, pp. 346-353.

Addepalli et al., "Modulation of thermal stability can enhance the potency of siRNA", Nucleic Acids Research, 2010, vol. 38, No. 20, pp. 7320-7331.

Peacock et al.. "$N^2$-Modified 2-aminopurine ribonucleosides as minor-groove-modulating adenosine replacements in duplex RNA", Organic Letters, 2010, vol. 12, No. 5, pp. 1044-1047.

Peacock et al., "Minor-Groove-Modulating Adenosine Replacements Control Protein Binding and RNAi Activity in siRNAs", ACS Chemical Biology, 2010, vol. 5, No. 12, pp. 1115-1124.

Mikat et al., "Light-dependent RNA interference with nucleobase-caged siRNAs", RNA, 2007, vol. 13, No. 12, 2341-2347.

Eberle et al., "Modifications in Small Interfering RNA That Separate Immunostimulation from RNA Interference", Journal of Immunology, 2008, vol. 180, pp. 3229-3237.

Hernandez et al., "Steric Restrictions of RISC in RNA Interference Identified with Size-Expanded RNA Nucleobases", ACS Chemical Biology, 2012, vol. 7, No. 8, pp. 1454-1461.

Ibarra-Soza et al., "7-Substitutent 8-aza-7-deazaadenosines for modification of the siRNA major groove", Org. Biomol. Chem., 2012, vol. 10, No. 32, pp. 6491-6497.

Xia et al., "Gene Silencing Activity of siRNAs with a Ribo-difluorotoluyl Nucleotide", ACS Chemical Biology, vol. 1, No. 3, pp. 176-183.

Sanghvi et al., "Antisense oligodeoxynucleotides: synthesis, biophysical and biological evaluation of oligodeoxynucleotides containing modified pyrimidines", Nucleic Acids Research, 1993, vol. 21, No. 14, pp. 3197-3203.

Freier et al., "The ups and downs of nucleic acid duplex stability: structure-stability studies on chemically-modified DNA:RNA duplexes", Nucleic Acids Research, 1997, vol. 25, No. 22, pp. 4429-4443.

Froehler et al., "Oligodeoxynucleotides Containing C-5 Propyne Analogs of 2'-Deoxyuridine and 2'-Deoxcycytidine", Tetrahedron Letters, 1992, vol. 33, No. 37, pp. 5307-5310.

Wagner et al., "Antisense Gene Inhibition by Oligonucleotides Containing C-5 Propyne Pyrimidines", Science, 1993, vol. 260, pp. 1510-1513.

Moulds et al., "Site and Mechanism of Antisense Inhibition by C-5 Propyne Oligonucleotides", Biochemistry, 1995, vol. 34, pp. 5044-5053.

Stuart et al., "Structure of the Trinucleotide D-acp$^3$U-A with Coordinated Mg$^{2+}$ Demonstrates that Modified Nucleosides Contribute to Regional Conformations of RNA", Nucleosides and Nucleotides, 1996, vol. 15, No. 5, pp. 1009-1028.

International Search Report dated Dec. 3, 2013 in International (PCT) Application No. PCT/JP2013/073569.

D. M. Kenski et al., "SiRNA-Optimized Modifications for Enhanced In Vivo Activity", Molecular Therapy—Nucleic Acids, vol. 1, pp. 1-8, 2012.

S. M. Elbashir et al., "Duplexes of 21-Nucleotide RNAs Mediate RNA Interference in Cultured Mammalian Cells", Nature, vol. 411, pp. 494-498, May 24, 2001.

C. V. Pecot et al., "RNA Interference in the Clinic: Challenges and Future Directions", Nature Reviews, vol. 11, pp. 59-67, Jan. 2011.

T. Kawamata et al., "Making RISC", Trends in Biochemical Sciences, vol. 35, No. 7, pp. 368-376, 2010.

J. S. Parker, "How to Slice: Snapshots of Argonaute in Action", Silence, vol. 1, No. 3, pp. 1-10, 2010.

N. T. Schirle et al., "The Crystal Structure of Human Argonaute2", Science, vol. 336, pp. 1037-1040, May 25, 2012.

R. Vijayakrishnan, "Structure-Based Drug Design and Modern Medicine", Journal of Postgraduate Medicine, vol. 55, Issue 4, pp. 301-304, 2009.

J. Liu et al., "Synthesis of Photoactive DNA: Incorporation of 8-Bromo-2'-Deoxyadenosine into Synthetic Oligodeoxynucleotides", Tetrahedron Letters, vol. 33, No. 30, pp. 4265-4268, 1992.

S. Shibutani et al., "Translesional Synthesis on DNA Templates Containing 8-Oxo-7,8-Dihydrodeoxyadenosine", Biochemistry, vol. 32, No. 17, pp. 4615-4621, 1993.

(56) References Cited

OTHER PUBLICATIONS

J. Beres et al., "Synthesis, Structure, and Antitumor and Antiviral Activities of a Series of 5-Halouridine Cyclic 3',5'-Monophosphates", J. Med. Chem., vol. 29, No. 4, pp. 488-493, 1986.

J. Michel et al., "Triplex Stability of Oligodeoxynucleotides Containing Substituted Quinazoline-2,4-(1H,3H)-Dione", Tetrahedron, vol. 53, No. 25, pp. 8457-8478, 1997.

Y. Tor et al., "Designing New Isomorphic Fluorescent Nucleobase Analogues", the Thieno[3,2-d]Pyrimidine Core, Tetrahedron, vol. 63, No. 17, pp. 3608-3614, 2007.

H. Seitz et al., "A 5'-Uridine Amplifies miRNA/miRNA* Asymmetry in *Drosophila* by promoting RNA-Induced Silencing Complex Formation", Silence, vol. 2, No. 4, pp. 1-10, 2011.

F. Frank et al., "Structural Basis for 5'-Nucleotide Base-Specific Recognition of Guide RNA by Human AGO2", Nature, vol. 465, pp. 818-822, Jun. 10, 2010.

H. Peacock et al., "Chemical Modification of siRNA Bases to Probe and Enhance RNA Interference", The Journal of Organic Chemistry, vol. 76, No. 18, pp. 7295-7300, 2011.

G. F. Deleavey et al., "Designing Chemically Modified Oligonucleotides for Targeted Gene Silencing", Chemistry & Biology, vol. 19, No. 8, pp. 937-954, Aug. 24, 2012.

W. F. Lima et al., "Binding and Cleavage Specificities of Human Argonaute2", The Journal of Biological Chemistry, vol. 284, No. 38, pp. 26017-26028, Sep. 18, 2009.

Watts et al., "Chemically modified siRNA: tools and applications", Drug Discovery Today, 2008, vol. 13, Nos. 19/20, pp. 842-855.

Holmes et al., "Synthesis and Oligonucleotide Incorporation of Nucleotide Analogues Containing Pendant Imidazolyl or Amino Functionalities—The Search for Sequence-Specific Artificial Ribonucleases", European Journal of Organic Chemistry, 2005, vol. 2005, No. 24, pp. 5171-5183.

Haouz et al., "Enzymatic and Structural Analysis of Inhibitors Designed against *Mycobacterium tuberculosis* Thymidylate Kinase", The Journal of Biological Chemistry, 2002, vol. 278, No. 7, pp. 4963-4971.

Rodrigues-Correia et al., "Comparison of the duplex-destabilizing effects of nucleobase-caged oligonucleotides", Analytical and Bioanalytical Chemistry, 2010, vol. 399, No. 1, pp. 441-447.

Partial European Search Report dated Jul. 3, 2017 issued in European counterpart Application No. EP15 758 130.7.

Yoshihiro Iijima et al., "Modified oligodeoxynucleotide primers for reverse-transcription of target RNAs that can discriminate among length variants at the 31'-terminus", Organic & Biomolecular Chemistry, vol. 11, No. 47, Oct. 2, 2013, pp. 8276-8272.

Christopher L. Millington, et al., "Convenient and Efficient Syntheses of Oligodeoxyribonucleotides Containing O6-(Carboxymethyl)Guanine and O6-(4-Oxo-4-(3-Pyridyl)Butyl)Guanine", Nucleosides, Nucleotides and Nucleic Acids, vol. 31, No. 4, Apr. 1, 2012, pp. 328-338.

LászlóÖtvös, et al., "Synthesis and Enzymatic Characterization of P1-THIO-P2-OXO Trideoxynucleoside Diphosphates Having AZT, FdU, or dT At the 3'-Position", Nucleosides, Nucleotides and Nucleic Acid, vol. 21. No. 1, 2002, pp. 79-82.

Kazumitsu Onizuka et al., "Short Interfering RNA Guide Strand Modifiers from Computational Screening", The Journal of the American Chemical Society, vol. 135, 2013, pp. 17069-17077.

International Search Report dated May 12, 2015 in corresponding International Application No. PCT/JP2015/056249.

* cited by examiner

[FIG. 1]
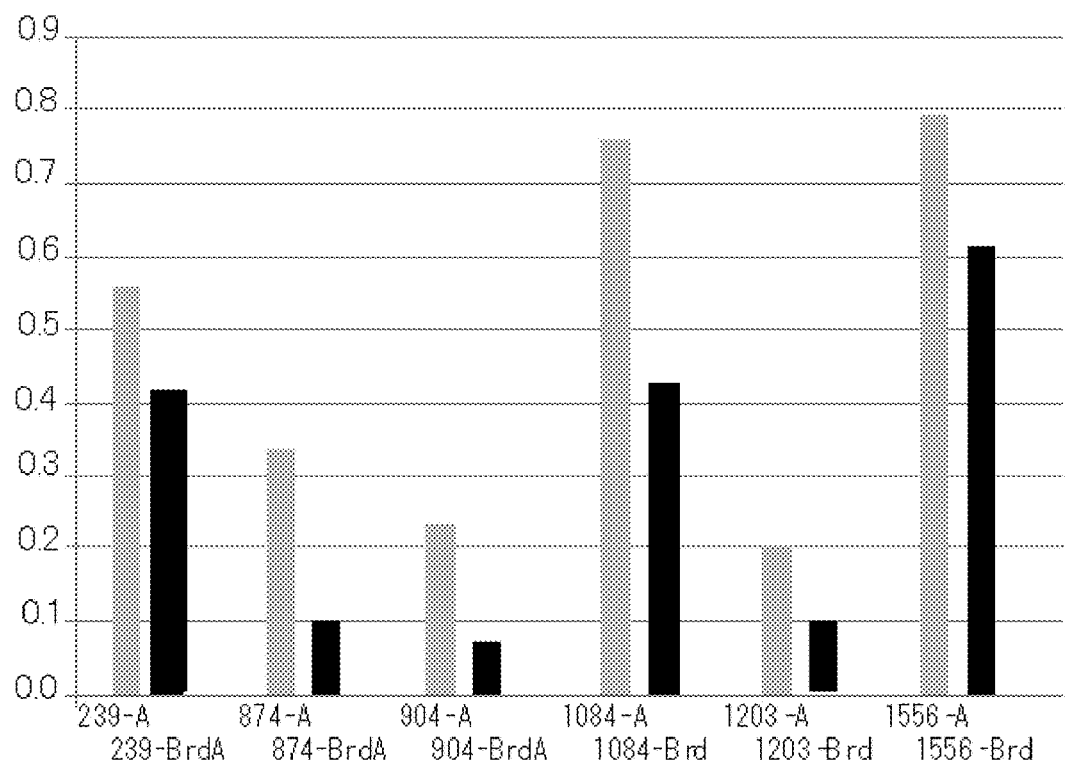

[FIG. 2]
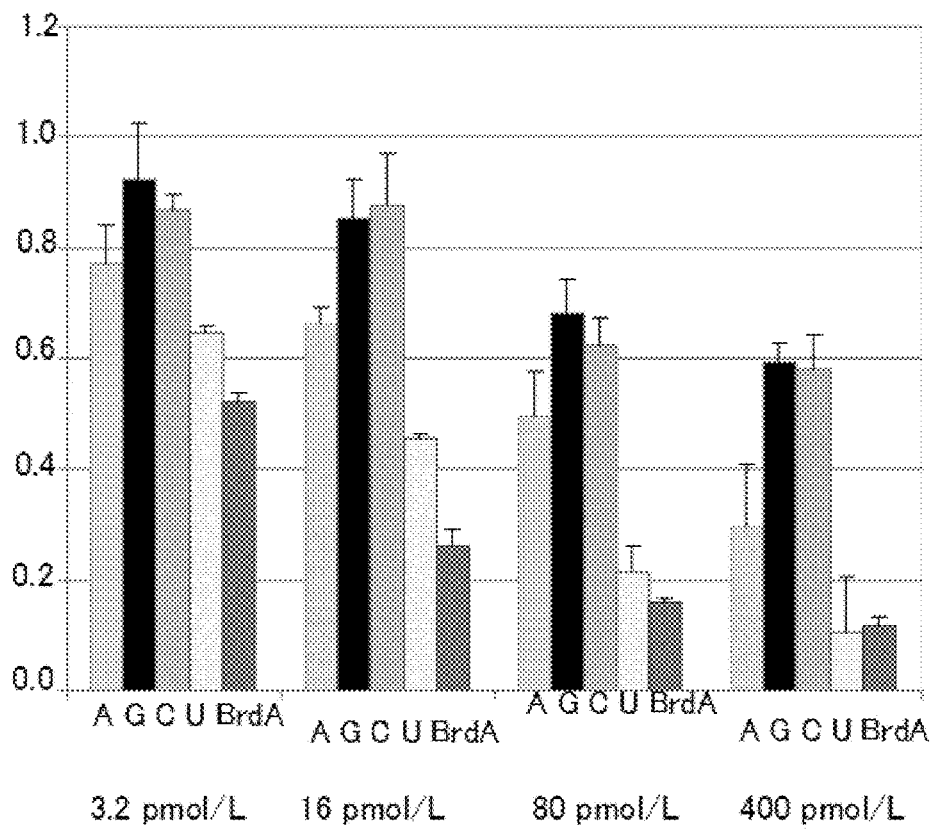
[FIG. 3]
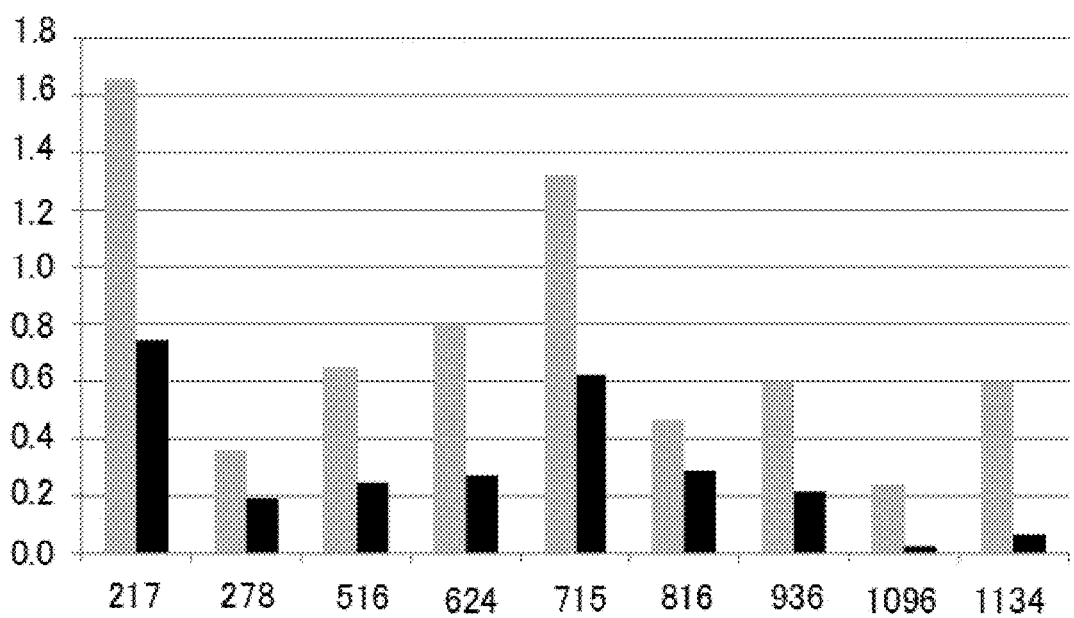

[FIG. 4]
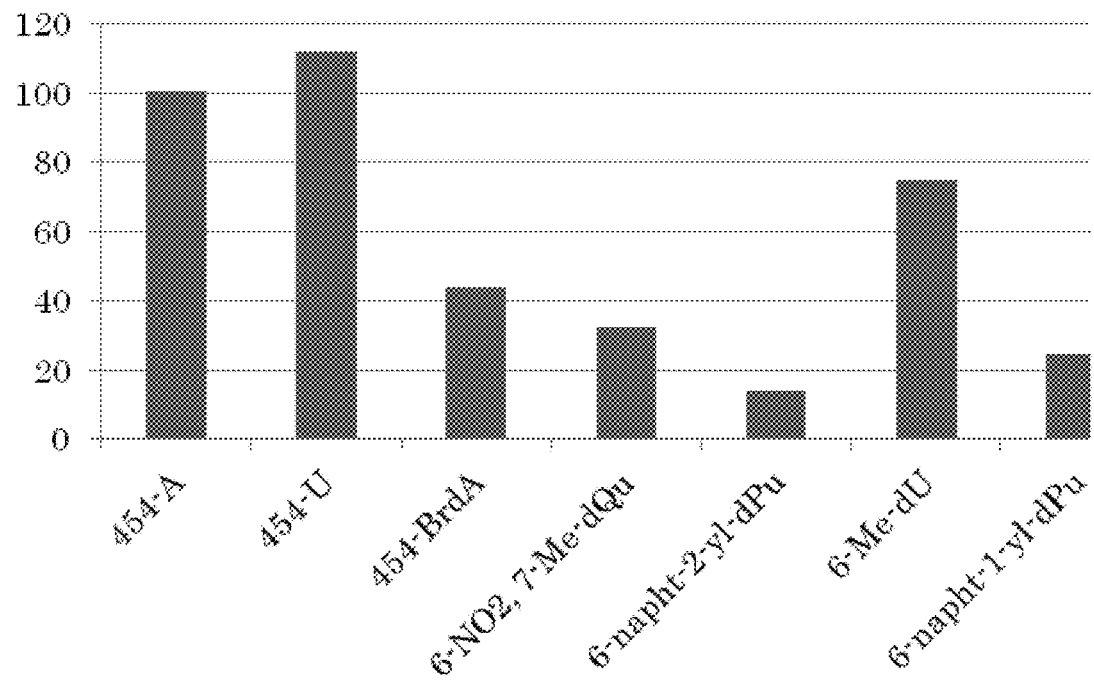
[FIG. 5]
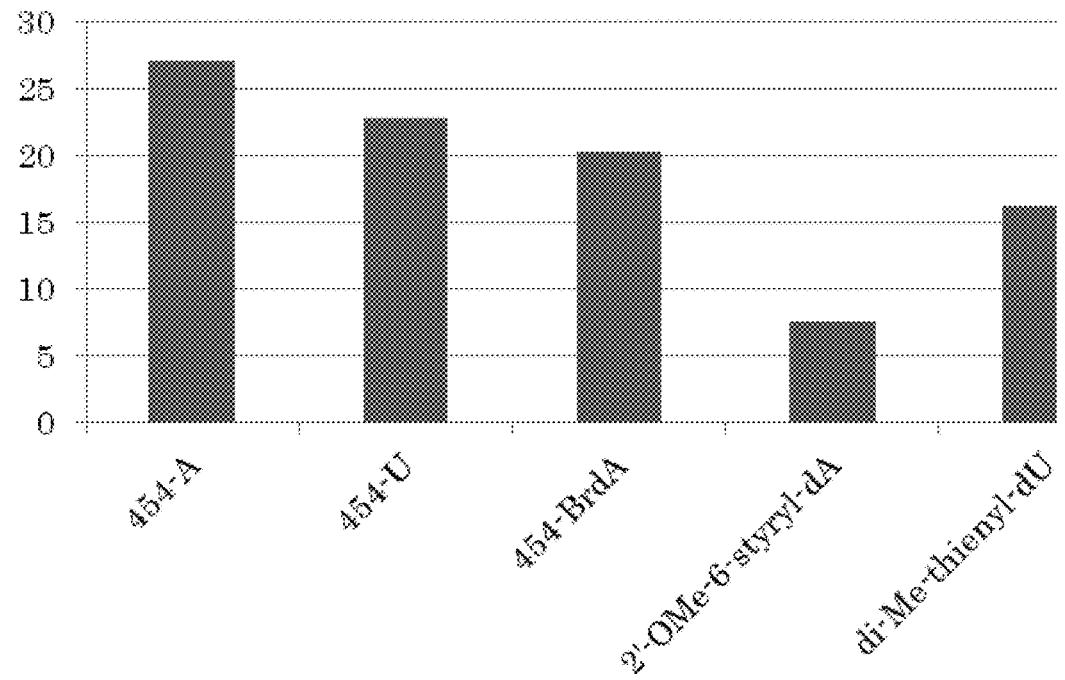

SEQUENCE LISTING

<160> NUMBER OF SEQ ID NOS: 66

<210> SEQ ID NO 1

```
<211> LENGTH: 21
<212> TYPE: RNA
<213> ORGANISM: Artificial Sequence
<220> FEATURE:
<223> OTHER INFORMATION: 239-BrdA sense

<400> SEQUENCE: 1
ugcagcgaga auagcuugua g                                              21

<210> SEQ ID NO 2
<211> LENGTH: 21
<212> TYPE: RNA
<213> ORGANISM: Artificial Sequence
<220> FEATURE:
<223> OTHER INFORMATION: 239-BrdA antisense
<220> FEATURE:
<221> NAME/KEY: misc_feature
<222> LOCATION: (1)..(1)
<223> OTHER INFORMATION: n = 8-bromo-2'-deoxyadenosine monophosphate

<400> SEQUENCE: 2
ncaagcuauu cucgcugcac a                                              21

<210> SEQ ID NO 3
<211> LENGTH: 21
<212> TYPE: RNA
<213> ORGANISM: Artificial Sequence
<220> FEATURE:
<223> OTHER INFORMATION: 874-BrdA sense

<400> SEQUENCE: 3
uagcuucuuc gcuaagagua c                                              21

<210> SEQ ID NO 4
<211> LENGTH: 21
<212> TYPE: RNA
<213> ORGANISM: Artificial Sequence
<220> FEATURE:
<223> OTHER INFORMATION: 874-BrdA antisense
<220> FEATURE:
<221> NAME/KEY: misc_feature
<222> LOCATION: (1)..(1)
<223> OTHER INFORMATION: n = 8-bromo-2'-deoxyadenosine monophosphate,
      8-oxo-2'-deoxyadenosine monophosphate, or 5-bromo-2'-deoxyuridine

<400> SEQUENCE: 4
ncucuuagcg aagaagcuaa a                                              21

<210> SEQ ID NO 5
<211> LENGTH: 21
<212> TYPE: RNA
<213> ORGANISM: Artificial Sequence
<220> FEATURE:
<223> OTHER INFORMATION: 904-BrdA sense

<400> SEQUENCE: 5
caaguacgac cuaagcaauu u                                              21

<210> SEQ ID NO 6
<211> LENGTH: 21
<212> TYPE: RNA
<213> ORGANISM: Artificial Sequence
<220> FEATURE:
<223> OTHER INFORMATION: 904-BrdA antisense
<220> FEATURE:
<221> NAME/KEY: misc_feature
<222> LOCATION: (1)..(1)
<223> OTHER INFORMATION: n = 8-bromo-2'-deoxyadenosine monophosphate
```

```
<400> SEQUENCE: 6
nuugcuuagg ucguacuugu c                                              21

<210> SEQ ID NO 7
<211> LENGTH: 21
<212> TYPE: RNA
<213> ORGANISM: Artificial Sequence
<220> FEATURE:
<223> OTHER INFORMATION: 1084-BrdA sense

<400> SEQUENCE: 7
aggcaaggug gugcccuuuu u                                              21

<210> SEQ ID NO 8
<211> LENGTH: 21
<212> TYPE: RNA
<213> ORGANISM: Artificial Sequence
<220> FEATURE:
<223> OTHER INFORMATION: 1084-BrdA antisense
<220> FEATURE:
<221> NAME/KEY: misc_feature
<222> LOCATION: (1)..(1)
<223> OTHER INFORMATION: n = 8-bromo-2'-deoxyadenosine monophosphate

<400> SEQUENCE: 8
naagggcacc accuugccua c                                              21

<210> SEQ ID NO 9
<211> LENGTH: 21
<212> TYPE: RNA
<213> ORGANISM: Artificial Sequence
<220> FEATURE:
<223> OTHER INFORMATION: 1203-BrdA sense

<400> SEQUENCE: 9
uuaacaaccc cgaggcuaua a                                              21

<210> SEQ ID NO 10
<211> LENGTH: 21
<212> TYPE: RNA
<213> ORGANISM: Artificial Sequence
<220> FEATURE:
<223> OTHER INFORMATION: 1203-BrdA antisense
<220> FEATURE:
<221> NAME/KEY: misc_feature
<222> LOCATION: (1)..(1)
<223> OTHER INFORMATION: n = 8-bromo-2'-deoxyadenosine monophosphate

<400> SEQUENCE: 10
nuagccucgg gguuguuaac g                                              21

<210> SEQ ID NO 11
<211> LENGTH: 21
<212> TYPE: RNA
<213> ORGANISM: Artificial Sequence
<220> FEATURE:
<223> OTHER INFORMATION: 1556-BrdA sense

<400> SEQUENCE: 11
gacgaggugc cuaaaggauu g                                              21

<210> SEQ ID NO 12
<211> LENGTH: 21
<212> TYPE: RNA
<213> ORGANISM: Artificial Sequence
<220> FEATURE:
<223> OTHER INFORMATION: 1556-BrdA antisense
```

```
<220> FEATURE:
<221> NAME/KEY: misc_feature
<222> LOCATION: (1)..(1)
<223> OTHER INFORMATION: n = 8-bromo-2'-deoxyadenosine monophosphate or
      5-fluoro-2'-deoxyuridine monophosphate

<400> SEQUENCE: 12
nuccuuuagg caccucgucc a                                              21

<210> SEQ ID NO 13
<211> LENGTH: 21
<212> TYPE: RNA
<213> ORGANISM: Artificial Sequence
<220> FEATURE:
<223> OTHER INFORMATION: 239-A antisense

<400> SEQUENCE: 13
acaagcuauu cucgcugcac a                                              21

<210> SEQ ID NO 14
<211> LENGTH: 21
<212> TYPE: RNA
<213> ORGANISM: Artificial Sequence
<220> FEATURE:
<223> OTHER INFORMATION: 874-A antisense

<400> SEQUENCE: 14
acucuuagcg aagaagcuaa a                                              21

<210> SEQ ID NO 15
<211> LENGTH: 21
<212> TYPE: RNA
<213> ORGANISM: Artificial Sequence
<220> FEATURE:
<223> OTHER INFORMATION: 904-A antisense

<400> SEQUENCE: 15
auugcuuagg ucguacuugu c                                              21

<210> SEQ ID NO 16
<211> LENGTH: 21
<212> TYPE: RNA
<213> ORGANISM: Artificial Sequence
<220> FEATURE:
<223> OTHER INFORMATION: 1084-A antisense

<400> SEQUENCE: 16
aaagggcacc accuugccua c                                              21

<210> SEQ ID NO 17
<211> LENGTH: 21
<212> TYPE: RNA
<213> ORGANISM: Artificial Sequence
<220> FEATURE:
<223> OTHER INFORMATION: 1203-A antisense

<400> SEQUENCE: 17
auagccucgg gguuguuaac g                                              21

<210> SEQ ID NO 18
<211> LENGTH: 21
<212> TYPE: RNA
<213> ORGANISM: Artificial Sequence
<220> FEATURE:
<223> OTHER INFORMATION: 1556-A antisense

<400> SEQUENCE: 18
```

```
auccuuuagg caccucgucc a                                              21

<210> SEQ ID NO 19
<211> LENGTH: 21
<212> TYPE: RNA
<213> ORGANISM: Artificial Sequence
<220> FEATURE:
<223> OTHER INFORMATION: 874-G sense

<400> SEQUENCE: 19
uagcuucuuc gcuaagagca c                                              21

<210> SEQ ID NO 20
<211> LENGTH: 21
<212> TYPE: RNA
<213> ORGANISM: Artificial Sequence
<220> FEATURE:
<223> OTHER INFORMATION: 874-G antisense

<400> SEQUENCE: 20
gcucuuagcg aagaagcuaa a                                              21

<210> SEQ ID NO 21
<211> LENGTH: 21
<212> TYPE: RNA
<213> ORGANISM: Artificial Sequence
<220> FEATURE:
<223> OTHER INFORMATION: 874-C sense

<400> SEQUENCE: 21
uagcuucuuc gcuaagagga c                                              21

<210> SEQ ID NO 22
<211> LENGTH: 21
<212> TYPE: RNA
<213> ORGANISM: Artificial Sequence
<220> FEATURE:
<223> OTHER INFORMATION: 874-C antisense

<400> SEQUENCE: 22
ccucuuagcg aagaagcuaa a                                              21

<210> SEQ ID NO 23
<211> LENGTH: 21
<212> TYPE: RNA
<213> ORGANISM: Artificial Sequence
<220> FEATURE:
<223> OTHER INFORMATION: 874-U sense

<400> SEQUENCE: 23
uagcuucuuc gcuaagagaa c                                              21

<210> SEQ ID NO 24
<211> LENGTH: 21
<212> TYPE: RNA
<213> ORGANISM: Artificial Sequence
<220> FEATURE:
<223> OTHER INFORMATION: 874-U antisense

<400> SEQUENCE: 24
ucucuuagcg aagaagcuaa a                                              21

<210> SEQ ID NO 25
<211> LENGTH: 21
<212> TYPE: RNA
```

```
<213> ORGANISM: Artificial Sequence
<220> FEATURE:
<223> OTHER INFORMATION: 454-5-F-dU sense

<400> SEQUENCE: 25
ggauagcaag accgacuaac a                                              21

<210> SEQ ID NO 26
<211> LENGTH: 21
<212> TYPE: RNA
<213> ORGANISM: Artificial Sequence
<220> FEATURE:
<223> OTHER INFORMATION: 454-5-F-dU antisense
<220> FEATURE:
<221> NAME/KEY: misc_feature
<222> LOCATION: (1)..(1)
<223> OTHER INFORMATION: n can be 5-fluoro-2'-deoxyuridine monophosphate
<220> FEATURE:
<221> NAME/KEY: misc_feature
<222> LOCATION: (1)..(1)
<223> OTHER INFORMATION: n can be
      ((2R,3S,4R,5R)-3,4-Dihydroxy-5-(7-(methylamino)-6-nitro-2,4-dioxo-
      3,4-dihydroquinazolin-1(2H)-yl)tetrahydrofuran-2-yl)methyl
      phosphate
<220> FEATURE:
<221> NAME/KEY: misc_feature
<222> LOCATION: (1)..(1)
<223> OTHER INFORMATION: n can be
      ((2R,3S,4R,5R)-3,4-Dihydroxy-5-(6-methyl-2,4-dioxo-3,4-
      dihydropyrimidin-1(2H)-yl)tetrahydrofuran-2-yl)methyl phosphate
<220> FEATURE:
<221> NAME/KEY: misc_feature
<222> LOCATION: (1)..(1)
<223> OTHER INFORMATION: n can be
      ((2R,3S,4R,5R)-3,4-Dihydrozy-5-(6-(naphthalen-2-yl)-9H-purin-9-
      yl)tetrahydrofuran-2-yl)methyl phosphate
<220> FEATURE:
<221> NAME/KEY: misc_feature
<222> LOCATION: (1)..(1)
<223> OTHER INFORMATION: n can be
      (2R,3S,4R,5R)-3,4-Dihydrozy-5-(6-(naphthalen-1-yl)-9H-purin-9-
      yl)tetrahydrofuran-2-yl)methyl phosphate
<220> FEATURE:
<221> NAME/KEY: misc_feature
<222> LOCATION: (1)..(1)
<223> OTHER INFORMATION: n can be
      ((2R,3R,4R,5R)-3-hydroxy-4-methoxy-5-(6-((E)-styryl)-9H-purin-9-
      yl)tetrahydrofuran-2-yl)methyl dihydrogen phosphate
<220> FEATURE:
<221> NAME/KEY: misc_feature
<222> LOCATION: (1)..(1)
<223> OTHER INFORMATION: n can be
      ((2R,3S,4R,5R)-5-(5,6-Dimethyl-2,4-dioxo-3,4-dihydrothieno[2,3-
      d]pyrimidin-1(2H)-yl)-3,4-dihydroxytetrahydrofuran-2-yl)methyl
      phosphate

<400> SEQUENCE: 26
nuagucgguc uugcuaucca u                                              21

<210> SEQ ID NO 27
<211> LENGTH: 21
<212> TYPE: RNA
<213> ORGANISM: Artificial Sequence
<220> FEATURE:
<223> OTHER INFORMATION: 1556-5-F-dU sense

<400> SEQUENCE: 27
gacgaggugc cuaaaggaau g                                              21

<210> SEQ ID NO 28
<211> LENGTH: 21
<212> TYPE: RNA
<213> ORGANISM: Artificial Sequence
```

```
<220> FEATURE:
<223> OTHER INFORMATION: 454-U antisense

<400> SEQUENCE: 28
uuagucgguc uugcuaucca u                                              21

<210> SEQ ID NO 29
<211> LENGTH: 21
<212> TYPE: RNA
<213> ORGANISM: Artificial Sequence
<220> FEATURE:
<223> OTHER INFORMATION: 1556-U antisense

<400> SEQUENCE: 29
uuccuuuagg caccucgucc a                                              21

<210> SEQ ID NO 30
<211> LENGTH: 21
<212> TYPE: RNA
<213> ORGANISM: Artificial Sequence
<220> FEATURE:
<223> OTHER INFORMATION: 217-BrdA sense

<400> SEQUENCE: 30
gcgccugguc accagggcug c                                              21

<210> SEQ ID NO 31
<211> LENGTH: 21
<212> TYPE: RNA
<213> ORGANISM: Artificial Sequence
<220> FEATURE:
<223> OTHER INFORMATION: 217-BrdA antisense
<220> FEATURE:
<221> NAME/KEY: misc_feature
<222> LOCATION: (1)..(1)
<223> OTHER INFORMATION: n = 8-oxo-2'-deoxyadenosine monophosphate

<400> SEQUENCE: 31
ngcccuggug accaggcgcc c                                              21

<210> SEQ ID NO 32
<211> LENGTH: 21
<212> TYPE: RNA
<213> ORGANISM: Artificial Sequence
<220> FEATURE:
<223> OTHER INFORMATION: 278-BrdA sense

<400> SEQUENCE: 32
cccuucauug accucaacua c                                              21

<210> SEQ ID NO 33
<211> LENGTH: 21
<212> TYPE: RNA
<213> ORGANISM: Artificial Sequence
<220> FEATURE:
<223> OTHER INFORMATION: 278-BrdA antisense
<220> FEATURE:
<221> NAME/KEY: misc_feature
<222> LOCATION: (1)..(1)
<223> OTHER INFORMATION: n = 8-oxo-2'-deoxyadenosine monophosphate

<400> SEQUENCE: 33
nguugagguc aaugaagggg u                                              21

<210> SEQ ID NO 34
<211> LENGTH: 21
<212> TYPE: RNA
```

<213> ORGANISM: Artificial Sequence
<220> FEATURE:
<223> OTHER INFORMATION: 516-BrdA sense

<400> SEQUENCE: 34
gagccaaaag ggucaucauc u                                    21

<210> SEQ ID NO 35
<211> LENGTH: 21
<212> TYPE: RNA
<213> ORGANISM: Artificial Sequence
<220> FEATURE:
<223> OTHER INFORMATION: 516-BrdA antisense
<220> FEATURE:
<221> NAME/KEY: misc_feature
<222> LOCATION: (1)..(1)
<223> OTHER INFORMATION: n = 8-oxo-2'-deoxyadenosine monophosphate

<400> SEQUENCE: 35
nugaugaccc uuuuggcucc c                                    21

<210> SEQ ID NO 36
<211> LENGTH: 21
<212> TYPE: RNA
<213> ORGANISM: Artificial Sequence
<220> FEATURE:
<223> OTHER INFORMATION: 624-BrdA sense

<400> SEQUENCE: 36
ccugcaccac caacugcuua g                                    21

<210> SEQ ID NO 37
<211> LENGTH: 21
<212> TYPE: RNA
<213> ORGANISM: Artificial Sequence
<220> FEATURE:
<223> OTHER INFORMATION: 624-BrdA antisense
<220> FEATURE:
<221> NAME/KEY: misc_feature
<222> LOCATION: (1)..(1)
<223> OTHER INFORMATION: n = 8-oxo-2'-deoxyadenosine monophosphate

<400> SEQUENCE: 37
nagcaguugg uggugcagga g                                    21

<210> SEQ ID NO 38
<211> LENGTH: 21
<212> TYPE: RNA
<213> ORGANISM: Artificial Sequence
<220> FEATURE:
<223> OTHER INFORMATION: 715-BrdA sense

<400> SEQUENCE: 38
cacugccacc cagaagacug u                                    21

<210> SEQ ID NO 39
<211> LENGTH: 21
<212> TYPE: RNA
<213> ORGANISM: Artificial Sequence
<220> FEATURE:
<223> OTHER INFORMATION: 715-BrdA antisense
<220> FEATURE:
<221> NAME/KEY: misc_feature
<222> LOCATION: (1)..(1)
<223> OTHER INFORMATION: n = 8-oxo-2'-deoxyadenosine monophosphate

<400> SEQUENCE: 39
ngucuucugg guggcaguga u                                    21

```
<210> SEQ ID NO 40
<211> LENGTH: 21
<212> TYPE: RNA
<213> ORGANISM: Artificial Sequence
<220> FEATURE:
<223> OTHER INFORMATION: 816-BrdA sense

<400> SEQUENCE: 40
aggcuguggg caaggucauc c                                              21

<210> SEQ ID NO 41
<211> LENGTH: 21
<212> TYPE: RNA
<213> ORGANISM: Artificial Sequence
<220> FEATURE:
<223> OTHER INFORMATION: 816-BrdA antisense
<220> FEATURE:
<221> NAME/KEY: misc_feature
<222> LOCATION: (1)..(1)
<223> OTHER INFORMATION: n = 8-oxo-2'-deoxyadenosine monophosphate

<400> SEQUENCE: 41
nugaccuugc ccacagccuu g                                              21

<210> SEQ ID NO 42
<211> LENGTH: 21
<212> TYPE: RNA
<213> ORGANISM: Artificial Sequence
<220> FEATURE:
<223> OTHER INFORMATION: 936-BrdA sense

<400> SEQUENCE: 42
augaugacau caagaaggug g                                              21

<210> SEQ ID NO 43
<211> LENGTH: 21
<212> TYPE: RNA
<213> ORGANISM: Artificial Sequence
<220> FEATURE:
<223> OTHER INFORMATION: 936-BrdA antisense
<220> FEATURE:
<221> NAME/KEY: misc_feature
<222> LOCATION: (1)..(1)
<223> OTHER INFORMATION: n = 8-oxo-2'-deoxyadenosine monophosphate

<400> SEQUENCE: 43
nccuucuuga ugucaucaua u                                              21

<210> SEQ ID NO 44
<211> LENGTH: 21
<212> TYPE: RNA
<213> ORGANISM: Artificial Sequence
<220> FEATURE:
<223> OTHER INFORMATION: 1096-BrdA sense

<400> SEQUENCE: 44
caagcucauu uccugguaug a                                              21

<210> SEQ ID NO 45
<211> LENGTH: 21
<212> TYPE: RNA
<213> ORGANISM: Artificial Sequence
<220> FEATURE:
<223> OTHER INFORMATION: 1096-BrdA antisense
<220> FEATURE:
<221> NAME/KEY: misc_feature
<222> LOCATION: (1)..(1)
```

```
<223> OTHER INFORMATION: n = 8-oxo-2'-deoxyadenosine monophosphate

<400> SEQUENCE: 45
nuaccaggaa augagcuuga c                                              21

<210> SEQ ID NO 46
<211> LENGTH: 21
<212> TYPE: RNA
<213> ORGANISM: Artificial Sequence
<220> FEATURE:
<223> OTHER INFORMATION: 1134-BrdA sense

<400> SEQUENCE: 46
gcaacagggu gguggaccuc a                                              21

<210> SEQ ID NO 47
<211> LENGTH: 21
<212> TYPE: RNA
<213> ORGANISM: Artificial Sequence
<220> FEATURE:
<223> OTHER INFORMATION: 1134-BrdA antisense
<220> FEATURE:
<221> NAME/KEY: misc_feature
<222> LOCATION: (1)..(1)
<223> OTHER INFORMATION: n = 8-oxo-2'-deoxyadenosine monophosphate

<400> SEQUENCE: 47
ngguccacca cccuguugcu g                                              21

<210> SEQ ID NO 48
<211> LENGTH: 21
<212> TYPE: RNA
<213> ORGANISM: Artificial Sequence
<220> FEATURE:
<223> OTHER INFORMATION: 217-A antisense

<400> SEQUENCE: 48
agcccuggug accaggcgcc c                                              21

<210> SEQ ID NO 49
<211> LENGTH: 21
<212> TYPE: RNA
<213> ORGANISM: Artificial Sequence
<220> FEATURE:
<223> OTHER INFORMATION: 278-A antisense

<400> SEQUENCE: 49
aguugagguc aaugaagggg u                                              21

<210> SEQ ID NO 50
<211> LENGTH: 21
<212> TYPE: RNA
<213> ORGANISM: Artificial Sequence
<220> FEATURE:
<223> OTHER INFORMATION: 516-A antisense

<400> SEQUENCE: 50
augaugaccc uuuuggcucc c                                              21

<210> SEQ ID NO 51
<211> LENGTH: 21
<212> TYPE: RNA
<213> ORGANISM: Artificial Sequence
<220> FEATURE:
<223> OTHER INFORMATION: 624-A antisense

<400> SEQUENCE: 51
```
aagcaguugg uggugcagga g                                        21

<210> SEQ ID NO 52
<211> LENGTH: 21
<212> TYPE: RNA
<213> ORGANISM: Artificial Sequence
<220> FEATURE:
<223> OTHER INFORMATION: 715-A antisense

<400> SEQUENCE: 52
agucuucugg guggcaguga u                                        21

<210> SEQ ID NO 53
<211> LENGTH: 21
<212> TYPE: RNA
<213> ORGANISM: Artificial Sequence
<220> FEATURE:
<223> OTHER INFORMATION: 816-A antisense

<400> SEQUENCE: 53
augaccuugc ccacagccuu g                                        21

<210> SEQ ID NO 54
<211> LENGTH: 21
<212> TYPE: RNA
<213> ORGANISM: Artificial Sequence
<220> FEATURE:
<223> OTHER INFORMATION: 936-A antisense

<400> SEQUENCE: 54
accuucuuga ugucaucaua u                                        21

<210> SEQ ID NO 55
<211> LENGTH: 22
<212> TYPE: RNA
<213> ORGANISM: Artificial Sequence
<220> FEATURE:
<223> OTHER INFORMATION: 1096-A antisense
<220> FEATURE:
<221> NAME/KEY: misc_feature
<222> LOCATION: (1)..(1)
<223> OTHER INFORMATION: n = 5-fluoro-2'-deoxyuridine monophosphate

<400> SEQUENCE: 55
nauaccagga aaugagcuug ac                                       22

<210> SEQ ID NO 56
<211> LENGTH: 21
<212> TYPE: RNA
<213> ORGANISM: Artificial Sequence
<220> FEATURE:
<223> OTHER INFORMATION: 1134-A antisense

<400> SEQUENCE: 56
agguccacca cccuguugcu g                                        21

<210> SEQ ID NO 57
<211> LENGTH: 21
<212> TYPE: RNA
<213> ORGANISM: Artificial Sequence
<220> FEATURE:
<223> OTHER INFORMATION: 1096-5-F-dU sense

<400> SEQUENCE: 57
caagcucauu uccugguaag a                                        21

```
<210> SEQ ID NO 58
<211> LENGTH: 21
<212> TYPE: RNA
<213> ORGANISM: Artificial Sequence
<220> FEATURE:
<223> OTHER INFORMATION: 1096-U antisense

<400> SEQUENCE: 58
uuaccaggaa augagcuuga c                                              21

<210> SEQ ID NO 59
<211> LENGTH: 21
<212> TYPE: RNA
<213> ORGANISM: Artificial Sequence
<220> FEATURE:
<223> OTHER INFORMATION: 1096-A sense

<400> SEQUENCE: 59
caagcucauu uccugguaug a                                              21

<210> SEQ ID NO 60
<211> LENGTH: 21
<212> TYPE: RNA
<213> ORGANISM: Artificial Sequence
<220> FEATURE:
<223> OTHER INFORMATION: 1096-A antisense

<400> SEQUENCE: 60
auaccaggaa augagcuuga c                                              21

<210> SEQ ID NO 61
<211> LENGTH: 21
<212> TYPE: RNA
<213> ORGANISM: Artificial Sequence
<220> FEATURE:
<223> OTHER INFORMATION: 1096-G sense

<400> SEQUENCE: 61
caagcucauu uccugguacg a                                              21

<210> SEQ ID NO 62
<211> LENGTH: 21
<212> TYPE: RNA
<213> ORGANISM: Artificial Sequence
<220> FEATURE:
<223> OTHER INFORMATION: 1096-G antisense

<400> SEQUENCE: 62
guaccaggaa augagcuuga c                                              21

<210> SEQ ID NO 63
<211> LENGTH: 20
<212> TYPE: DNA
<213> ORGANISM: Artificial Sequence
<220> FEATURE:
<223> OTHER INFORMATION: forward primer

<400> SEQUENCE: 63
catgaccgag aaggagatcg                                                20

<210> SEQ ID NO 64
<211> LENGTH: 19
<212> TYPE: DNA
<213> ORGANISM: Artificial Sequence
<220> FEATURE:
<223> OTHER INFORMATION: reverse primer
```

```
<400> SEQUENCE: 64
cagcttcttg gcggttgta                                          19

<210> SEQ ID NO 65
<211> LENGTH: 21
<212> TYPE: RNA
<213> ORGANISM: Artificial Sequence
<220> FEATURE:
<223> OTHER INFORMATION: 454-A sense

<400> SEQUENCE: 65
ggauagcaag accgacuauc a                                       21

<210> SEQ ID NO 66
<211> LENGTH: 21
<212> TYPE: RNA
<213> ORGANISM: Artificial Sequence
<220> FEATURE:
<223> OTHER INFORMATION: 454-A antisense

<400> SEQUENCE: 66
auagucgguc uugcuaucca u                                       21
```

OLIGONUCLEOTIDE

TECHNICAL FIELD

The present invention relates to an oligonucleotide having a knockdown activity (for example, an RNA interfering activity, or the like.) against a target messenger RNA (mRNA), and the like.

BACKGROUND ART

A small interfering RNA (hereinafter referred to as siRNA) is involved in the RNA interference (hereinafter referred to as RNAi) and is an RNA having a function as a guide for inhibiting the expression of a target gene [Nature, vol. 411, No. 6836, pp. 494-498]. An siRNA can selectively inhibit (knock down) the expression of the protein which a messenger RNA (mRNA) regulates, through cleavage of the mRNA, and therefore, the application thereof to pharmaceuticals is expected (Nature Reviews Cancer, vol. 11, pp. 59-67, 2011).

An siRNA is generally incorporated into a complex called an RNA induced silencing complex (RISC), and then exhibits its function. A main constituent component of the RISC is a protein called Argonaute 2 (AGO2), and AGO2 binds to an siRNA in the RNAi pathway and cleaves an mRNA (Trends in Biochemical Sciences, vol. 35, No. 7, pp. 368-376, 2010). The siRNA incorporated into the RISC is converted to a single strand of only the antisense strand by cleaving the sense strand, and thereafter binds to a target mRNA complementary to the antisense strand. It is known that the target mRNA is then cleaved by an RNAse domain in the AGO2, resulting in inhibiting the expression of the protein (Silence, vol. 1, p. 3, 2010).

On the other hand, in recent years, three-dimensional structure analysis of hAGO2 MID/AMP complex and hAGO2 MID/UMP complex (Nature, vol. 465, pp. 818-822, 2010), and a three-dimensional structure analysis for a complex of hAGO2 and an RNA oligonucleotide (Science, vol. 336, p. 25, 2012) have also been reported.

Further, in recent years, particularly a structural analysis of proteins using an X-ray is actively carried out, and there have been many reports of attempts to elucidate a mode of binding between a protein and a compound targeting the protein at the atomic level on the basis of the obtained structural information and to design a compound which fits the structure (Journal of Postgraduate Medicine, vol. 55, pp. 301-304, 2009).

However, although a possibility of avoiding an off-target effect (Patent Literature 1) and a possibility of enhancing the activity of an siRNA by improving the affinity for AGO2 (Non Patent Literature 1) using an oligonucleotide containing an unnatural nucleotide are suggested, a specific method for improving the affinity for AGO2 and enhancing the knockdown activity is not disclosed.

PRIOR ART

Patent Literature

[Patent Literature 1] WO2011/119674

Non Patent Literature

[Non Patent Literature 1] Molecular Therapy—Nucleic Acids vol. 1, p. e5, 2012

DISCLOSURE OF THE INVENTION

Problems to be Solved by the Invention

An object of the present invention is to provide an oligonucleotide which improves affinity for AGO2, and the like.

Means for Solving the Problems

The present invention relates to the following (1) to (69).

(1) An oligonucleotide, comprising a nucleotide residue or a nucleoside residue represented by formula (I) at the 5' And thereof, wherein the nucleotide residue or the nucleoside residue binds to an adjacent nucleotide residue through the oxygen atom at position 3:

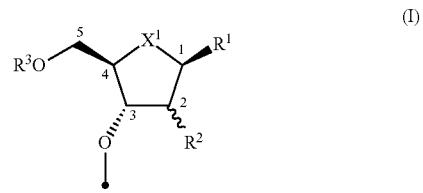

{wherein $X^1$ in an oxygen atom, a sulfur atom, a selenium atom, or $NR^4$ (wherein $R^4$ is a hydrogen atom, optionally substituted lower alkyl, optionally substituted lower alkenyl, optionally substituted lower alkynyl, optionally substituted lower alkanoyl, optionally substituted lower alkylsulfonyl, optionally substituted aralkyl, optionally substituted aryl, optionally substituted aroyl, or optionally substituted aromatic heterocyclic carbonyl), $R^1$ is formula (II):

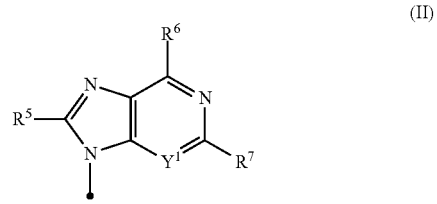

{wherein $Y^1$ is a nitrogen atom or $CR^8$ [wherein $R^8$ is a hydrogen atom, halogen, cyano, carboxy, optionally substituted lower alkyl, optionally substituted lower alkenyl, optionally substituted lower alkynyl, optionally substituted lower alkoxy, optionally substituted lower alkoxycarbonyl, optionally substituted lower alkanoyl, optionally substituted lower alkylthio, optionally substituted aryl, optionally substituted aralkyl, an optionally substituted aromatic heterocyclic group, optionally substituted aromatic heterocyclic alkyl, $-NR^{9a}R^{9b}$ (wherein $R^{9a}$ and $R^{9b}$ may be the same or different, and each is a hydrogen atom or optionally substituted lower alkyl), or $-CONR^{9c}R^{9d}$ (wherein $R^{9c}$ and $R^{9d}$ may be the same or different, and each is a hydrogen atom or optionally substituted lower alkyl)], $R^5$ is a hydrogen atom, halogen, cyano, carboxy, optionally substituted lower alkyl, optionally substituted lower alkenyl, optionally substituted lower alkynyl, optionally substituted lower alkoxy, optionally substituted lower alkoxycarbonyl, optionally substituted lower alkylthio, optionally substituted lower alkanoyl, optionally substituted aryl, an optionally substituted aromatic heterocyclic group, —NR$^{10a}$R$^{10b}$ (wherein R$^{10a}$ and R$^{10b}$ have the same meanings as R$^{9a}$ and R$^{9b}$ described above, respectively), —CONR$^{10c}$R$^{10d}$ (wherein R$^{10c}$ and R$^{10d}$ have the same meanings as R$^{9c}$ and R$^{9d}$ described above, respectively), —N═C—R$^{10e}$ (wherein R$^{10e}$ is a hydrogen atom or optionally substituted lower alkyl), —C═N—R$^{10f}$ (wherein R$^{10f}$ is a hydrogen atom or optionally substituted lower alkyl), or —N═N—R$^{10g}$ (wherein R$^{10g}$ is a hydrogen atom or optionally substituted lower alkyl), R$^6$ is a hydrogen atom, halogen, cyano, carboxy, optionally substituted lower alkyl, optionally substituted lower alkenyl, optionally substituted lower alkynyl, optionally substituted lower alkoxy, optionally substituted lower alkylthio, optionally substituted lower alkanoyl, optionally substituted lower alkoxycarbonyl, optionally substituted aryl, optionally substituted aralkyl, optionally substituted aryloxy, optionally substituted arylthio, optionally substituted aroyl, an optionally substituted aromatic heterocyclic group, optionally substituted aromatic heterocyclic alkyl, optionally substituted aromatic heterocyclicoxy, optionally substituted aromatic heterocyclicthio, optionally substituted aromatic heterocyclic carbonyl, —NR$^{11a}$R$^{11b}$ (wherein R$^{11a}$ and R$^{11b}$ may be the same or different, and each is a hydrogen atom, optionally substituted lower alkyl, optionally substituted lower alkenyl, optionally substituted lower alkynyl, optionally substituted aryl, optionally substituted aralkyl, optionally substituted aromatic heterocyclic alkyl, optionally substituted lower alkanoyl, optionally substituted lower alkylsulfonyl, optionally substituted aroyl, optionally substituted arylsulfonyl, an optionally substituted aromatic heterocyclic group, optionally substituted aromatic heterocyclic carbonyl, or optionally substituted aromatic heterocyclic sulfonyl), —CONR$^{11c}$R$^{11d}$ (wherein R$^{11c}$ and R$^{11d}$ may be the same or different, and each is a hydrogen atom, optionally substituted lower alkyl, optionally substituted aryl, or an optionally substituted aromatic heterocyclic group), —NHCONR$^{11e}$R$^{11f}$ (wherein R$^{11e}$ and R$^{11f}$ may be the same or different, and each is a hydrogen atom, optionally substituted lower alkyl, optionally substituted aralkyl, optionally substituted aromatic heterocyclic alkyl, optionally substituted aryl, or an optionally substituted aromatic heterocyclic group), or —NHCO$_2$R$^{11g}$ (wherein R$^{11g}$ is optionally substituted lower alkyl, optionally substituted aralkyl, optionally substituted aromatic heterocyclic alkyl, optionally substituted aryl, or an optionally substituted aromatic heterocyclic group), —N═C—R$^{11h}$ (wherein R$^{11h}$ is a hydrogen atom or optionally substituted lower alkyl), —C═N—R$^{11i}$ (wherein R$^{11i}$ is a hydrogen atom or optionally substituted lower alkyl), or —N═N—R$^{11j}$ (wherein R$^{11j}$ is a hydrogen atom or optionally substituted lower alkyl), R$^7$ is a hydrogen atom, an isostere of a hydrogen atom in the nucleic acid field, halogen, cyano, carboxy, optionally substituted lower alkyl, optionally substituted lower alkenyl, optionally substituted lower alkynyl, optionally substituted lower alkoxy, optionally substituted lower alkylthio, optionally substituted lower alkanoyl, optionally substituted lower alkoxycarbonyl, optionally substituted aryl, optionally substituted aralkyl, optionally substituted aryloxy, optionally substituted arylthio, optionally substituted aroyl, an optionally substituted aromatic heterocyclic group, optionally substituted aromatic heterocyclic alkyl, optionally substituted aromatic heterocyclicoxy, optionally substituted aromatic heterocyclicthio, optionally substituted aromatic heterocyclic carbonyl, —NR$^{11a}$R$^{11b}$ (wherein R$^{11a}$ and R$^{11b}$ may be the same or different, and each is a hydrogen atom, optionally substituted lower alkyl, optionally substituted lower alkenyl, optionally substituted lower alkynyl, optionally substituted aryl, optionally substituted aralkyl, optionally substituted aromatic heterocyclic alkyl, optionally substituted lower alkanoyl, optionally substituted lower alkylsulfonyl, optionally substituted aroyl, optionally substituted arylsulfonyl, an optionally substituted aromatic heterocyclic group, optionally substituted aromatic heterocyclic carbonyl, or optionally substituted aromatic heterocyclic sulfonyl), —CONR$^{11c}$R$^{11d}$ (wherein R$^{11c}$ and R$^{11d}$ may be the same or different, and each is a hydrogen atom, optionally substituted lower alkyl, optionally substituted aryl, or an optionally substituted aromatic heterocyclic group), —NHCONR$^{11e}$R$^{11f}$ (wherein R$^{11e}$ and R$^{11f}$ may be the same or different, and each is a hydrogen atom, optionally substituted lower alkyl, optionally substituted aralkyl, optionally substituted aromatic heterocyclic alkyl, optionally substituted aryl, or an optionally substituted aromatic heterocyclic group), or —NHCO$_2$R$^{11g}$ (wherein R$^{11g}$ is optionally substituted lower alkyl, optionally substituted aralkyl, optionally substituted aromatic heterocyclic alkyl, optionally substituted aryl, or an optionally substituted aromatic heterocyclic group), provided that when Y$^1$ is a nitrogen atom, R$^5$ is a hydrogen atom, R$^6$ is —NR$^{11a}$R$^{11b}$, and R$^7$ is a hydrogen atom, R$^{11a}$ and R$^{11b}$ are not simultaneously hydrogen atoms}, formula (III):

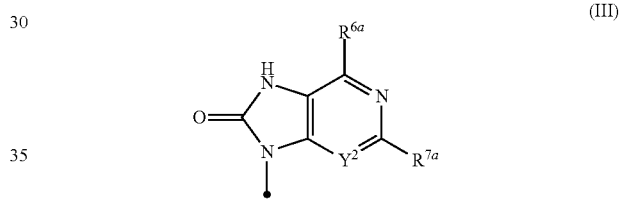

(III)

(wherein Y$^2$, R$^{6a}$, and R$^{7a}$ have the same meanings as Y$^1$, R$^6$, and R$^7$ described above, respectively), formula (IV):

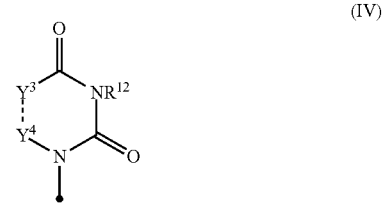

(IV)

[wherein R$^{12}$ is a hydrogen atom, an isostere of a hydrogen atom in the nucleic acid field, optionally substituted lower alkyl, optionally substituted lower alkenyl, optionally substituted lower alkynyl, optionally substituted aralkyl, optionally substituted aromatic heterocyclic alkyl, optionally substituted lower alkanoyl, or optionally substituted lower alkylsulfonyl, --- is a single bond or a double bond, provided that when --- is a single bond.

Y$^3$ is NR$^{13a}$ (wherein R$^{13a}$ is a hydrogen atom, optionally substituted lower alkyl, optionally substituted lower alkenyl, optionally substituted lower alkynyl, optionally substituted aralkyl, optionally substituted aromatic heterocyclic alkyl, optionally substituted lower alkanoyl, or optionally substituted lower alkylsulfonyl), or CR$^{14a}$R$^{14b}$ (wherein R$^{14a}$ and R$^{14b}$ may be the same or different, and each is a hydrogen atom, halogen, cyano, carboxy, optionally substituted lower alkyl, optionally substituted lower alkenyl, optionally substituted lower alkynyl, optionally substituted lower alkoxy, optionally substituted lower alkoxycarbonyl, optionally substituted lower alkanoyl, optionally substituted lower alkylthio, optionally substituted lower alkylamino, optionally substituted di-lower alkylamino, optionally substituted lower alkylcarbamoyl, optionally substituted di-lower alkylcarbamoyl, optionally substituted aryl, optionally substituted aralkyl, an optionally substituted aromatic heterocyclic group, or optionally substituted aromatic heterocyclic alkyl), and $Y^4$ is $NR^{13b}$ (wherein $R^{13b}$ has the same meaning as $R^{13a}$ described above) or $CR^{14c}R^{14d}$ (wherein $R^{14c}$ and $R^{14d}$ have the same meanings as $R^{14a}$ and $R^{14b}$ described above, respectively), and when --- is a double bond, $Y^3$ is a nitrogen atom or $CR^{14e}$ (wherein $R^{14e}$ is a hydrogen atom, halogen, cyano, carboxy, optionally substituted lower alkyl, optionally substituted lower alkenyl, optionally substituted lower alkynyl, optionally substituted lower alkoxy, optionally substituted lower alkoxycarbonyl, optionally substituted lower alkanoyl, optionally substituted lower alkylthio, optionally substituted lower alkylamino, optionally substituted di-lower alkylamino, optionally substituted lower alkylcarbamoyl, optionally substituted di-lower alkylcarbamoyl, optionally substituted aryl, optionally substituted aralkyl, an optionally substituted aromatic heterocyclic group, or optionally substituted aromatic heterocyclic alkyl) and $Y^4$ is a nitrogen atom or $CR^{14f}$ (wherein $R^{14f}$ is a hydrogen atom, halogen, cyano, carboxy, optionally substituted lower alkyl, optionally substituted lower alkenyl, optionally substituted lower alkynyl, optionally substituted lower alkoxy, optionally substituted lower alkoxycarbonyl, optionally substituted lower alkanoyl, optionally substituted lower alkylthio, optionally substituted lower alkylamino, optionally substituted di-lower alkylamino, optionally substituted lower alkylcarbamoyl, optionally substituted di-lower alkylcarbamoyl, optionally substituted aryl, optionally substituted aralkyl, an optionally substituted aromatic heterocyclic group, or optionally substituted aromatic heterocyclic alkyl), provided that when $R^{12}$ is a hydrogen atom, $Y^3$ is $CR^{14e}$, and $Y^4$ is $CR^{14f}$, the case where $R^{14e}$ and $R^{14f}$ are simultaneously hydrogen atoms or the case where $R^{14e}$ is methyl and $R^{14f}$ is a hydrogen atom is excluded], or formula (V):

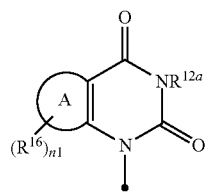

(V)

(wherein $R^{12a}$ has the same meaning as $R^{12}$ described above, ring A is an aromatic ring, n1 is an integer of 0 to 4, $R^{16}$ is halogen, hydroxy, sulfanyl, nitro, cyano, carboxy, carbamoyl, optionally substituted lower alkyl, optionally substituted lower alkenyl, optionally substituted lower alkynyl, optionally substituted lower alkoxy, optionally substituted lower alkoxycarbonyl, optionally substituted lower alkanoyl, optionally substituted lower alkylthio, optionally substituted lower alkylamino, optionally substituted di-lower alkylamino, optionally substituted lower alkylcarbamoyl, optionally substituted di-lower alkylcarbamoyl, optionally substituted aryl, optionally substituted aralkyl, an optionally substituted aromatic heterocyclic group, optionally substituted aromatic heterocyclic alkyl, or optionally substituted lower alkylsulfonyl, provided that when n1 is an integer of 2 to 4, the respective $R^{16}$'s may be the same or different), $R^2$ is a hydrogen atom, hydroxy, halogen, or optionally substituted lower alkoxy, and $R^3$ is a hydrogen atom or

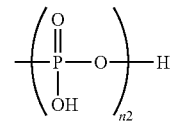

(wherein n2 is 1, 2, or 3)}.

(2) The oligonucleotide according to (1), wherein $X^1$ is an oxygen atom.

(3) The oligonucleotide according to (1) or (2), wherein $R^1$ is formula (II).

(4) The oligonucleotide according to (3), wherein $Y^1$ is a nitrogen atom.

(5) The oligonucleotide according to (3) or (4), wherein $R^5$ is a hydrogen atom, halogen, cyano, optionally substituted lower alkyl, optionally substituted lower alkenyl, optionally substituted lower alkynyl, optionally substituted lower alkoxy, optionally substituted lower alkanoyl, optionally substituted aryl, an optionally substituted aromatic heterocyclic group, —$NR^{10a}R^{10b}$ (wherein $R^{10a}$ and $R^{10b}$ have the same meanings as described above, respectively), —$CONR^{10c}R^{10d}$ (wherein $R^{10c}$ and $R^{10d}$ have the same meanings as described above, respectively), —N=C—$R^{10e}$ C (wherein $R^{10e}$ is a hydrogen atom or optionally substituted lower alkyl), —C=N—$R^{10f}$ (wherein $R^{10f}$ is a hydrogen atom ox optionally substituted lower alkyl), or —N=N— $R^{10g}$ (wherein $R^{10g}$ is a hydrogen atom or optionally substituted lower alkyl).

(6) The oligonucleotide according to (3) or (4), wherein $R^5$ is a hydrogen atom, halogen, optionally substituted lower alkenyl, or cyano.

(7) The oligonucleotide according to (3) or (4), wherein $R^5$ is optionally substituted lower alkenyl or cyano.

(8) The oligonucleotide according to any one of (3) to (7), wherein $R^6$ is optionally substituted lower alkyl, optionally substituted lower alkenyl, optionally substituted lower alkynyl, optionally substituted aryl, an optionally substituted aromatic heterocyclic group, —$NR^{11a}R^{11b}$ (wherein $R^{11a}$ and $R^{11b}$ have the same meanings as described above, respectively), —N=C—$R^{11h}$ (wherein $R^{11h}$ is a hydrogen atom or optionally substituted lower alkyl), —CαN—$R^{11i}$ (wherein $R^{11i}$ is a hydrogen atom or optionally substituted lower alkyl), or —N=N—$R^{11j}$ (wherein $R^{11j}$ is a hydrogen atom or optionally substituted lower alkyl).

(9) The oligonucleotide according to any one of (3) to (7), wherein $R^6$ is optionally substituted lower alkenyl, optionally substituted aryl, or —$NR^{11a}R^{11b}$ (wherein $R^{11a}$ and $R^{11b}$ have the same meanings as described above, respectively).

(10) The oligonucleotide according to any one of (3) to (7), wherein $R^6$ is —$NR^{11a}R^{11b}$ (wherein $R^{11a}$ and $R^{11b}$ are hydrogen atoms or optionally substituted lower alkyls).

(11) The oligonucleotide according to any one of (3) to (7), wherein $R^6$ is optionally substituted aryl and the substituent is located at the meta or para position of the aryl.

(12) The oligonucleotide according to any one of (3) to (11), wherein $R^7$ is a hydrogen atom.

(13) The oligonucleotide according to (1) or (2), wherein $R^1$ is formula (III).

(14) The oligonucleotide according to (13), wherein $Y^2$ is a nitrogen atom.

(15) The oligonucleotide according to (13) or (14), wherein $R^{6a}$ is amino, methylamino, or dimethylamino.

(16) The oligonucleotide according to any one of (13) to (15), wherein $R^7$ is a hydrogen atom.

(17) The oligonucleotide according to (1) or (2), wherein $R^1$ is formula (IV).

(18) The oligonucleotide according to (17), wherein $R^{12}$ is a hydrogen atom or an isostere of a hydrogen atom in the nucleic acid field.

(19) The oligonucleotide according to (18), wherein --- is a double bond, $Y^3$ is $CR^{14e}$ (wherein $R^{14e}$ has the same meaning as described above), and $Y^4$ is a nitrogen atom or $CR^{14f}$ (wherein $R^{14f}$ has the same meaning as described above, provided that the case where $R^{14f}$ is cyano is excluded).

(20) The oligonucleotide according to (19), wherein $R^{14e}$ is a hydrogen atom.

(21) The oligonucleotide according to (19), wherein $R^{14e}$ is halogen, cyano, optionally substituted lower alkenyl, optionally substituted aryl, or an optionally substituted aromatic heterocyclic group, and $R^{14f}$ is a hydrogen atom.

(22) The oligonucleotide according to (19), wherein $R^{14e}$ is a hydrogen atom, and $R^{14f}$ is halogen, optionally substituted lower alkyl, optionally substituted lower alkenyl, optionally substituted aryl, or an optionally substituted aromatic heterocyclic group.

(23) The oligonucleotide according to (1) or (2), wherein $R^1$ is formula (V).

(24) The oligonucleotide according to (23), wherein ring A is formula (A1).

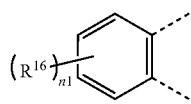
(A1)

(wherein $R^{16}$ and n1 have the same meanings as described above, respectively), formula (A2):

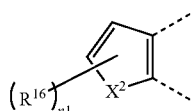
(A2)

(wherein $R^{16}$ has the same meaning as described above, n1 is an integer of 0 to 2, and $X^2$ is NH, an oxygen atom, or a sulfur atom), formula (A3):

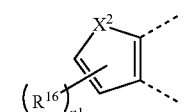
(A3)

(wherein $R^{16}$ and $X^2$ have the same meanings as described above, respectively, and n1 is an integer of 0 to 2), formula (A4):

(A4)

(wherein $R^{16}$ has the same meaning as described above, and n1 is an integer of 0 to 3), formula (A5):

(A5)

(wherein $R^{16}$ has the same meaning as described above, and n1 is an integer of 0 to 3), formula (A6):

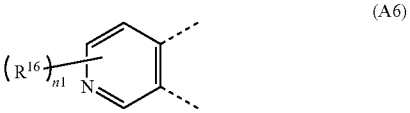
(A6)

(wherein $R^{16}$ has the same meaning as described above, and n1 is an integer of 0 to 3), formula (A7):

(A7)

(wherein $R^{16}$ has the same meaning as described above, and n1 is an integer of 0 to 3), formula (A8):

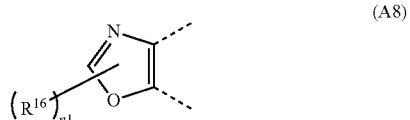
(A8)

(wherein $R^{16}$ has the same meaning as described above, and n1 is 1), formula (A9):

(A9)

(wherein $R^{16}$ has the same meaning as described above, and n1 is 1), formula (A10):

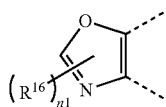

(wherein R$^{16}$ has the same meaning as described above, and n1 is 1), formula (A11):

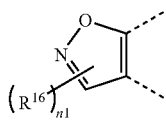

(wherein R$^{16}$ has the same meaning as described above, and n1 is 1).

(25) The oligonucleotide according to (23) or (24), wherein R$^{16}$ is halogen, nitro, optionally substituted lower alkyl, optionally substituted lower alkylamino, or optionally substituted di-lower alkylamino.

(26) The oligonucleotide according to (25), wherein R$^{12a}$ is a hydrogen atom or an isostere of a hydrogen atom in the nucleic acid field.

(27) The oligonucleotide according to any one of (23) to (26), wherein n1 is 1 or 2.

(28) The oligonucleotide according to any one of (1) to (27), wherein R$^3$ is

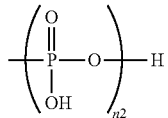

(wherein n2 has the same meaning as described above).

(29) The oligonucleotide according to (28), wherein n2 is 1.

(30) The oligonucleotide according to any one of (1) to (29), wherein R$^2$ is a hydrogen atom, hydroxy, a fluorine atom, or methoxy.

(31) The oligonucleotide according to any one of (1) to (29), wherein R$^2$ is hydroxy.

(32) The oligonucleotide according to (1), wherein X$^1$ is an oxygen atom, and R$^2$ is a hydrogen atom, hydroxy, a fluorine atom, or methoxy.

(33) The oligonucleotide according to (32), wherein R$^1$ is formula (IIA):

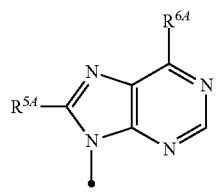

(wherein R$^{5A}$ and R$^{6A}$ have the same meanings as R$^5$ and R$^6$ described above, respectively).

(34) The oligonucleotide according to (33), wherein R$^{5A}$ is halogen, carbamoyl, optionally substituted lower alkyl, optionally substituted lower alkenyl, optionally substituted lower alkynyl, optionally substituted lower alkoxy, optionally substituted lower alkanoyl, optionally substituted lower alkylamino, optionally substituted di-lower alkylamino, optionally substituted lower alkylcarbamoyl, optionally substituted di-lower alkylcarbamoyl, optionally substituted aryl, or an optionally substituted aromatic heterocyclic group.

(35) The oligonucleotide according to (33), wherein R$^{5A}$ is halogen or cyano.

(36) The oligonucleotide according to any one of (33) to (35), wherein R$^{6A}$ is optionally substituted lower alkyl, optionally substituted lower alkenyl, optionally substituted lower alkynyl, optionally substituted aryl, an optionally substituted aromatic heterocyclic group, or NR$^{11a}$R$^{11b}$ (wherein R$^{11a}$ and R$^{11b}$ have the same meanings as described above, respectively).

(37) The oligonucleotide according to any one of (33) to (35), wherein R$^{6A}$ is NR$^{11a}$R$^{11b}$ (wherein R$^{11a}$ and R$^{11b}$ have the same meanings as described above, respectively).

(38) The oligoncucletide according to any one of (33) to (35), wherein R$^{6A}$ is amino, optionally substituted lower alkenyl, or optionally substituted aryl.

(39) The oligonucleotide according to (32), wherein R$^1$ is formula (IVA):

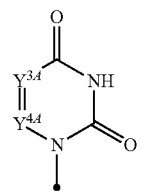

l(wherein Y$^{3A}$ and Y$^{4A}$ have the same meanings as Y$^3$ and Y$^4$ described above, respectively, provided that when Y$^{3A}$ and Y$^{4A}$ are CR$^{14e}$ and CR$^{14f}$, and R$^{14e}$ is a hydrogen atom, R$^{14f}$ is not cyano).

(40) The oligonucleotide according to (39), wherein Y$^{3A}$ is CR$^{14e}$ (wherein R$^{14e}$ has the same meaning as described above) and Y$^{4A}$ is CR$^{14f}$ (wherein R$^{14f}$ has the same meaning as described above).

(41) The oligonucleotide according to (40), wherein R$^{14e}$ is a hydrogen atom.

(42) The oligonucleotide according to (40), wherein R$^{14e}$ is halogen, optionally substituted lower alkenyl, optionally substituted aryl, or an optionally substituted aromatic heterocyclic group, and R$^{14f}$ is a hydrogen atom.

(43) The oligonucleotide according to (40), wherein R$^{14e}$ is a hydrogen atom, and R$^{14f}$ is halogen, optionally substituted lower alkyl, optionally substituted lower alkenyl, optionally substituted aryl, or an optionally substituted aromatic heterocyclic group.

(44) The oligonucleotide according to (32), wherein R$^1$ is formula (VA):

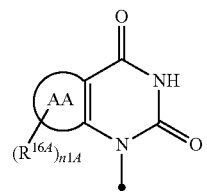

(wherein ring AA, n1A, and $R^{16A}$ a have the same meanings as ring A, n1, and $R^{16}$ described above, respectively, provided that when n1A is an integer of 2 to 4, the respective $R^{16A}$'s may be the same or different, provided that when ring AA is a benzene ring and n1A is 2, $R^{16A}$'s are not lower alkoxy, and when ring AA is a benzene ring, n1A is 1, and $R^{16A}$ is a chlorine atom, the case where ring AA is represented by formula (A1')

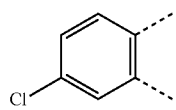

is excluded).

(45) The oligonucleotide according to (44), wherein ring AA is a benzene ring or a thiophene ring.

(46) The oligonucleotide according to (44) or (45), wherein $R^{16A}$ is halogen, nitro lower alkyl, optionally substituted lower alkylamino, or optionally substituted di-lower alkylamino.

(47) The oligonucleotide according to any one of (44) to (46), wherein n1A is 1 or 2.

(48) The oligonucleotide according to any one of (32) to (47), wherein $R^{3A}$ is

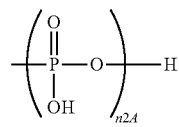

(wherein n2A has the same meaning as described above).

(49) The oligonucleotide according to (49), wherein n2A is 1.

(50) The oligonucleotide according to any one of (32) to (49), wherein $R^{2A}$ is a hydrogen atom, hydroxy, a fluorine atom, or methoxy.

(51) The oligonucleotide according to any one of (32) to (49), wherein $R^{2A}$ is hydroxy.

(52) The oligonucleotide according to any one of (1) to (51), wherein the oligonucleotide has a length of 10 to 80 bases.

(53) The oligonucleotide according to any one of (1) to (51), wherein the oligonucleotide has a length of 20 to 50 bases.

(54) The oligonucleotide according to any one of (1) to (51), wherein the oligonucleotide has a length of 20 to 30 bases.

(55) The oligonucleotide according to any one of (1) to (51), wherein the oligonucleotide has a length of 21 to 25 bases.

(56) The oligonucleotide according to any one of (1) to (55), wherein the oligonucleotide is a double-stranded oligonucleotide.

(57) The oligonucleotide according to any one of (1) to (55), wherein the oligonucleotide is a single-stranded oligonucleotide.

(58) The oligonucleotide according to any one of (1) to (55), wherein the oligonucleotide is a small interfering RNA (siRNA).

(59) A method for improving the knockdown activity of an oligonucleotide, wherein the oligonucleotide has a knockdown activity against a mRNA encoding a protein involved in a disease, characterized by comprising substituting a base residue at the 5' end of the oligonucleotide with a base residue represented by formula (II):

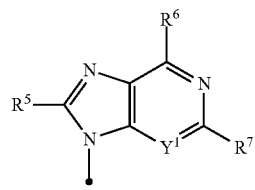

(wherein $Y^1$, $R^5$, $R^6$, and $R^7$ have the same meanings as described above, respectively), formula (III):

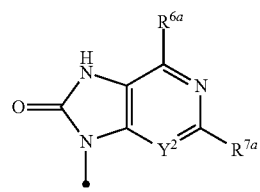

(wherein $Y^2$, $R^{6a}$, and $R^{7a}$ have the same meanings as described above, respectively), formula (IV):

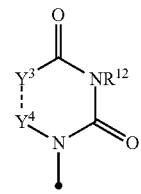

(wherein $R^{12}$, ---, $Y^3$, and $Y^4$ have the same meanings as described above, respectively), or formula (V):

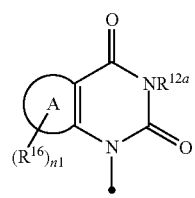

(wherein $R^{12a}$, ring A, n1, and $R^{16}$ have the same meanings as described above, respectively).

(60) A method for improving the knockdown activity of an oligonucleotide, wherein the oligonucleotide has a knockdown activity against a messenger RNA (mRNA) encoding a protein involved in a disease and the base at the 5' end of the oligonucleotide is guanine or cytosine, characterized by comprising substituting the guanine residue or the cytosine residue at the 5' end of the oligonucleotide with an adenine residue (6-aminopurin-9-yl), a thymine residue (5-methyl-1,2,3,4tetrahydropyrimidine2,4-dion-1-yl), an uridine residue (pyrimidine-2,4(1H,3H)dion-1-yl), or a base residue represented by formula (II):

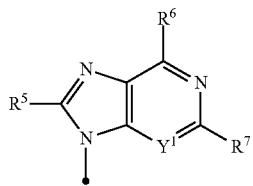

(wherein $Y^1$, $R^5$, $R^6$, and $R^7$ have the same meanings as described above, respectively), formula (III):

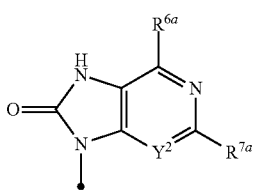

(wherein $Y^2$, $R^{6a}$, and $R^{7a}$ have the same meanings as described above, respectively), formula (IV):

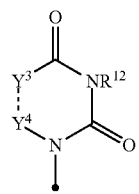

(wherein $R^{12}$, ---, $Y^3$, and $Y^4$ have the same meanings as described above, respectively), or formula (V):

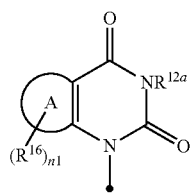

(wherein $R^{12a}$, ring A, n1, and $R^{16}$ have the same meanings as described above, respectively).

(61) The method according to (59) or (60), wherein the oligonucleotide is a small interfering RNA (siRNA).

(62) A nucleic acid pharmaceutical composition, comprising an oligonucleotide, wherein the knockdown activity of the oligonucleotide against a target mRNA is improved by the method according to any one of (59) to (61).

(63) A nucleotide or a nucleoside represented by formula (Ia):

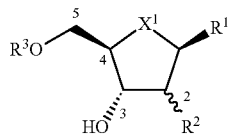

(wherein $X^1$, $R^1$, $R^2$, and $R^3$ have the same meanings as described above, respectively), or the one wherein hydroxy, carboxyl, and/or amino are(is) protected by a protecting group, or an amidite thereof or a salt thereof, for use in substituting a nucleotide residue or a nucleoside residue at the 5' end of the oligonucleotide having a knockdown activity against a mRNA encoding a protein involved in a disease, and for improving the knockdown activity against a target mRNA of the oligonucleotide.

(64) The nucleotide or nucleoside, or the one wherein hydroxy, carboxyl, and/or amino are(is) protected by a protecting group, or an amidite thereof, or a salt thereof according to (63), wherein the oligonucleotide is a small interfering RNA (siRNA).

(65) A nucleotide or a nucleoside, comprising a base residue represented by formula (IT):

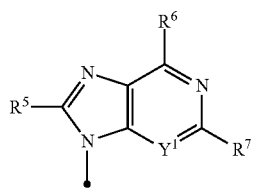

(wherein $Y^1$, $R^5$, $R^6$, and $R^7$ have the same meanings as described above, respectively), formula (III):

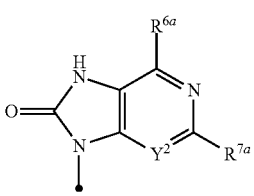

(wherein $Y^2$, $R^{6a}$, and $R^{7a}$ have the same meanings as described above, respectively), formula (IV):

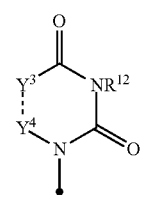

(wherein $R^{12}$, ---, $Y^3$, and $Y^4$ have the same meanings as described above, respectively), or formula (V):

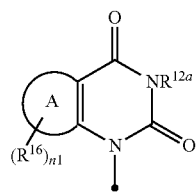

(V)

(wherein $R^{12a}$, ring A, n1, and $R^{16}$ have the same meanings as described above, respectively), or the one wherein hydroxy, carboxyl, and/or amino are(is) protected by a protecting group, or an amidite thereof or a salt thereof, for use in substituting a nucleotide residue or a nucleoside residue at the 5' end of an oligonucleotide having a knockdown activity against a mRNA encoding a protein involved in a disease, and for improving the knockdown activity against a target mRNA of the oligonucleotide.

(66) The nucleotide or nucleoside, or the one wherein hydroxy, carboxyl, and/or amino are(is) protected by a protecting group, or an amidite thereof or a salt thereof according to (65), wherein the oligonucleotide is a small interfering RNA (siRNA).

(67) Use of an oligonucleotide which has a nucleotide residue or a nucleoside residue represented by formula (I) at the 5' end:

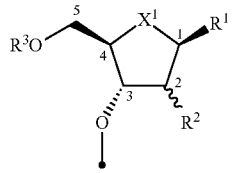

(I)

(wherein $X^1$, $R^1$, $R^2$, and $R^3$ have the same meanings as described above, respectively) and has a knockdown activity against a mRNA encoding a protein involved in a disease, for the manufacture of an inhibitor of a target protein expression.

(68) Use of an oligonucleotide introducing a base residue represented by formula (I)):

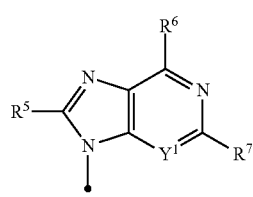

(II)

(wherein $Y^1$, $R^5$, $R^6$, and $R^7$ have the same meanings as described above, respectively), formula (III):

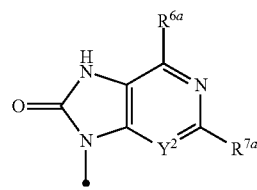

(III)

(wherein $Y^2$, $R^{6a}$, and $R^{7a}$ have the same meanings as described above, respectively), formula (IV):

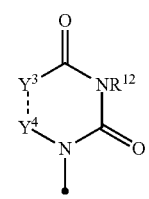

(IV)

(wherein $R^{12}$, ---, $Y^3$, and $Y^4$ have the same meanings as described above, respectively), or formula (V):

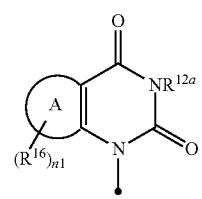

(V)

(wherein $R^{12a}$, ring A, n1, and $R^{16}$ have the same meanings as described above, respectively) at the 5' end, and the oligonucleotide has a knockdown activity against a mRNA encoding a protein involved in a disease, for the manufacture of an inhibitor of a target protein expression.

(69) The use according to (67) or (68), wherein the oligonucleotide is a small interfering RNA (siRNA).

Effect of the Invention

According to the present invention, an oligonucleotide having improved the affinity for AGO2 and the like are provided

BRIEF DESCRIPTION OF DRAWING

FIG. 1 is a graph for comparing the levels of luciferase luminescence between an siRNA having 8-Br-dA at the 5' end of the antisense strand and an siRNA having adenosine monophosphate at the 5' end of the antisense strand with respect to luciferase-targeting siRNAs (concentration: 100 pmol/L). The ordinate represents the ratio of luminescence in the case of using each siRNA when the amount of luminescence in a negative control group is taken as 1.

FIG. 2 is a graph for comparing the levels of luciferase luminescence between an siRNA having 8-Br-dA at the 5' end of the antisense strand (874-BrdA) and an siRNA having adenosine monophosphate (874-A), guanosine monophosphate (874-G), cytidine monophosphate (874-C), or uridine monophosphate (874-U) at the 5' end of the antisense strand with respect to luciferase-targeting siRNAs. The ordinate represents the ratio of luminescence in the case of using each siRNA when the amount of luminescence in a negative control group is taken as 1. In the abscissa, A, G, C, U, and BrdA denote 874-A, 874-G, 874-C, 874-U, and 874-BrdA, respectively. The results of the test performed by setting the concentration of each siRNA to 3.2 pmol/L, 16 pmol/L, 80 pmol/L, and 400 pmol/L are shown.

FIG. 3 is a graph for comparing the expression levels of GAPDH mRNA between an siRNA having 8-Br-dA at the 5' end of the antisense strand and an siRNA having adenosine monophosphate at the 5' end of the antisense strand with respect to siRNAs targeting D-glyceraldehyde-3-phosphate dehydrogenase (GAPDH, GenBank Accession No. NM_001256799). The ordinate represents the relative expression level of GAPDH mRNA when the GAPDH mRNA level in a negative control group is taken as 1. The abscissa represents respective siRNAs, more specifically, the left side represents siRNAs having adenosine monophosphate at the 5' end of the antisense strand (217-A, 278-A, 516-A, 624-A, 715-A, 816-A, 936-A, 1096-A, and 1134-A), and the right side represents siRNAs having 8-Br-dA at the 5' end of the antisense strand (217-BrdA, 278-BrdA, 516-BrdA, 624-BrdA, 715-BrdA, 816-BrdA, 936-BrdA, 1096-BrdA, and 1134-BrdA).

FIG. 4 is a graph showing the knockdown activity of each of siRNAs having adenosine monophosphate (454-A), uridine monophosphate (454-U), 8-Br-dA (454-BrdA), I-37 (6-NO2,7-Me-dQu), I-21 (6-napht-2-yl-dPu), I-34 (6-Me-dU), or I-25 (6-napht-1-yl-dPu) at the 5' end of the antisense strand with respect to luciferase-targeting siRNAs. The ordinate represents the 50% inhibitory concentration ($IC_{50}$), and the abscissa represents the siRNAs used.

FIG. 5 is a graph showing the knockdown activity of each of siRNAs having adenosine monophosphate (454-A), uridine monophosphate (454-U), 8-Br-dA (454-BrdA), I-32 (2'-OMe-6-styryl-dA), or I-19 (di-Me-thienyl-dU) at the 5' end of the antisense strand with respect to luciferase-targeting siRNAs. The ordinate represents the 50% inhibitory concentration ($IC_{50}$), and the abscissa represents the siRNAs used.

MODE FOR CARRYING OUT THE INVENTION

Hereinafter, a compound represented by formula (I) wherein $X^1$ is an oxygen atom, $R^2$ is a hydrogen atom, hydroxy, a fluorine atom, or methoxy refers to Compound (Ia). The compounds having the other formula numbers are referred to in the same manner.

In the definitions of the respective groups in formulae (I), (II), (III), (IV), (V), (IIA), (IIIA), (IVA), (VA), (Ia), and (A1) to (A11), (i) the halogen means each atom of fluorine, chlorine, bromine, and iodine.

(ii) Examples of the lower alkyl and the lower alkyl moieties of the lower alkoxy, the lower alkoxycarbonyl, the lower alkylamino, the di-lower alkylamino, the lower alkylcarbamoyl, the di-lower alkylcarbamoyl, the lower alkylthio, and the lower alkylsulfonyl include linear or branched alkyl having 1 to 10 carbon atom(s). Specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl, and the like. The two lower alkyl moieties of the di-lower alkylamino and the di-lower alkylaminocarbamoyl may be the same or different.

(iii) The alkylene moieties of the aralkyl and the aromatic heterocyclic alkyl have the same meanings as groups in which one hydrogen atom is removed from the lower alkyl described in the above (ii).

(iv) Examples of the lower alkenyl include linear or branched alkenyl having 2 to 10 carbon atoms. Specific examples thereof include vinyl, allyl, 1-propenyl, isopropenyl, methacryl, butenyl, crotyl, pentenyl, hexenyl, heptenyl, octenyl, nonenyl, decenyl, and the like.

(v) Examples of the lower alkynyl include linear or branched alkynyl having 2 to 10 carbon atoms. Specific examples thereof include ethynyl, propargyl, butynyl, pentynyl, hexynyl, heptynyl, octynyl, nonynyl, decynyl, and the like.

(vi) Examples of the lower Alkanoyl include linear oz branched lower alkanoyl having 1 to 8 carbon atom(s). Specific examples thereof include formyl, acetyl, propionyl, butyryl, isobutyryl, valeryl, isovaleryl, pivaloyl, hexanoyl, heptanoyl, octanoyl, and the like.

(vii) Examples of the aryl and the aryl moieties of the aralkyl, the aroyl, the aryloxy, the arylthio, and the arylsulfonyl include aryl having 6 to 14 carbon atoms. Specific examples thereof include phenyl, naphthyl, indenyl, anthryl, and the like, and preferred examples thereof include phenyl, naphthyl, and the like.

(viii) Examples of the aromatic heterocyclic group and the aromatic heterocyclic group moieties of the aromatic heterocyclic alkyl, the aromatic heterocyclic carbonyl, the aromatic heterocyclicoxy, the aromatic heterocyclicthio, and the aromatic heterocyclic sulfonyl include a 5- or 6-membered monocyclic aromatic heterocyclic group containing at least one atom selected from a nitrogen atom, an oxygen atom, and a sulfur atom, a bicyclic or tricyclic fused-ring aromatic heterocyclic group in which 3- to 8-membered rings are fused and at least one atom selected from a nitrogen atom, an oxygen atom, and a sulfur atom is contained, and the like. Specific examples thereof include pyridyl, pyrazinyl, pyrimidinyl, pyridazinyl, oxopyridazinyl, quinolyl, isoquinolyl, phthalazinyl, quinazolinyl, quinoxalinyl, naphthyridinyl, cinnolinyl, pyrrolyl, pyrazolyl, imidazolyl, triazinyl, triazolyl, tetrazolyl, thienyl, furyl, thiazolyl, isothiazolyl, oxazolyl, isoxazolyl, oxadiazolyl, thiadiazolyl, indolyl, isoindolyl, indazolyl, benzofuryl, isobenzofuryl, benzothienyl, benzoimidazolyl, benzotriazolyl, benzothiazolyl, benzoxazolyl, pyrazolopyridyl, pyrazolopyrimidinyl, purinyl, dibenzofuranyl, dibenzoazepinyl, and the like, and preferred examples thereof include pyridyl, pyrrolyl, thienyl, oxazolyl, and the like.

(ix) Examples of the aromatic ring include a benzene ring, a naphthalene ring, an aromatic heterocyclic ring, and the like. The aromatic heterocyclic ring has the same meaning as the one formed by adding a hydrogen atom to the aromatic heterocyclic group described above and the an aromatic heterocyclic group moiety of the aromatic heterocyclic alkyl, the aromatic heterocyclic carbonyl, the aromatic heterocyclicoxy, the aromatic heterocyclicthio, and the aromatic heterocyclic sulfonyl.

(x) The substituents of the optionally substituted lower alkyl, the optionally substituted lower alkenyl, the optionally substituted lower alkynyl, the optionally substituted lower alkoxy, the optionally substituted lower alkoxycarbonyl, the optionally substituted lower alkanoyl, the optionally substituted lower alkylamino, the optionally substituted di-lower alkylamino, the optionally substituted lower alkylcarbamoyl, the optionally substituted di-lower alkylcarbamoyl, the optionally substituted lower alkylthio, and the optionally substituted lower alkylsulfonyl may be the same or different and in number of, for example, 1 to 3, and examples of the substituents include substituents selected from the group consisting of halogen, hydroxy, sulfanyl, nitro, cyano, carboxy, carbamoyl, $C_{3-8}$ cycloalkyl, an aliphatic heterocyclic group, $C_{1-10}$ alkoxy, $C_{3-8}$ cycloalkoxy, $C_{6-14}$ aryloxy, $C_{7-16}$ aralkyloxy, $C_{1-8}$ alkanoyloxy, $C_{7-15}$ aroyloxy, $C_{1-10}$ alkylsulfanyl, —$NR^X R^Y$ (wherein $R^X$ and $R^Y$ may be the same or different and are a hydrogen atom, $C_{1-10}$ alkyl, $C_{3-8}$ cycloalkyl, $C_{6-14}$ aryl, an aromatic heterocyclic group, $C_{7-16}$ aralkyl, $C_{1-8}$ alkanoyl, $C_{7-15}$ aroyl, $C_{1-10}$ alkoxycarbonyl, or $C_{7-16}$ aralkyloxycarbonyl, $C_{1-8}$ alkanoyl, $C_{7-15}$ aroyl, $C_{1-10}$ alkoxycarbonyl, $C_{6-14}$ aryloxycarbonyl, $C_{1-10}$ alkylcarbamoyl, and di-$C_{1-10}$ alkylcarbamoyl, and the like. The substituents of the optionally substituted lower alkenyl, the optionally substituted lower alkynyl, the optionally substituted lower alkoxy, the optionally substituted lower alkoxycarbonyl, the optionally substituted lower alkanoyl, the optionally substituted lower alkylamino, the optionally substituted di-lower alkylamino, the optionally substituted lower alkylcarbamoyl, the optionally substituted di-lower alkylcarbamoyl, the optionally substituted lower alkylthio, and the optionally substituted lower alkyl sulfonyl may be substituents selected from the group consisting of $C_{6-14}$ aryl and an aromatic heterocyclic group in addition to the above-described substituents.

(xi) The substituents of the optionally substituted aryl, the optionally substituted aralkyl, the optionally substituted aryloxy, the optionally substituted arylthio, the optionally substituted arylsulfonyl, the optionally substituted aroyl, the optionally substituted aromatic heterocyclic group, the optionally substituted aromatic heterocyclic alkyl, the optionally substituted aromatic heterocyclic carbonyl, the optionally substituted aromatic heterocyclicoxy, the optionally substituted aromatic heterocyclicthio, the optionally substituted aromatic heterocyclic sulfonyl, and the optionally substituted styryl may be the same or different and in number of, for example, 1 to 3, and examples of the substituents include substituents selected from the group consisting of halogen, hydroxy, sulfanyl, nitro, cyano, carboxy, carbamoyl, $C_{1-10}$ alkyl, trifluoromethyl, $C_{3-8}$ cycloalkyl, $C_{6-14}$ aryl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{1-8}$ alkanoyloxy, $C_{7-15}$ aroyloxy, $C_{1-10}$ alkylsulfanyl, —$NR^{Xa} R^{Ya}$ (wherein $R^{Xa}$ and $R^{Ya}$ may be the same or different, and each is a hydrogen atom, $C_{1-10}$ alkyl, $C_{3-8}$ cycloalkyl, $C_{6-14}$ aryl, an aromatic heterocyclic group, $C_{7-16}$ aralkyl, $C_{1-8}$ alkanoyl, $C_{7-15}$ aroyl, $C_{1-10}$ alkoxycarbonyl, or $C_{7-16}$ aralkyloxycarbonyl), $C_{1-8}$ alkanoyl, $C_{7-15}$ aroyl, $C_{1-10}$ alkoxycarbonyl, $C_{6-14}$ aryloxycarbonyl, $C_{1-10}$ alkylcarbamoyl, and di-$C_{1-10}$ alkylcarbamoyl, and the like, and preferred examples thereof, in number of 1, include halogen, hydroxy, sulfanyl, nitro, cyano, carboxy, $C_{1-3}$ alkyl, trifluoromethyl, $C_{1-3}$ alkoxy, and the like.

Examples of the $C_{1-10}$ alkyl and the $C_{1-10}$ alkyl moieties of the $C_{1-10}$ alkoxy, the $C_{1-10}$ alkylsulfanyl, the $C_{1-10}$ alkoxycarbonyl, the $C_{1-10}$ alkylcarbamoyl, and the di-$C_{1-10}$ alkylcarbamoyl described above include the groups exemplified as the lower alkyl described above. The two $C_{1-10}$ alkyl moieties of the di-$C_{1-10}$ alkylcarbamoyl may be the same or different.

Examples of the $C_{1-8}$ alkanoyl and the $C_{1-8}$ alkanoyl moiety of the $C_{1-8}$ alkanoyloxy include the groups exemplified as the lower alkanoyl described above.

Examples of the $C_{3-8}$ cycloalkyl and the $C_{3-8}$ cycloalkyl moiety of the $C_{3-8}$ cycloalkoxy include cyclopropyl, cyclobutyl, cyclopentyl, cyclohexyl, cycloheptyl, cyclooctyl, and the like.

Examples of the $C_{6-14}$ aryl and the aryl moieties of the $C_{6-14}$ aryloxy, the $C_{7-15}$ aroyl, the $C_{7-15}$ aroyloxy, and the $C_{6-14}$ aryloxycarbonyl include the groups exemplified as the aryl described above.

Examples of the aryl moieties of the $C_{7-16}$ aralkyloxy, the $C_{7-16}$ aralkyl, and the $C_{7-16}$ aralkyloxycarbonyl include the groups exemplified as the aryl described above. Examples of the alkylene moieties include $C_{1-10}$ alkylene, and more specifically include groups in which one hydrogen atom is removed from the groups exemplified as the lower alkyl described above.

Examples of the aliphatic heterocyclic group include a 5- or 6-membered monocyclic aliphatic heterocyclic group containing at least one atom selected from a nitrogen atom, an oxygen atom, and a sulfur atom, a bicyclic or tricyclic fused-ring aliphatic heterocyclic group in which 3- to 8-membered rings are fused and at least one atom selected from a nitrogen atom, an oxygen atom, and a sulfur atom is contained, and the like. Specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzoxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, and the like.

The halogen and the aromatic heterocyclic group have the same meanings as described above, respectively.

Here, in the above formula (II), it is preferred that $Y^1$ is a nitrogen atom or the like; $R^5$ is hydrogen, halogen, cyano, optionally substituted lower alkenyl, or the like; $R^6$ is optionally substituted aryl, optionally substituted alkenyl, —$NR^{11a} R^{11b}$ (wherein $R^{11a}$ and $R^{11b}$ have the same meanings as described above, respectively), or the like; and $R^7$ is a hydrogen atom, an isostere of a hydrogen atom in the nucleic acid field (for example, a deuterium atom, amino, hydroxy, a fluorine atom, or the like), or the like. Incidentally, in case where the above $R^6$ is substituted aryl, it is preferred that the substituent is located at the meta or para position of the aryl.

Further, in the above formula (IV), it is preferred that $R^{12}$ is a hydrogen atom, an isostere of a hydrogen atom in the nucleic acid field (for example, a deuterium atom, amino, hydroxy, a fluorine atom, or the like), or the like; --- is a double bond; $Y^3$ is $CR^{14e}$; $Y^4$ is a nitrogen atom or $CR^{14f}$; and $R^{14e}$ and $R^{14f}$ are a hydrogen atom, halogen, cyano, optionally substituted lower alkenyl, optionally substituted aryl, an optionally substituted aromatic heterocyclic group, or the like.

Still further, in the above formula (V), it is preferred that $R^{12a}$ is hydrogen, an isostere of a hydrogen atom in the nucleic acid field (for example, a deuterium atom, amino, hydroxy, a fluorine atom, or the like), or the like; ring A is a benzene ring, a thiophene ring, or the like; n1 is 1 or 2; and $R^{16}$ is halogen, nitro, optionally substituted alkyl, optionally substituted lower alkylamino, or optionally substituted di-lower alkylamino.

The oligonucleotide of the present invention means a polymer or an oligomer comprising a nucleotide residue or a nucleoside residue.

The oligonucleotide of the present invention includes both of a single-stranded oligonucleotide and a double-stranded oligonucleotide. In a double-stranded oligonucleotide, the base lengths of the respective oligonucleotide strands may be different. Further, the double-stranded oligonucleotide may contain one or more mismatched base pairs. In addition, a complex formed of three or more oligonucleotide strands is also included in the oligonucleotide of the present invention.

The oligonucleotide of the present invention preferably has a knockdown activity against an mRNA encoding, for example, a protein involved in a disease. Here, the "having a knockdown activity" as used in the specification means inhibiting the expression of a gene (target gene) encoding a protein or the like, and it is preferred that the oligonucleotide of the present invention has the activity preferably 2 times, more preferably 5 times, further more preferably 10 times higher than that of an siRNA containing a corresponding natural nucleotide at the 5' end of the oligonucleotide.

Examples of the double-stranded oligonucleotide include a double-stranded DNA such as a structural gene, a double-stranded RNA such as a small molecule RNA including an siRNA and a miRNA, and the like. However, the present invention is not limited thereto.

Examples of the single-stranded oligonucleotide include an antisense oligonucleotide, a microRNA, an aptamer, an antagomir, a single-stranded RNAi agent (such as an siRNA having a hairpin structure), and the like. However, the present invention is not limited thereto.

The length of the oligonucleotide of the present invention is preferably 10 to 100 bases, more preferably 10 to 80 bases, further more preferably 10 to 50 bases, particularly preferably 20 to 50 bases, and the most preferably 20 to 30 bases.

In the oligonucleotide of the present invention, in addition to the nucleotide residue or the nucleoside residue at the 5' end, further one or more nucleotide residues may be modified. Such modification may be contained in any site of a base, a sugar, and a phosphate.

A base-modified nucleotide may be any as long as it is a nucleotide in which a part or the whole of the chemical structure of a base of the nucleotide is modified with an arbitrary substituent or is substituted with an arbitrary atom, and examples thereof include a nucleotide in which an oxygen atom in a base is substituted with a sulfur atom, a nucleotide in which a hydrogen atom in a base is substituted with alkyl having 1 to 10 carbon atoms, a nucleotide in which methyl in a base is substituted with hydrogen or alkyl having 2 to 10 carbon atoms, and a nucleotide in which amino is protected by a protecting group such as an alkyl group having 1 to 10 carbon atoms, alkanoyl having 1 to 8 carbon atoms, or the like.

A sugar moiety-modified nucleotide may be any as long as it is a nucleotide in which a part or the whole of the chemical structure of a sugar of the nucleotide is modified with an arbitrary substituent or is substituted with an arbitrary atom. And, a 2'-modified nucleotide is preferably used.

Examples of the 2'-modified nucleotide include a 2'-modified nucleotide in which the 2'-OH of a ribose is substituted with a substituent selected from a hydrogen atom, —OR, —R, —R', —SH, —SR, amino, —NHR, —NR$_2$, N$_3$, cyano, and halogen (wherein R is lower alkyl or aryl, and the lower alkyl, the aryl, and the halogen have the same meanings as described above, respectively). Specific examples thereof include a 2'-modified nucleotide in which the 2'-OH is substituted with a substituent selected from the group consisting of a fluorine atom, methoxy, 2-(methoxy) ethoxy, 3-aminopropoxy, 2-[(N,N-dimethylamino)oxy]ethoxy, 3-(N,N-dimethylamino) propoxy, 2-[2-(N,N-dimethylamino) ethoxy]ethoxy, 2-(methylamino)-2-oxoethoxy, 2-(N-methylcarbamoyl)ethoxy, and 2-cyanoethoxy, and the like.

A phosphate-modified nucleotide may be any as long as it is a nucleotide in which a part or the whole of the chemical structure of a phosphodiester bond of the nucleotide is modified with an arbitrary substituent or is substituted with an arbitrary atom, and examples thereof include a nucleotide in which a phosphodiester bond is substituted with an alkyl phosphonate bond, and the like.

As the oligonucleotide which has a knockdown activity against an mRNA encoding a protein involved in a disease, any nucleic acid, for example, An oligonucleotide which contains a base sequence complementary to a partial base sequence of the mRNA of a gene (target gene) encoding a protein or the like and inhibits the expression of the target gene can be used. Specifically, a double-stranded oligonucleotide such as an siRNA (short interference RNA) or a miRNA (micro RNA), a single-stranded oligonucleotide such as an shRNA (short hairpin RNA), an antisense nucleic acid, or a ribozyme may be used. And, a double-stranded oligonucleotide is preferred.

An oligonucleotide strand containing a base sequence complementary to a partial base sequence of the target gene mRNA is referred to as an antisense strand, and an oligonucleotide containing a base sequence complementary to the base sequence of the antisense strand is referred to as a sense strand. The sense strand refers to an oligonucleotide itself consisting of a partial base sequence of the target gene and the like, namely an oligonucleotide which can form a double strand-forming region by pairing with the antisense strand. In a double-stranded oligonucleotide containing a base sequence complementary to a partial base sequence of the target gene mRNA, the 5' end of the oligonucleotide means the 5' end of the antisense strand.

In the oligonucleotide of the present invention, a double strand-forming region formed by base pairing between an antisense strand and a sense strand has generally 15 to 27 base pairs, preferably 15 to 25 base pairs, more preferably 15 to 23 base pairs, further more preferably 15 to 21 base pairs, and particularly preferably 15 to 19 base pairs. The double strand-forming region may be any as long as the bases of each of the antisense strand and the sense strand pair with each other, and base pairs may be formed or mismatched. And the base at the 5' end of the antisense strand and the base of the sense strand to be paired therewith preferably form an adenosine uracil (A-U) base pair or a mismatched base pair.

The oligonucleotide in either the antisense strand or the sense strand which constitutes a double-stranded oligonucleotide, or both of them which constitute a double-stranded oligonucleotide may have an additional nucleotide which does not form a double strand on the 3' side or the 5' side of the double strand-forming region. Such a region which does not form a double strand is also referred to as a protrusion (overhang).

As the double-stranded oligonucleotide having a protrusion, for example, a double-stranded oligonucleotide having a protrusion consisting of 1 to 4 bases, generally 1 to 3 bases at the 3' end or the 5' end of at least one strand is used. Also, a double-stranded oligonucleotide having a protrusion consisting of 2 bases is preferably used, and a double-stranded oligonucleotide having a protrusion consisting of dTdT or UU is more preferably used. A protrusion may be present on only the antisense strand, only the sense strand, and both of the antisense strand and the sense strand. And, a double-stranded nucleic acid having a protrusion on both of the antisense strand and the sense strand is preferably used.

In addition, a sequence which is contiguous with the double strand-forming region and partially or completely matches the base sequence of the target gene mRNA, or a sequence which is contiguous with the double strand-forming region and partially or completely matches the base sequence of the complementary strand of the target gene mRNA may also be used. Further, as the double-stranded oligonucleotide, for example, a nucleic acid molecule which forms a double-stranded oligonucleotide having a protrusion described above resulted from the action of a ribonuclease such as Dicer (WO2005/089287), at least a double-stranded oligonucleotide which does not have a protrusion at the 3' end or the 5' end, or the like can also be used.

Further, in the above-described double-stranded oligonucleotide, preferably, at least a sequence of bases (nucleosides) at positions 2 to 17 from the 5' end side to the 3' end side of the antisense strand is a base sequence complementary to a sequence of 16 consecutive bases of the target gene mRNA. More preferably, a sequence of bases at positions 2 to 19 from the 5' end side to the 3' end side of the antisense strand is a base sequence complementary to a sequence of consecutive 18 bases of the target gene mRNA, a sequence of bases at positions 2 to 21 is a base sequence complementary to a sequence of 20 consecutive bases of the target gene mRNA, or a sequence of bases at positions 2 to 25 in a base sequence complementary to a sequence of 24 consecutive bases of the target gene mRNA.

The base sequence at the 5' end of the antisense strand may be complementary to or mismatch the base sequence of the target gene mRNA.

Further, when the nucleic acid used in the present invention is an siRNA, preferably 10 to 70%, more preferably 15 to 60%, further more preferably 20 to 50% of the sugar in the nucleic acid is a 2'-modified nucleotide. The 2'-modified nucleotide of the present invention is preferably 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, 2'-Se-substituted alkyl, or the like, more preferably 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-[2-(N,N-dimethyl)aminooxy]ethyl, 2'-O-[3-(N,N-dimethylamino)propyl], 2'-O-{2-[2-(N,N-dimethylamino)ethoxy]ethyl}, 2'-O-[2-(methylamino)-2-oxoethyl], 2'-Se-methyl, a hydrogen atom, or the like, further preferably 2'-O-methyl, 2'-O-ethyl, 2'-fluoro, a hydrogen atom, or the like, and most preferably 2'-O-methyl and 2'-O-fluoro.

Compound (Ia) corresponds to a nucleotide or a nucleoside in which the residual part of a nucleotide residue or a nucleoside residue represented by formula (I) becomes hydroxy. Examples of the preferred embodiment of Compound (Ia) include an nucleotide or an nucleoside corresponding to the nucleotide residues or the nucleoside residues represented by formula (I) according to the above (2) to (51), and examples of the more preferred embodiment thereof include an nucleotide or an nucleoside corresponding to the nucleotide residue or the nucleoside residue represented by formula (I) wherein $X^1$ is an oxygen atom, $R^2$ is a hydrogen atom, hydroxy, a fluorine atom, or methoxy according to the above (32) to (51).

Compound (Ia) can also be obtained as a salt thereof such as an acid addition salt, a metal salt, an ammonium salt, an organic amine addition salt, an amino acid addition salt, or the like.

Examples of the acid addition salt include an inorganic acid salt such as hydrochloride, sulfate, or phosphate, and an organic acid salt such as acetate, maleate, fumarate, citrate, or methanesulfonate. Examples of the metal salt include an alkali metal salt such as a sodium salt or a potassium salt, an alkaline earth metal salt such as a magnesium salt or a calcium salt, an aluminum salt, a zinc salt, and the like. Examples of the ammonium salt include a salt of ammonium, tetramethylammonium, and the like. Examples of the organic amine addition salt include an addition salt of morpholine, piperidine, and the like. Examples of the amino acid addition salt include an addition salt of lysine, glycine, phenylalanine, and the like.

Among Compounds (Ia), some compounds can exist as a stereoisomer such as a geometric isomer or an optical isomer, a tautomer, and the like. All possible isomers and mixtures thereof inclusive of these isomers can be used in the present invention.

Further, Compound (Ia) can exist in the form of an adduct with water or various solvents, and these adducts can also be used in the present invention.

Examples of the amidite of Compound (Ia) include Compound (B) in the below-described production method for an oligonucleotide, and the like.

Next, a production method for an oligonucleotide of the present invention is described.

A general synthetic method for an oligonucleotide comprises, for example, a step such as an amidation of a nucleotide, an oligomerization (including a step of deprotection or the like), a duplication by annealing (as needed), or the like.

The oligonucleotide of the present invention can be produced by, for example, the following production method.

(1) General Example of Oligomerization

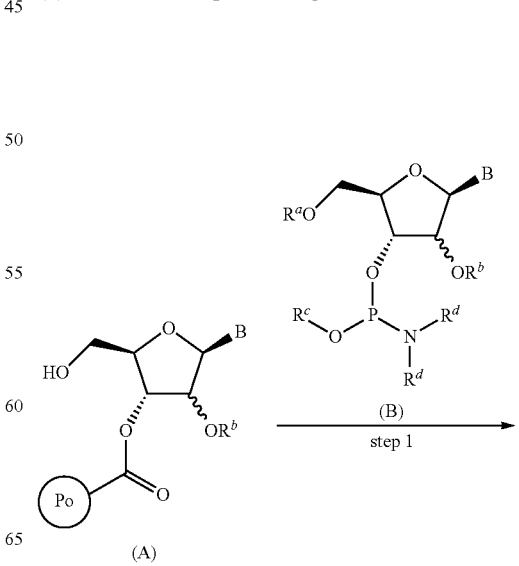

-continued

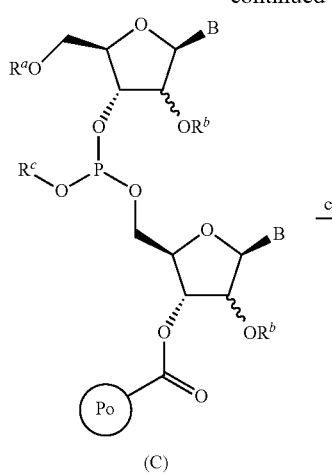

(C)

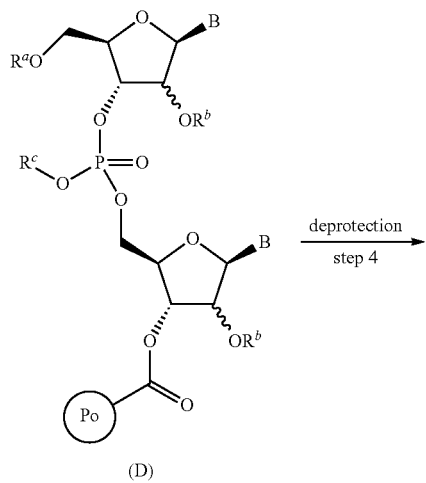

(D)

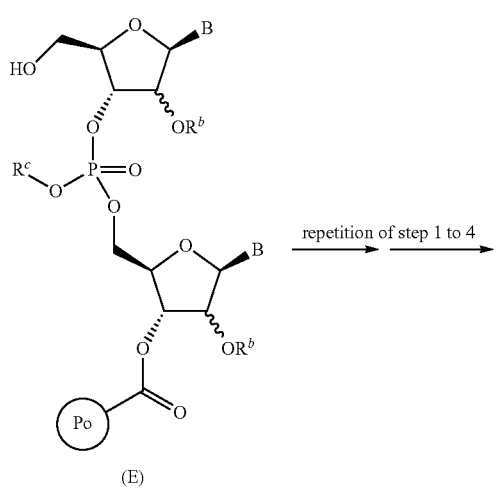

(E)

capping
step 2 oxidation
step 3 deprotection
step 4 repetition of step 1 to 4

-continued

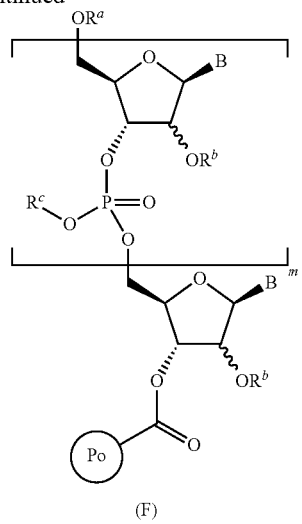

(F)

[wherein n is an integer of, for example, 9 to 99, Po is a solid-phase support such as CPG (controlled pore glass) or the like, $R^a$ is a protecting group which can be removed by an acid treatment such as trityl, p,p'-dimethoxytrityl, or the like, $R^b$ is a protecting group which can be removed with a fluoride ion such as tert-butyldimethylsilyl or the like, $R^c$ is a protecting group which can be removed by a base treatment such as 2-cyanoethyl or the like, $R^d$ is optionally substituted lower alkyl, and B is a nucleobase (the nucleobase may be protected by one or more protecting groups as needed, and in the case where the number of the protecting groups is 2 or more, the respective protecting groups may be the same or different). In the case where m is 2 or more, B's in number of m+1, $R^b$'s in number of m+1, and $R^c$'s in number of m may be the same or different, respectively, and $R^a$'s in the respective stages may be the same or different. Here, the lower alkyl has the same meaning as described above, and the substituent of the optionally substituted lower alkyl has the same meaning as that of the optionally substituted lower alkyl described above.]

Step 1

Compound (C) can be produced by reacting Compound (A) with Compound (B) in a solvent in the presence of a reaction accelerator at a temperature between 0° C. and 50° C. for 10 seconds to 30 minutes.

Examples of the solvent include dichloromethane, acetonitrile, toluene, ethyl acetate, tetrahydrofuran (THF), 1,4-dioxane, N,N-dimethylformamide (DMF), N-methylpyrrolidone (NMP), water, and the like. These can be used alone or as a mixture thereof.

Examples of the reaction accelerator include 1H-tetrazole, 4,5-dicyanoimidazole, 5-ethylthiotetrazole, 5-benzylthiotetrazole, and the like.

Compound (A) can be obtained as, for example, a commercially available product.

Compound (B) can be produced by, for example, the following method.

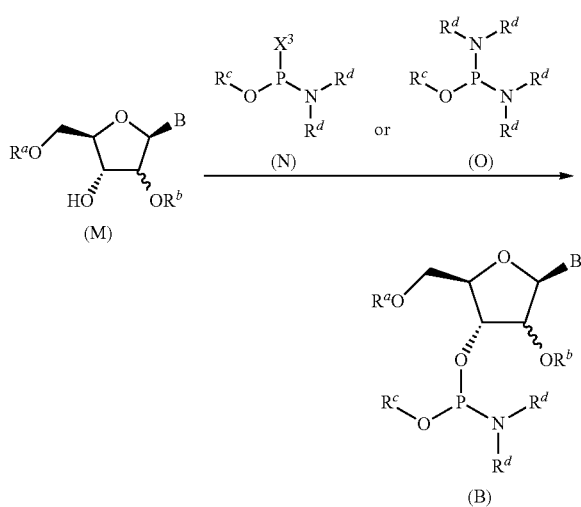

(wherein $R^a$, $R^b$, $R^c$, $R^d$, and B have the same meanings as described above, respectively, and $X^3$ is halogen. The halogen has the same meaning as described above.)

Compound (B) can be produced by reacting Compound (M) with Compound (N) in a solvent in the presence of a base at a temperature between 0° C. and 100° C. for 10 seconds to 24 hours.

Examples of the solvent include dichloromethane, acetonitrile, toluene, ethyl acetate, THF, 1,4-dioxane, DMF, NMP, and the like. These can be used alone or as a mixture thereof.

Examples of the base include triethylamine, N,N-diisopropylethylamine, pyridine, and the like. These can be used alone or as a mixture thereof.

Further, Compound (B) can also be produced by reacting Compound (M) with Compound (O) in a solvent in the presence of a reaction accelerator at a temperature between 0° C. and 100° C. for 10 seconds to 24 hours.

Examples of the solvent include acetonitrile, THF, and the like. These can be used alone or as a mixture thereof.

Examples of the reaction accelerator include those described above.

Step 2

In Step 1, unreacted Compound (A) can be capped by reacting with an acylation reagent in a solvent in the presence of a base at a temperature between 0° C. and 50° C. for 10 seconds to 30 minutes. At this time, the reaction can also be accelerated by adding a suitable additive.

Examples of the acylation reagent include acetic anhydride.

Examples of the solvent include dichloromethane, acetonitrile, ethyl acetate, THF, 1,4-dioxane, DMF, and the like. These can be used alone or as a mixture thereof.

Examples of the base include pyridine, 2,6-lutidine, and the like.

Examples of the additive include 4-dimethylaminopyridine, 1-methylimidazole, and the like.

Step 3

Compound (D) can be produced by reacting Compound (C) with an oxidizing agent in a solvent in the presence of a base at a temperature between 0° C. and 50° C. for 10 seconds to 30 minutes.

Examples of the oxidizing agent include iodine, an aqueous hydrogen peroxide solution, m-chloroperoxybenzoic acid, peracetic acid, tert-butyl hydroperoxide, and the like. These can be used alone or as a mixture thereof.

Examples of the base and the solvent include those described in the above Step 2, respectively.

Step 4

Compound (E) can be produced by reacting Compound (D) with an acid in a solvent at a temperature between 0° C. and 50° C. for 10 seconds to 30 minutes.

Examples of the acid include dichloroacetic acid, trichloroacetic acid, trifluoroacetic acid, and the like.

Examples of the solvent include dichloromethane, chloroform, and the like.

Steps 1 to 4, and the following Steps 5 and 6 can also be performed by using a nucleic acid synthesizer.

(2) General Example of Introduction of Nucleotide Residue (I) at 5' End

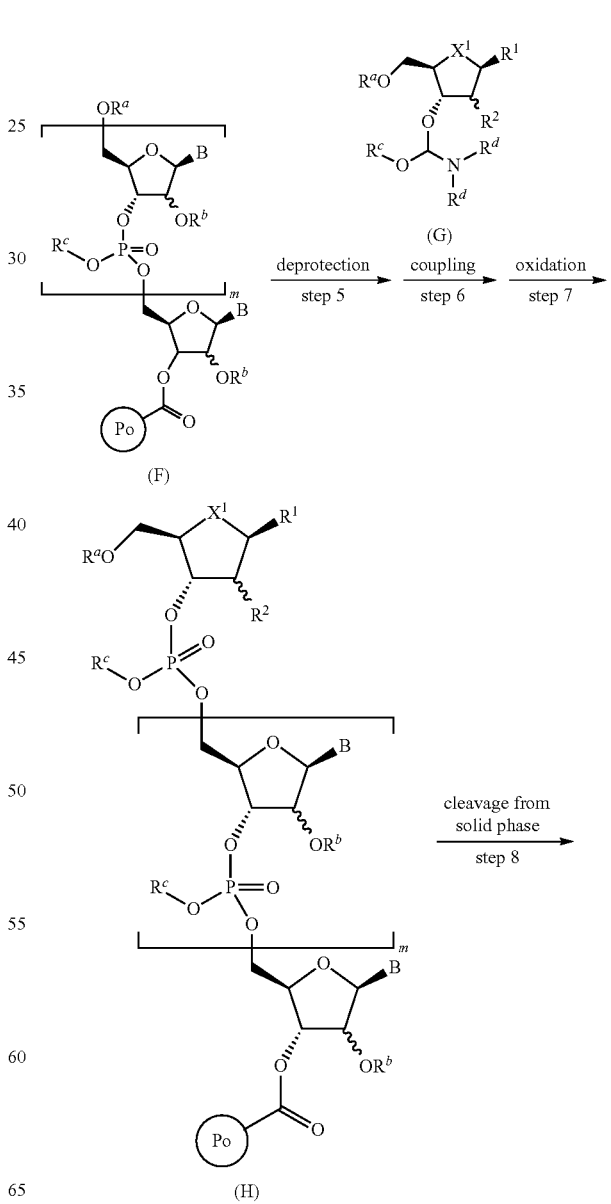

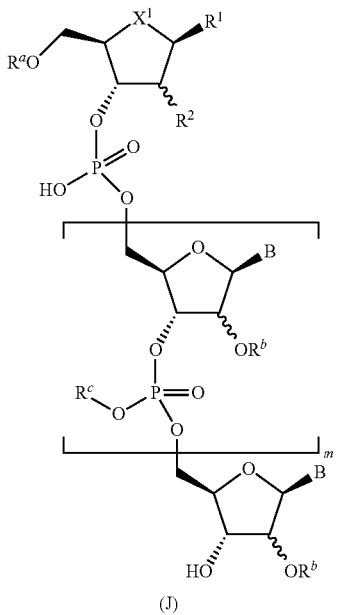

(J)

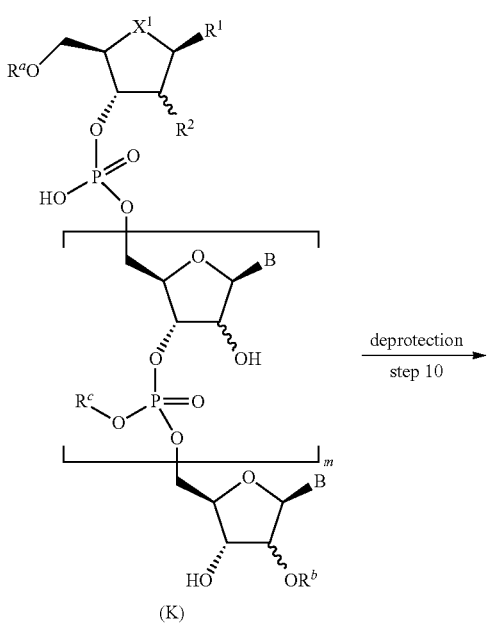

(K)

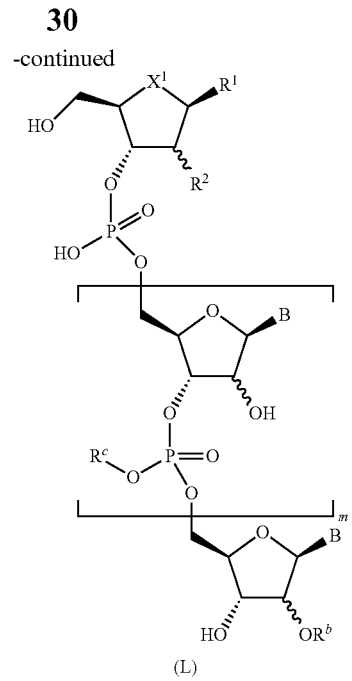

(L)

(wherein m, $X^1$, $R^1$, $R^2$, Po, $R^a$, $R^b$, $R^c$, and $R^d$ have the same meanings Step 5

Step 5 (deprotection of the protecting group $R^a$ of Compound (F)) can be performed in the same manner as the above-described Step 4.

Step 6

Coupling of Compound (F) in which $R^a$ is deprotected in Step 5 (hereinafter referred to as Compound (Fa)) with Compound (C) can be performed by, for example, the following method.

It can be produced by reacting Compound (Fa) with 1 equivalent to a large excess amount of Compound G in a solvent in the presence of a reaction accelerator at a temperature between 0° C. and 50° C. for 10 seconds to 30 minutes.

Examples of the solvent include dichloromethane, acetonitrile, toluene, ethyl acetate, THF, 1,4-dioxan, DMF, NMP, water, and the like. These can be used alone or as a mixture thereof.

Examples of the reaction accelerator include those described above.

Compound G can be obtained as, for example, a commercially available product.

Step 7

Compound (H) can be obtained in the same manner as in the above-described Step 3 (oxidation of a phosphorus atom).

Step 8

It can be cleaved from the solid phase by treating with a base to an oligonucleotide supported on a solid phase, the oligonucleotide can be cleaved from the solid phase. That is, Compound (J) can be produced by treating Compound (H) with a base in a solvent at a temperature between −80° C. and 200° C. for 10 seconds to 72 hours.

Examples of the base include ammonia, methylamine, dimethylamine, ethylamine, diethylamine, 1,8-diazabicyclo [5.4.0]-7-undecene (DBU), and the like.

Examples of the solvent include water, methanol, ethanol, and the like.

Incidentally, in this step, deprotection of the protecting group for a nitrogen atom contained in B (nucleobase) is also performed simultaneously.

Step 9

Compound (K) can be produced by reacting Compound (J) with a fluorine reagent in a solvent at a temperature between −80° C. and 200° C. for 10 seconds to 72 hours. At this time, it is also possible to add a base.

Examples of the fluorine reagent include hydrogen fluoride, triethylamine hydrofluoride, tetrabutylammonium fluoride (TBAF), and the like.

Examples of the base include triethylamine, N,N-diisopropylethylamine, and the like.

Examples of the solvent include dichloromethane, chloroform, acetonitrile, toluene, ethyl acetate, THF, 1,4-dioxane, DMF, N,N-dimethylacetamide (DMA), NMP, dimethyl sulfoxide (DMSO), and the like.

Step 10

Compound (L) can be produced by treating Compound (K) with an acid in a solvent or in a column at a temperature between 0° C. and 50° C. for 5 minutes to 100 hours.

Examples of the acid include trifluoroacetic acid and the like.

Examples of the solvent include water, methanol, ethanol, acetonitrile, and the like. These can be used alone or as a mixture thereof.

Examples of the column include a C18 reverse-phase cartridge column and the like.

(3) General Example of Production of Double-Stranded Oligonucleotide

After Compound (L) is reacted with an equimolar amount of a single-stranded oligonucleotide in a solvent at a temperature between 30° C. and 120° C. for 10 seconds to 72 hours, the reaction mixture is gradually cooled to room temperature over 10 minutes to 24 hours, whereby a double-stranded oligonucleotide can be produced.

Examples of the solvent include an acetate buffer, Tris buffer, a citrate buffer, a phosphate buffer, water, and the like. These can be used alone or as a mixture thereof.

The single-stranded oligonucleotide reacted with Compound (L) in an oligonucleotide complementary to Compound (L), but may contain one or more mismatched base pairs. Further, the base length thereof may be different.

In the above-described scheme, by variously changing the nucleobases, the reaction conditions in the respective steps, and the like, a desirable oligonucleotide can be obtained.

These can be performed according to the method described in, for example, (i) Tetrahedron, vol. 48 No. 12, pp. 2223-2311 (1992);

(ii) Current Protocols in Nucleic Acids Chemistry, John Wiley & Sons (2000);

(iii) Protocols for Oligonucleotides and Analogs, Human Press (1993);

(iv) Chemistry and Biology of Artificial Nucleic Acids, Wiley-VCH (2012);

(v) Genome Chemistry, Scientific Approach Using Artificial Nucleic Acids, Kodansha Ltd. (2003);

(vi) New Trend of Nucleic Acid Chemistry, Kagaku-Dojin Publishing Company, Inc. (2011); or the like.

(4) General Method for Producing Nucleotide or Nucleoside Corresponding to Nucleotide Residue or Nucleoside Residue Represented by Formula (I)

Hereinafter, a general method for producing a nucleotide or a nucleoside corresponding to a nucleotide residue or a nucleoside residue represented by formula (I) is described.

However, the method for producing a nucleotide residue or a nucleoside residue used in the present invention is not limited thereto.

In the production method described below, in the case where the defined group changes under the conditions for the production method or is not suitable for performing the production method, by using a method for introducing and removing a protecting group conventionally used in organic synthetic chemistry [for example, Protective Groups in Organic Synthesis, fourth edition, T. W. Greene, John Wiley & Sons, Inc. (2006), or the like] or the like, a target compound can be produced. Further, it is also possible to change the order of the reaction steps for introducing a substituent and the like as needed.

Production Method 4-1

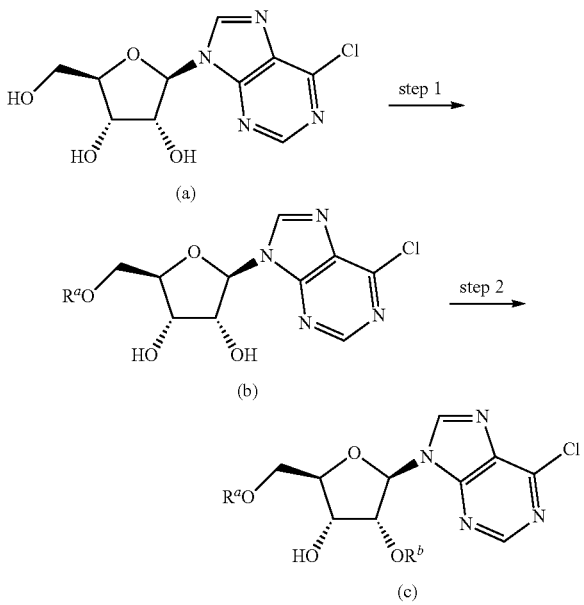

(wherein $R^a$ and $R^b$ have the same meanings as described above, respectively.)

Step 1

Compound (b) can be produced by reacting Compound (a) with a corresponding alkylating agent in a solvent in the presence of a base at a temperature between 0° C. and 150° C. for 10 minutes to 3 days. The reaction can also be accelerated by a suitable activating agent.

Examples of the solvent include DMF, pyridine, dichloromethane, THF, ethyl acetate, 1,4-dioxane, NMP, and the like. These can be used alone or as a mixture thereof.

Examples of the base include pyridine, triethylamine, N-ethyl-N,N-diisopropylamine, 2,6-lutidine, and the like.

Examples of the alkylating agent include trityl chloride, p,p'-dimethoxytrityl chloride, and the like.

Examples of the activating agent include 4-dimethylaminopyridine and the like.

Compound (a) can be synthesized by, for example, a known method [Journal of Medicinal Chemistry, 2004, 47(6), 1987-1996].

Step 2

Compound (c) can be produced by reacting Compound (b) with a silylating agent in a solvent in the presence of a silver salt and a base at a temperature between 0° C. and 80° C. for 10 minutes to 3 days.

Examples of the solvent include THF, ethylene glycol dimethyl ether (DME), and the like. These can be used alone or as a mixture thereof.

Examples of the silver salt include silver nitrate, silver perchlorate, and the like.

Examples of the base include triethylamine, 1,4-diazabicyclo[2,2,2]octane (DABCO), pyridine, and the like.

Examples of the silylating agent include tert-butyldimethylsilyl chloride and the like.

Production Method 4-2

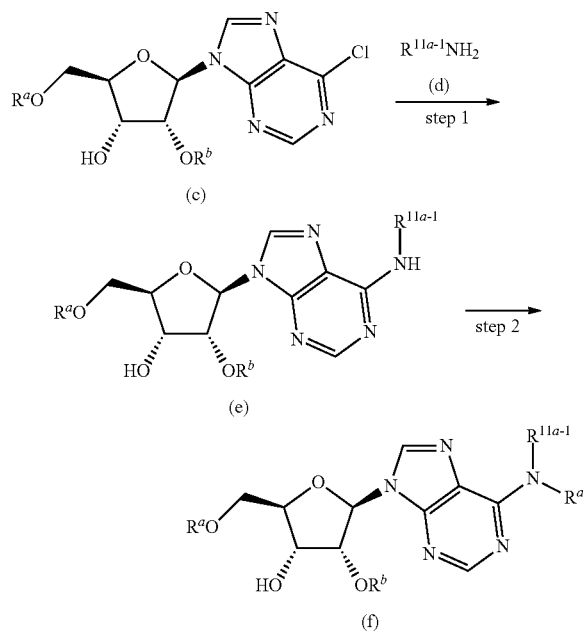

(wherein $R^a$ and $R^b$ have the same meanings as described above, respectively, $R^e$ is a protecting group which can be removed with a base, for example, acetyl, benzoyl, or the like, and $R^{11a-1}$ is optionally substituted lower alkyl, optionally substituted lower alkenyl, optionally substituted lower alkynyl, optionally substituted aryl, optionally substituted aralkyl, optionally substituted aromatic heterocyclic alkyl, or an optionally substituted aromatic heterocyclic group in the definition of $R^{11a}$ described above.)

Step 1

Compound (e) can be produced by reacting Compound (c) with Compound (d) in a solvent or without a solvent in the presence or absence of a base at a temperature between 0° C. and 150° C. for 1 hour to 1 week.

Examples of the solvent include DMF, pyridine, dichloromethane, THF, ethyl acetate, NMP, acetonitrile, and the like. These can be used alone or as a mixture thereof.

Examples of the base include triethylamine, N-ethyl-N, N-diisopropylamine, and the like.

Step 2

Compound (f) can be produced by reacting Compound (e) with a silylating agent in a solvent at a temperature between 0° C. and 100° C. for 10 minutes to 3 hours, and then, by react ing the resulting product with an acylating agent at a temperature between 0° C. and 100° C. for 1 hour to 72 hours, and by further treating the resulting product with water or an alcohol for 1 hour to 24 hours. The reaction can also be accelerated by allowing a suitable activating agent to coexist with the acylating agent.

Examples of the solvent include pyridine and the like.

Examples of the silylating agent include trimethylsilyl chloride, trifluoromethanesulfonyl trimethylsilyl, N,O-bis(trimethylsilyl) acetamide, 1,1,1,3,3,3-hexamethyldisilazane, and the like.

Examples of the acylating agent include acetic anhydride, acetyl chloride, benzoyl chloride, and the like.

Examples of the alcohol include methanol, ethanol, 1-propanol, and the like.

Examples of the activating agent include 4-dimethylaminopyridine.

Production Method 4-3

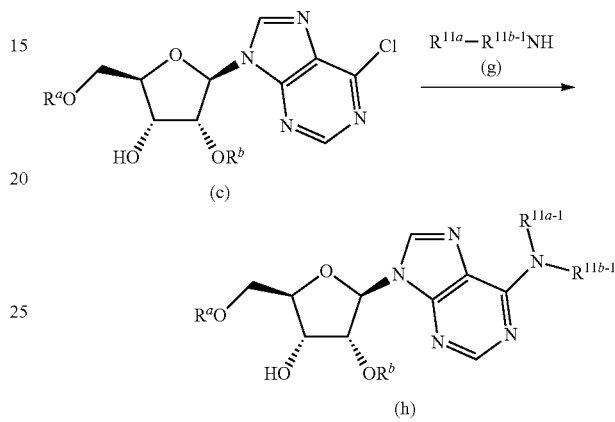

(wherein $R^a$, $R^b$, and $R^{11a-1}$ have the same meanings as described above, respectively, and $R^{11b-1}$ is optionally substituted lower alkyl, optionally substituted lower alkenyl, optionally substituted lower alkynyl, optionally substituted aryl, optionally substituted aralkyl, optionally substituted aromatic heterocyclic alkyl, or an optionally substituted aromatic heterocyclic group in the definition of $R^{11b}$ described above.)

Compound (h) can be produced by reacting Compound (c) with Compound (g) in a solvent or without a solvent in the presence or absence of a base at a temperature between 0° C. and 150° C. for 1 hour to 1 week.

Examples of the solvent include DMF, pyridine, dichloromethane, THF, ethyl acetate, NMP, acetonitrile, and the like. These can be used alone or as a mixture thereof.

Examples of the base include triethylamine, N-ethyl-N, N-diisopropylamine, and the like.

Production Method 4-4

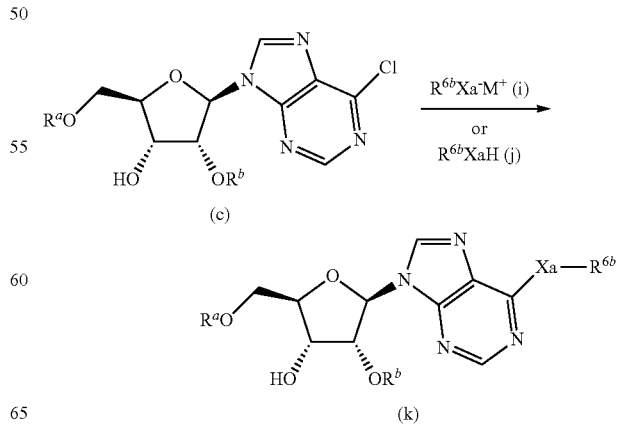

(wherein $R^a$ and $R^b$ have the same meanings as described above, respectively, $R^{6b}$ is optionally substituted lower alkyl, optionally substituted aryl, or an optionally substituted aromatic heterocyclic group, Xa is an oxygen atom or a sulfur atom, and M is an alkali metal atom. Here, the lower alkyl, the aryl, and the aromatic heterocyclic group have the same meanings as described above, respectively, the substituent of the optionally substituted lower alkyl has the same meaning as the substituent of the optionally substituted lower alkyl described above, and the substituents of the optionally substituted aryl and the optionally substituted aromatic heterocyclic group have the same meanings as the substituents of the optionally substituted aryl and the optionally substituted aromatic heterocyclic group described above, respectively. The alkali metal atom is a lithium atom, a sodium atom, or a potassium atom.)

Compound (k) can be produced by reacting Compound (c) with Compound (l) in a solvent at a temperature between 0° C. and 100° C. for 10 minutes to 3 days, or by reacting Compound (c) with Compound (j) in a solvent in the presence of a base at a temperature between 0° C. and 120° C. for 10 minutes to 3 days.

Examples of the solvent include methanol, ethanol, 2-propanol, THF, DME, DMF, NMP, and the like. These can be used alone or as a mixture thereof.

Examples of the base include sodium hydroxide, potassium hydroxide, sodium carbonate, potassium carbonate, sodium hydride, potassium hydride, tert-butoxy potassium, and the like.

Production Method 4-5

120° C. for 30 minutes to 72 hours. The reaction can also be accelerated by adding a suitable phosphine.

Compound (l) can be obtained as a commercially available product or according to a known method [for example, Synthesis of Organic Compound VI, organic synthesis using metal, Jikken Kagaku Koza (Encyclopedia of Experimental Chemistry) 18, 5th Ed., p. 97, Maruzen (2005)] or a method according to that.

Examples of the base include potassium carbonate, potassium phosphate, potassium hydroxide, sodium hydroxide, potassium tert-butoxide, triethylamine, diisopropylethylamine, N-methylmorpholine, pyridine, DBU, and the like.

Examples of the palladium catalyst include palladium acetate, tris (dibenzylideneacetone)dipalladium, tetrakis(triphenylphosphine)palladium, 1,1'-bis(diphenylphosphino) ferrocenedichloropalladium/dichloromethane (1:1) adduct, and the like.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, water, and the like. These can be used alone or as a mixture thereof.

Examples of the suitable phosphine include 1,2-bis(diphenylphosphino)ethane, 1,3-bis(diphenylphosphino)propane, 4,5'-bis(diphenylphosphino)-9,9'-dimethylxanthene (Xantphos), 2,2'-bis(diphenylphosphino)-1,1'-binaphthyl (BINAP), and the like.

Production Method 4-6

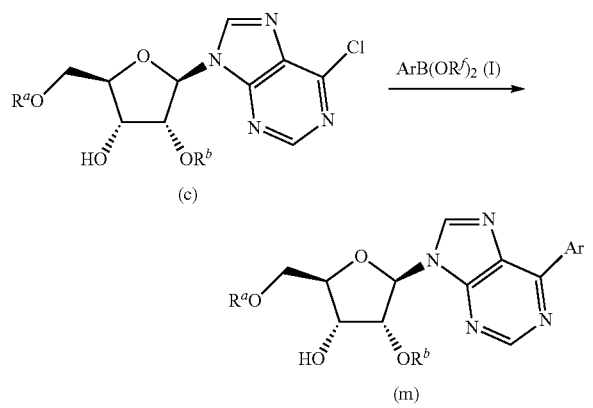

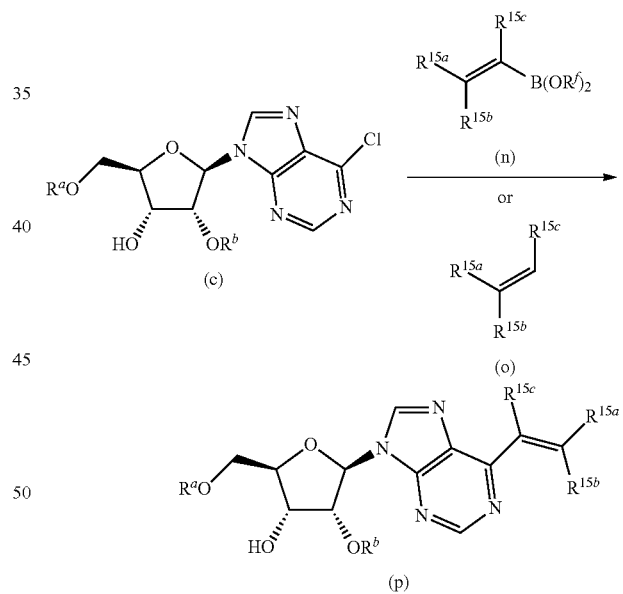

(wherein $R^a$ and $R^b$ have the same meanings as described above, respectively, Ar is optionally substituted aryl or au optionally substituted aromatic heterocyclic group, and $R^f$ is a hydrogen atom or optionally substituted lower alkyl. Here, the lower alkyl, the aryl, and the aromatic heterocyclic group have the same meanings as described above, respectively, the substituent of the optionally substituted lower alkyl has the same meaning as the substituent of the optionally substituted lower alkyl described above, and the substituents of the optionally substituted aryl and the optionally substituted aromatic heterocyclic group have the same meanings as the substituents of the optionally substituted aryl and the optionally substituted aromatic heterocyclic group described above, respectively.)

Compound (m) can be produced by reacting Compound (c) with Compound (l) in a solvent in the presence of a base and a palladium catalyst at a temperature between 0° C. and (wherein $R^a$, $R^b$, and $R^f$ have the same meanings as described above, respectively. Each of $R^{15a}$, $R^{15b}$, and $R^{15c}$ is a hydrogen atom, optionally substituted lower alkyl, aryl, or an aromatic heterocyclic group. Here, the lower alkyl, the aryl, and the aromatic heterocyclic group have the same meanings as described above, respectively, and the substituent of the optionally substituted lower alkyl has the same meaning as the substituent of the optionally substituted lower alkyl described above.)

Compound (p) can be produced by reacting Compound (c) with Compound (n) in a solvent in the presence of a base and a palladium catalyst at a temperature between 0° C. and 120° C. for 30 minutes to 72 hours. The reaction can also be accelerated by adding a suitable phosphine.

Compound (n) can be obtained as, for example, a commercially available product.

Examples of the base include potassium carbonate, potassium phosphate, potassium hydroxide, sodium hydroxide, potassium tert-butoxide, triethylamine, diisopropylethylamine, N-methylmorpholine, pyridine, DBU, and the like.

Examples of the palladium catalyst include those described above.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, water, and the like. These can be used alone or as a mixture thereof.

Further, Compound (p) can also be produced by reacting Compound (c) with Compound (o) in a solvent in the presence of a base and a palladium catalyst at a temperature between 0° C. and 140° C. for 30 minutes to 72 hours.

Examples of the base include potassium acetate, sodium hydrogen carbonate, potassium carbonate, potassium hydroxide, sodium hydroxide, sodium methoxide, potassium tert-butoxide, triethylamine, diisopropylethylamine, N-methylmorpholine, pyridine, DBU, and the like.

Examples of the palladium catalyst include those described above.

Examples of the solvent include dichloromethane, chloroform, 1,2-dichloroethane, toluene, ethyl acetate, acetonitrile, diethyl ether, THF, DME, dioxane, DMF, DMA, NMP, and the like. These can be used alone or as a mixture thereof.

Examples of the suitable phosphine include 1,2-bis(diphenylphosphino)ethane, 1,3-bis(diphenylphosphino) propane, Xantphos, BINAP, and the like.

Production Method 4-7

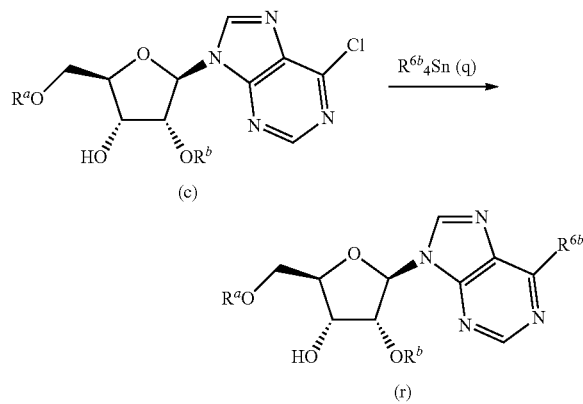

(wherein $R^a$, $R^b$, and $R^{6b}$ have the same meanings as described above, respectively.)

Compound (r) can be produced by reacting Compound (c) with Compound (q) in a solvent in the presence of a palladium catalyst at a temperature between 0° C. and 150° C. The reaction can also be accelerated by adding a suitable additive and/or a suitable phosphine.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, and the like. These can be used alone or as a mixture thereof.

Compound (q) can be obtained as, for example, a commercially available product.

Examples of the palladium catalyst include those described above.

Examples of the suitable additive include lithium chloride, cesium fluoride, and the like.

Examples of the suitable phosphine include 1,2-bis(diphenylphosphino)ethane, 1,3-bis(diphenylphosphino)propane, Xantphos, BINAP, and the like.

Production Method 4-8

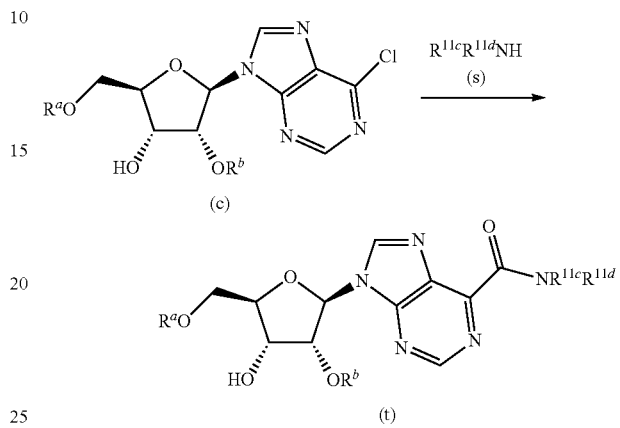

(wherein $R^a$, $R^b$, $R^{11c}$, and $R^{11d}$ have the same meanings as described above, respectively.)

Compound (t) can be produced by reacting Compound (c) with Compound (s) in a solvent under a carbon monoxide atmosphere in the presence of a base and a palladium catalyst at a temperature between room temperature and 120° C. for 1 hour to 72 hours. The reaction can also be accelerated by adding a suitable phosphine.

Examples of the solvent include dichloromethane, chloroform, 1,2-dichloroethane, toluene, ethyl acetate, acetonitrile, diethyl ether, THF, DME, dioxane, DMF, DMA, NMP, and the like. These can be used alone or as a mixture thereof.

Examples of the base include sodium acetate, potassium acetate, sodium hydrogen carbonate, potassium carbonate, sodium methoxide, potassium tert-butoxide, triethylamine, diisopropylethylamine, N-methylmorpholine, pyridine, DBU, and the like.

Examples of the palladium catalyst include those described above.

Examples of the phosphine include 1,2-bis(diphenylphosphino) ethane, 1,3-bis(diphenylphosphino)propane, Xantphos, BINAP, and the like.

Production Method 4-9

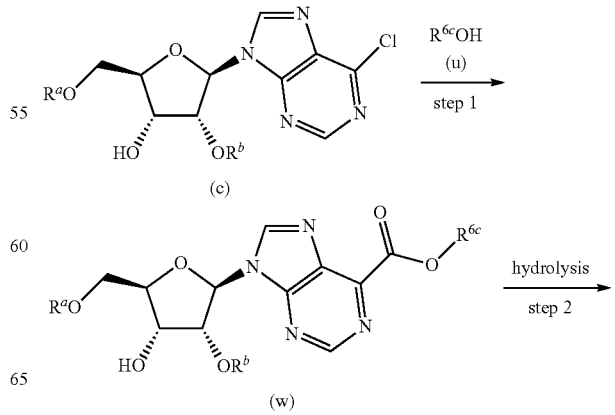

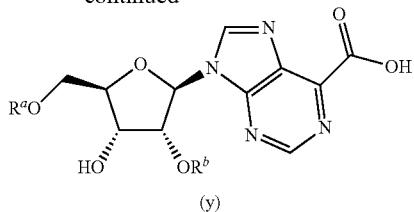

(y)

(wherein $R^a$ and $R^b$ have the same meanings as described above, respectively, and $R^{6c}$ is optionally substituted lower alkyl, optionally substituted aryl, or an optionally substituted aromatic heterocyclic group. Here, the lower alkyl, the aryl, and the aromatic heterocyclic group have the same meanings as described above, respectively, the substituent of the optionally substituted lower alkyl has the same meaning as the substituent of the optionally substituted lower alkyl described above, and the substituents of the optionally substituted aryl and the optionally substituted aromatic heterocyclic group have the same meanings as the substituents of the optionally substituted aryl and the optionally substituted aromatic heterocyclic group described above, respectively.)

Step 1

Compound (w) can be produced by reacting Compound (c) with Compound (u) in a solvent under a carbon monoxide atmosphere in the presence of a base and a palladium catalyst at a temperature between room temperature and 120° C. for 1 hour to 72 hours. The reaction can also be accelerated by adding a suitable phosphine.

Examples of the solvent include methanol, ethanol, 1-propanol, 2-propanol, 1-butanol, tert-butyl alcohol, dichloromethane, chloroform, 1,2-dichloroethane, toluene, ethyl acetate, acetonitrile, diethyl ether, THF, DME, dioxane, DMF, DMA, NMP, and the like. These can be used alone or as a mixture thereof.

Examples of the base include sodium acetate, potassium acetate, sodium hydrogen carbonate, potassium carbonate, sodium methoxide, potassium tert-butoxide, triethylamine, diisopropylethyl amine, N-methylmorpholine, pyridine, DBU, and the like.

Examples of the palladium catalyst include those described above.

Examples of the phosphine include 1,2-bis(diphenylphosphino)ethane, 1,3-bis(diphenylphosphino)propane, Xantphos, BINAP, and the like.

Step 2

Compound (y) can be produced by treating Compound (w) in a solvent in the presence of a base at a temperature between 0° C. and 100° C. for 5 minutes to 72 hours.

Examples of the base include potassium carbonate, lithium hydroxide, potassium hydroxide, sodium hydroxide, sodium methoxide, and the like.

Examples of the solvent include a solvent containing water, and examples of the solvent include methanol, ethanol, dichloromethane, chloroform, 1,2 dichloroethane, toluene, ethyl acetate, acetonitrile, diethyl ether, THF, DME, dioxane, DMF, DMA, NMP, pyridine, and the like. Those are used by mixing with water or by mixing with one another and then adding water thereto.

Production Method 4-10

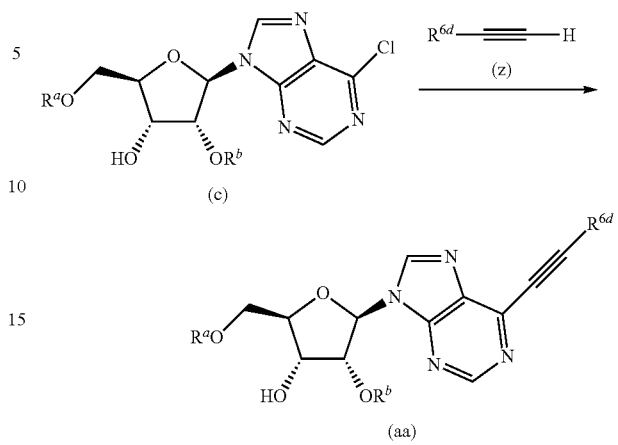

(wherein $R^a$ and $R^b$ have the same meanings as described above, respectively, and $R^{6d}$ is optionally substituted lower alkyl, aryl, or an aromatic heterocyclic group. Here, the lower alkyl, the aryl, and the aromatic heterocyclic group have the same meanings as described above, respectively, and the substituent of the optionally substituted lower alkyl has the same meaning as the substituent of the optionally substituted lower alkyl described above.)

Compound (aa) can be produced by reacting Compound (c) with Compound (z) in a solvent in the presence of a copper salt, a base, and a palladium catalyst at a temperature between room temperature and 150° C. for 1 hour to 72 hours. The reaction can also be accelerated by adding a suitable phosphine.

Examples of the solvent include dichloromethane, chloroform, 1,2-dichloroethane, toluene, ethyl acetate, acetonitrile, diethyl ether, THF, DME, dioxane, DMF, DMA, NMP, and the like. These can be used alone or as a mixture thereof.

Examples of the copper salt include copper(I) iodide and the like.

Examples of the base include sodium acetate, potassium acetate, sodium hydrogen carbonate, potassium carbonate, sodium methoxide, potassium tert-butoxide, triethylamine, diisopropylethylamine, N-methylmorpholine, pyridine, DBU, and the like.

Examples of the palladium catalyst include those described above.

Examples of the phosphine include 1,2-bis(diphenylphosphino) ethane, 1,3-bis(diphenylphosphino)propane, Xantphos, BINAP, and the like.

Production Method 4-11

By using Compound as obtained by the following method, a nucleoside used as a starting material for the production of the oligonucleotide of the present invention can be obtained according to the above-described production methods 4-2 to 4-10.

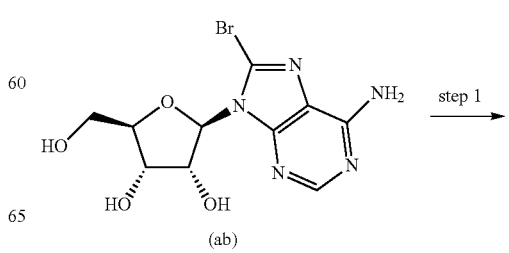

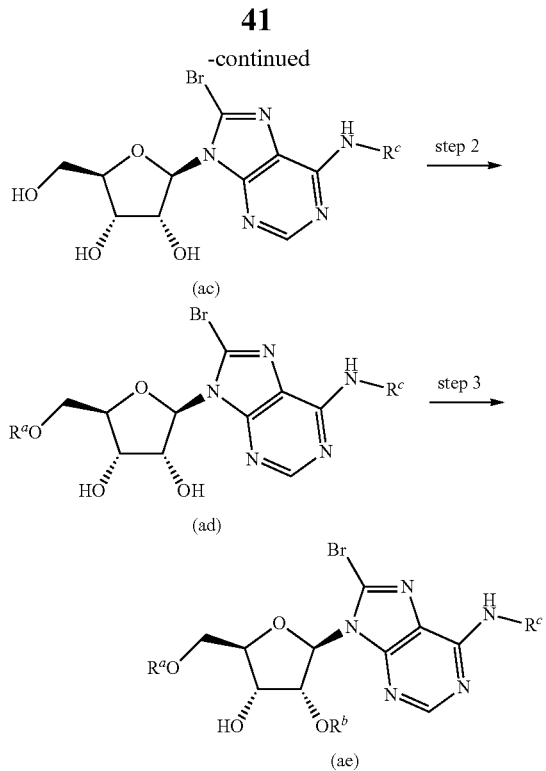

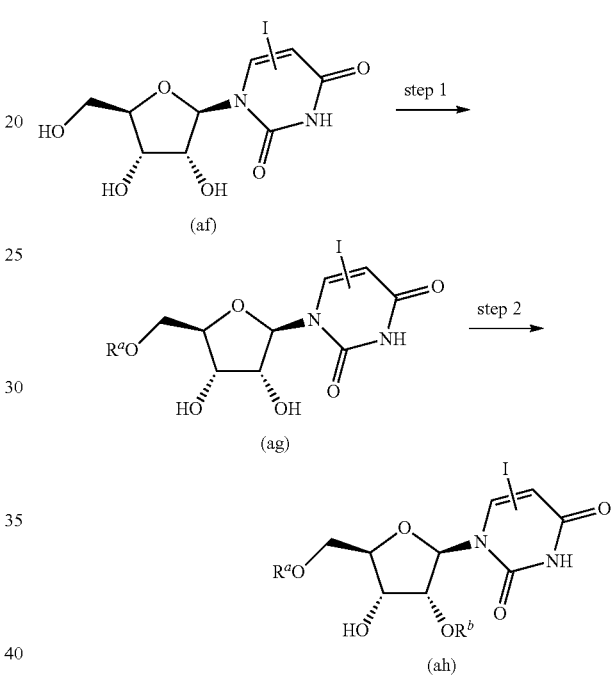

(wherein $R^a$, $R^b$, and $R^c$ have the same meanings as described above, respectively.)

Step 1

Compound (ac) can be produced by reacting Compound (ab) with a silylating agent in a solvent at a temperature between 0° C. and 100° C. for 10 minutes to 3 hours, and then, by reacting with an acylating agent at a temperature between 0° C. and 100° C. for 1 hour to 72 hours, and by further treating with water or an alcohol for 1 hour to 24 hours.

Examples of the solvent include pyridine and the like.

Examples of the silylating agent include trimethylsilyl chloride, trifluoromethanesulfonyl trimethylsilyl, N,O-bis(trimethylsilyl)acetamide, 1,1,1,3,3,3-hexamethyldisilazane, and the like.

Examples of the acylating agent include acetic anhydride, acetyl chloride, benzoyl chloride, and the like.

Examples of the alcohol include methanol, ethanol, 1-propanol, and the like.

Compound (ab) can be synthesized by, for example, a known method [Tetrahedron, 1970, 26, 4251-4259].

Step 2

Compound (ad) can be produced by reacting Compound (ac) with a corresponding alkylating agent in a solvent in the presence of a base at a temperature between 0° C. and 150° C. for 10 minutes to 3 days. The reaction can also be accelerated by a suitable activating agent.

Examples of the solvent include DMF, pyridine, dichloromethane, THF, ethyl acetate, 1,4-dioxane, NMP, and the like. These can be used alone or as a mixture thereof.

Examples of the base include pyridine, triethylamine, N-ethyl-N,N-diisopropylamine, 2,6-lutidine, and the like.

Examples of the alkylating agent include trityl chloride, p,p'-dimethoxytrityl chloride, and the like.

Examples of the activating agent include 4-dimethylaminopyridine and the like.

Step 3

Compound (ae) can be produced by reacting Compound (ad) with a silylating agent in a solvent in the presence of a silver salt and a base at a temperature between 0° C. and 80° C. for 10 minutes to 3 days.

Examples of the solvent include THF, DME, and the like. These can be used alone or as a mixture thereof.

Examples of the silver salt include silver nitrate, silver perchlorate, and the like.

Examples of the base include triethylamine, DABCO, pyridine, and the like.

Examples of the silylating agent include tert-butyldimethylsilyl chloride and the like.

Production Method 4-12

(wherein $R^a$ and $R^b$ have the same meanings as described above, respectively.)

Step 1

Compound (ag) can be produced by reacting Compound (af) with a corresponding alkylating agent in a solvent in the presence of a base at a temperature between 0° C. and 150° C. for 10 minutes to 3 days. The reaction can also be accelerated by a suitable activating agent.

Examples of the solvent include DMF, pyridine, dichloromethane, THF, ethyl acetate, 1,4-dioxane, NMP, and the like. These can be used alone or as a mixture thereof.

Examples of the base include pyridine, triethylamine. N-ethyl-N,N-diisopropylamine, 2,6-lutidine, and the like.

Examples of the alkylating agent include trityl chloride, p,p'-dimethoxytrityl chloride, and the like.

Examples of the activating agent include 4-dimethylaminopyridine and the like.

Compound (af) can be synthesized by, for example, a known method (Journal of Medicinal Chemistry, 2004, 50 (5), 915-921 and WO2011/51733).

Step 2

Compound (ah) can be produced by reacting Compound (ag) with a silylating agent in a solvent in the presence of a silver salt and a base at a temperature between 0° C. and 80° C. for 10 minutes to 3 days.

Examples of the solvent include THF, DME, and the like. These can be used alone or as a mixture thereof.

Examples of the silver salt include silver nitrate, silver perchlorate, and the like.

Examples of the base include triethylamine, DABCO, pyridine, and the like.

Examples of the silylating agent include tert-butyldimethylsilyl chloride and the like.

Production Method 4-13

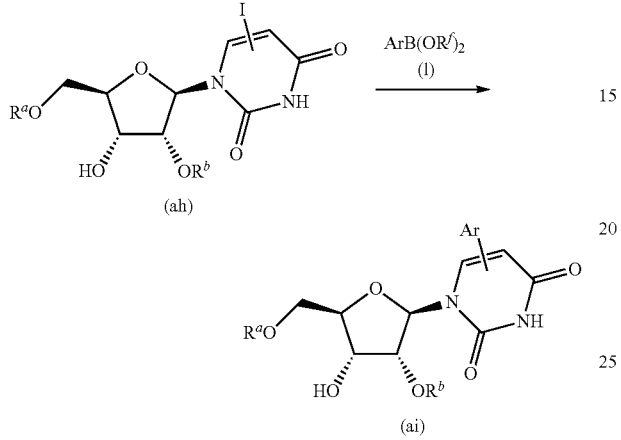

(wherein $R^a$, $R^b$, $R^f$, and Ar have the same meanings as described above, respectively.)

Compound (ai) can be produced according to the production method 4-5 using Compound (ah).

Production Method 4-14

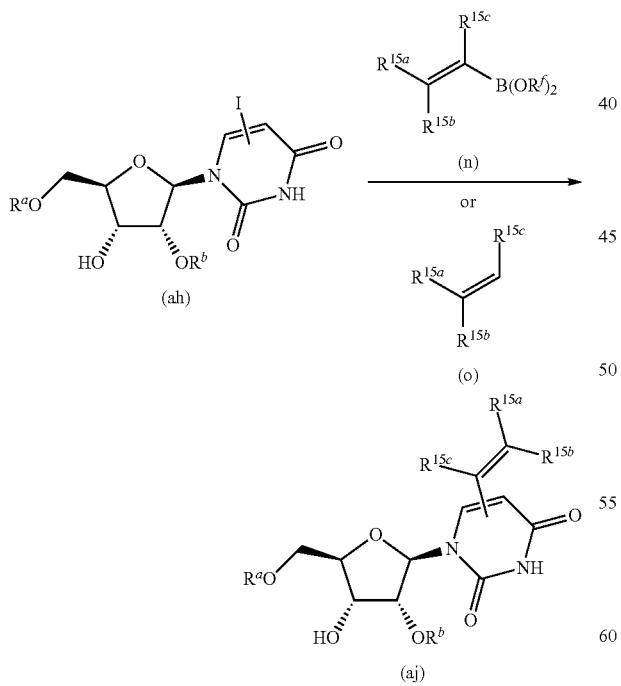

(wherein $R^a$, $R^b$, $R^f$, $R^{15a}$, $R^{15b}$, and $R^{15c}$ have the same meanings as described above, respectively.)

Compound (aj) can be produced according to the production method 4-6 using Compound (ah).

Production Method 4-15

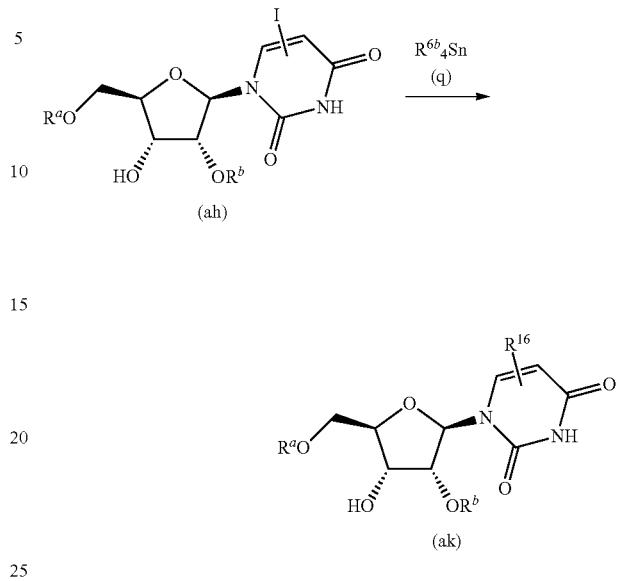

(wherein $R^a$, $R^b$, and $R^{6b}$ have the same meanings as described above, respectively.)

Compound (ak) can be produced according to the production method 4-7 using Compound (ah).

Production Method 4-16

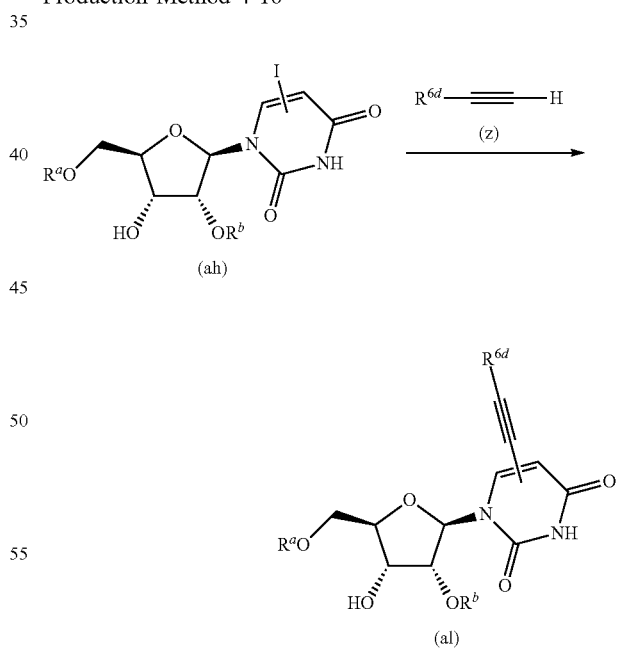

(wherein $R^a$, $R^b$, and $R^{6d}$ have the same meanings as described above, respectively.)

Compound (al) can be produced according to the production method 4-10 using Compound (ah).

Production Method 4-17

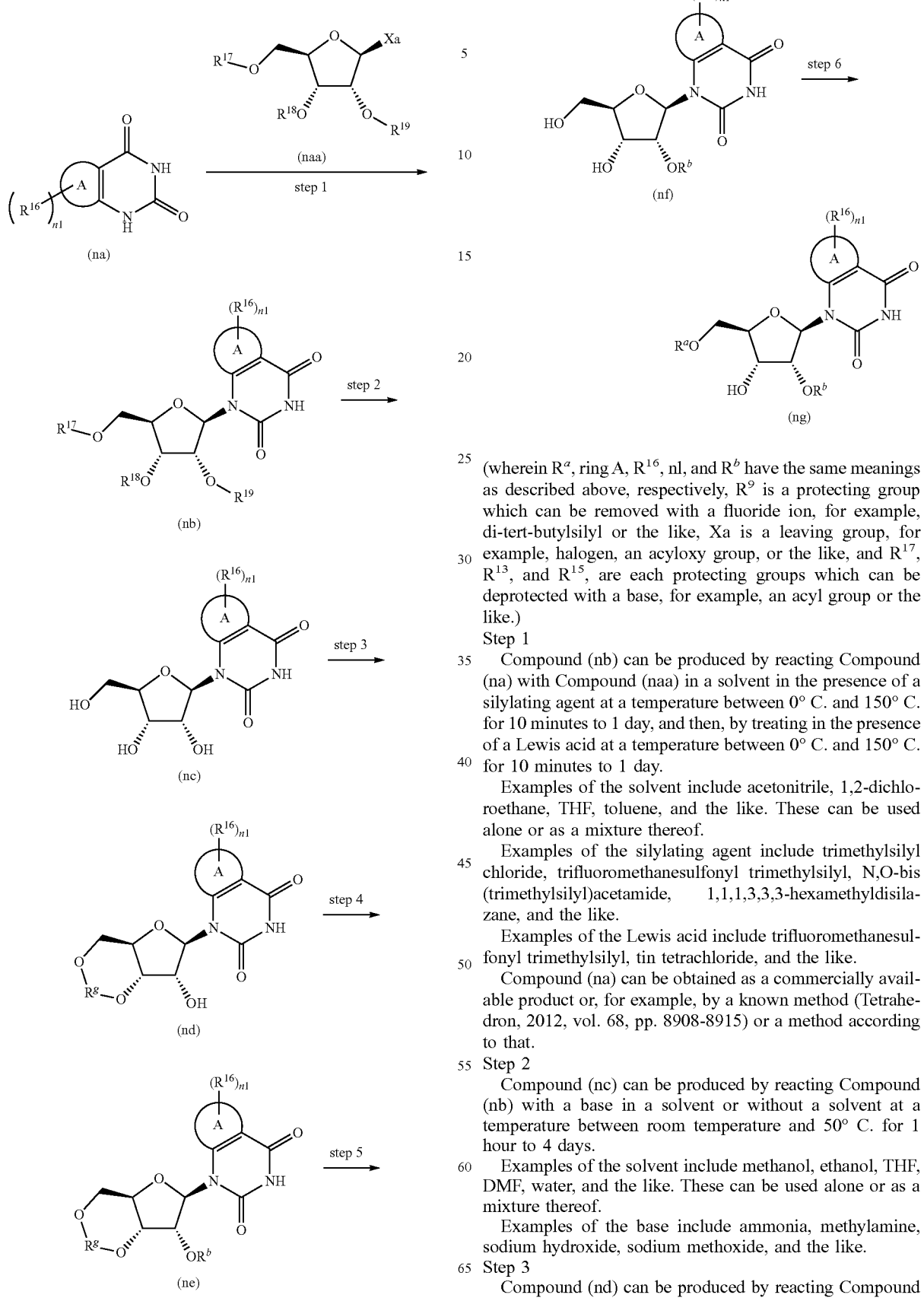

(wherein $R^a$, ring A, $R^{16}$, nl, and $R^b$ have the same meanings as described above, respectively, $R^9$ is a protecting group which can be removed with a fluoride ion, for example, di-tert-butylsilyl or the like, Xa is a leaving group, for example, halogen, an acyloxy group, or the like, and $R^{17}$, $R^{13}$, and $R^{15}$, are each protecting groups which can be deprotected with a base, for example, an acyl group or the like.)

Step 1

Compound (nb) can be produced by reacting Compound (na) with Compound (naa) in a solvent in the presence of a silylating agent at a temperature between 0° C. and 150° C. for 10 minutes to 1 day, and then, by treating in the presence of a Lewis acid at a temperature between 0° C. and 150° C. for 10 minutes to 1 day.

Examples of the solvent include acetonitrile, 1,2-dichloroethane, THF, toluene, and the like. These can be used alone or as a mixture thereof.

Examples of the silylating agent include trimethylsilyl chloride, trifluoromethanesulfonyl trimethylsilyl, N,O-bis(trimethylsilyl)acetamide, 1,1,1,3,3,3-hexamethyldisilazane, and the like.

Examples of the Lewis acid include trifluoromethanesulfonyl trimethylsilyl, tin tetrachloride, and the like.

Compound (na) can be obtained as a commercially available product or, for example, by a known method (Tetrahedron, 2012, vol. 68, pp. 8908-8915) or a method according to that.

Step 2

Compound (nc) can be produced by reacting Compound (nb) with a base in a solvent or without a solvent at a temperature between room temperature and 50° C. for 1 hour to 4 days.

Examples of the solvent include methanol, ethanol, THF, DMF, water, and the like. These can be used alone or as a mixture thereof.

Examples of the base include ammonia, methylamine, sodium hydroxide, sodium methoxide, and the like.

Step 3

Compound (nd) can be produced by reacting Compound (nc) with, for example, a corresponding silylating agent in a solvent in the presence of a base at a temperature between 0° C. and 80° C. for 10 minutes to 3 days.

Examples of the solvent include DMF, DMA, NMP, and the like. These can be used alone or as a mixture thereof.

Examples of the base include imidazole, triethylamine, diisopropylethylamine, and the like.

Examples of the silylating agent include di-tert-butylsilyl bis(trifluoromethanesulfonate) and the like.

Step 4

Compound (ne) can be produced by reacting Compound (nd) with, for example, a corresponding silylating agent in a solvent in the presence of a base at a temperature between 0° C. and 80° C. for 10 minutes to 3 days.

Examples of the solvent include dichloromethane, chloroform, 1,2-dichloroethane, DMF, and the like. These can be used alone or as a mixture thereof.

Examples of the base include imidazole, triethylamine, diisopropylethylamine, and the like.

Examples of the silylating agent include tert-butyldimethylsilyl chloride and the like.

Step 5

Compound (nf) can be produced by treating Compound (ne) with a deprotecting reagent in a solvent in the presence of a base at a temperature between 0° C. and 80° C. for 10 minutes to 3 days.

Examples of the solvent include dichloromethane, chloroform, 1,2-dichloroethane, diethyl ether, THF, DME, dioxane, and the like. These can be used alone or as a mixture thereof.

Examples of the base include triethylamine, diisopropylethylamine, pyridine, and the like.

Examples of the deprotecting reagent include hydrogen fluoride-pyridine and the like.

Step 6

Compound (ng) can be produced by reacting Compound (nf) with a corresponding alkylating agent in a solvent in the presence of a base at a temperature between 0° C. and 150° C. for 10 minutes to 3 days. The reaction can also be accelerated by a suitable activating agent.

Examples of the solvent include dichloromethane, chloroform, 1,2-dichloroethane, THF, dioxane, DMF, pyridine, and the like. These can be used alone or as a mixture thereof.

Examples of the base include triethylamine, diisopropylethylamine, pyridine, and the like.

Examples of the alkylating agent include trityl, chloride, p,p'-dimethoxytrityl chloride, and the like.

Examples of the activating agent include 4-dimethylaminopyridine and the like.

The transformation of each group in the compounds included in the above-described respective production methods can also be performed by a known method [for example, Comprehensive Organic Transformations 2nd edition, R. C. Larock, vch Verlagsgesellscaft Mbh, 1999, or the like] or a method according to those.

A desired nucleotide or nucleoside can be obtained by performing deprotection and phosphorylation of hydroxy of the product obtained by the above-described respective production methods according to a known method [for example, Journal of Medicinal Chemistry, vol. 55, pp. 1478-1489, 2012, or the like].

The intermediate and the target compound in the above-described respective production methods can be isolated and purified by a separation and purification method conventionally used in organic synthetic chemistry, for example, filtration, extraction, washing, drying, concentration, recrystallization, various types of chromatography, or the like.

Further, the intermediate can also be subjected to the subsequent reaction particularly without further purification.

The nucleotide or nucleoside above can also be obtained in the form of a salt such as an acid addition salt, a metal salt, an ammonium salt, an organic amine addition salt, an amino acid addition salt, or the like.

Examples of the acid addition salt include an inorganic acid salt such as hydrochloride, sulfate, or phosphate, and an organic acid salt such as acetate, maleate, fumarate, citrate, or methanesulfonate. Examples of the metal salt include an alkali metal salt such as a sodium salt or a potassium salt, an alkaline earth metal salt such as a magnesium salt or a calcium salt, an aluminum salt, a zinc salt, and the like. Examples of the ammonium salt include a salt of ammonium, tetramethylammonium, or the like. Examples of the organic amine addition salt include an addition salt of morpholine, piperidine, or the like. Examples of the amino acid addition salt include a lysine addition salt, a glycine addition salt, a phenylalanine addition salt, and the like.

If it is desirable to obtain a salt of the nucleotide or the nucleoside above, when the nucleotide or the nucleoside is obtained in the form of a salt, it may be directly purified. Further, when the nucleotide or the nucleoside is obtained in a free form, the nucleotide or the nucleoside may be dissolved or suspended in a suitable solvent, followed by addition of an acid or a base. Then, the resulting salt may be isolated and purified.

Among the nucleotides or the nucleosides above, some nucleotides or nucleosides can exist as a stereoisomer such as a geometric isomer or a optical isomer, a tautomer, or the like. All possible isomers inclusive of these stereoisomers and tautomers and mixtures thereof can be used in the present invention.

Further, the nucleotide or the nucleoside above can exist in the form of an adduct with water or various solvents, and these adducts can also be used in the present invention.

Specific examples of Compound (Ia) are shown in Tables 1 to 7. It should be noted, however, that Compound (Ia) of the present invention and the corresponding nucleotide residue or nucleoside residue represented by formula (I) are not limited to these and the corresponding nucleotide residue or nucleoside residue.

TABLE 1

| Compound No. | structural formula |
|---|---|
| I-1 (8-Br-dA) | [structure of 8-Br-dA nucleotide] |
| I-2 (8-oxo-dA) | [structure of 8-oxo-dA nucleotide] |

TABLE 1-continued

| Compound No. | structural formula |
|---|---|
| I-3 (8-Br-dU) | (structure) |
| I-4 (5-F-dU) | (structure) |
| I-5 reference example 1 | (structure) |
| I-6 reference example 2 | (structure) |
| I-7 reference example 3 | (structure) |

TABLE 2

| compound No. | structural formula |
|---|---|
| I-8 reference example 4 | (structure) |
| I-9 reference example 5 | (structure) |

TABLE 2-continued
| compound No. | structural formula |
|---|---|
| I-10 reference example 6 | 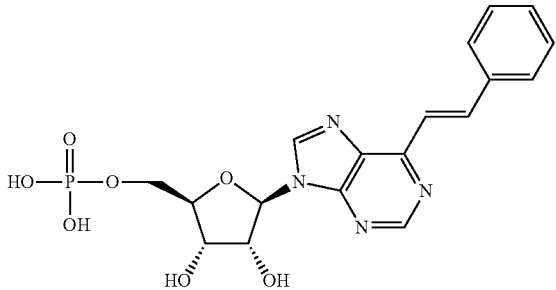 [SMILES: O=P(O)(O)OC[C@H]1O[C@@H](n2cnc3c(/C=C/c4ccccc4)ncnc32)[C@H](O)[C@@H]1O] |
| I-11 reference example 7 | 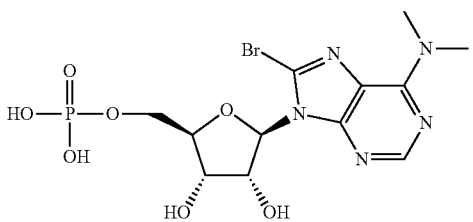 [SMILES: CN(C)c1ncnc2c1nc(Br)n2[C@@H]1O[C@H](COP(=O)(O)O)[C@@H](O)[C@H]1O] |
| I-12 reference example 8 | 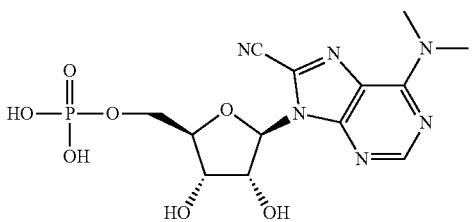 |
| I-13 reference example 9 | 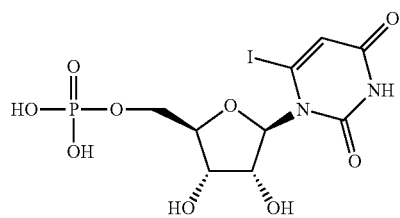 [SMILES: O=c1cc(I)n([C@@H]2O[C@H](COP(=O)(O)O)[C@@H](O)[C@H]2O)c(=O)[nH]1] |
| I-14 reference example 10 | 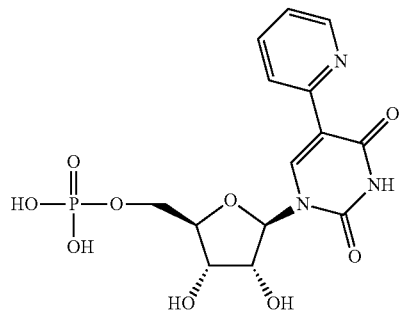 [SMILES: O=c1[nH]c(=O)n([C@@H]2O[C@H](COP(=O)(O)O)[C@@H](O)[C@H]2O)cc1-c1ccccn1] |

TABLE 3
| compound No. | structural formula |
|---|---|
| I-15 reference example 11 | 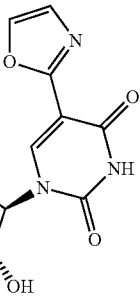 |
| I-16 reference example 12 | 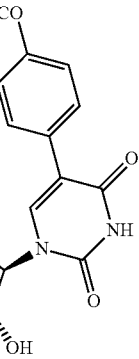 |
| I-17 reference example 13 | 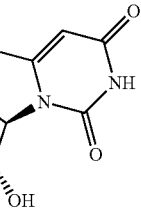 |
| I-18 reference example 14 | 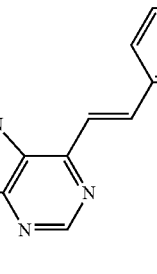 |
TABLE 4
| compound No. | structural formula |
|---|---|
| I-19 reference example 15 | 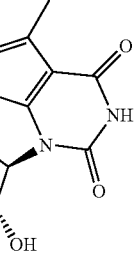 |

TABLE 4-continued
| compound No. | structural formula |
|---|---|
| I-20 reference example 16 | 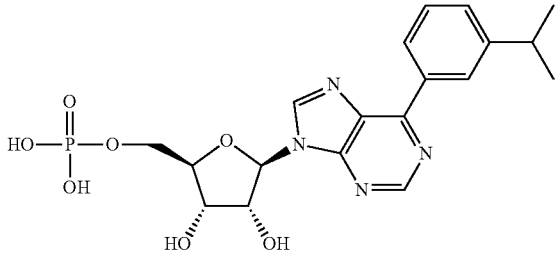 [SMILES: CC(C)c1cccc(-c2ncnc3c2ncn3[C@@H]2O[C@H](COP(=O)(O)O)[C@@H](O)[C@H]2O)c1] |
| I-21 reference example 17 | 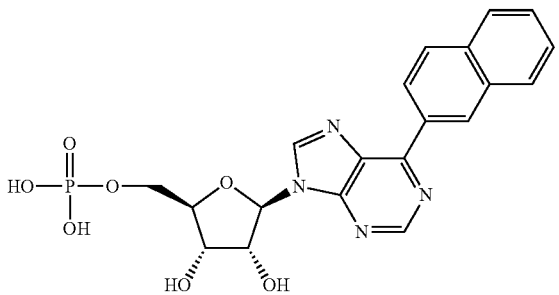 [SMILES: O=P(O)(O)OC[C@H]1O[C@@H](n2cnc3c(-c4ccc5ccccc5c4)ncnc32)[C@H](O)[C@@H]1O] |
| I-22 reference example 18 | 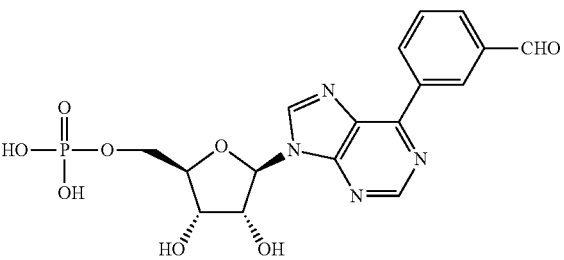 [SMILES: O=Cc1cccc(-c2ncnc3c2ncn3[C@@H]2O[C@H](COP(=O)(O)O)[C@@H](O)[C@H]2O)c1] |
| I-23 reference example 19 | 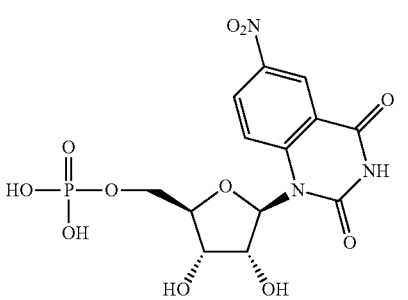 [SMILES: O=c1[nH]c(=O)n([C@@H]2O[C@H](COP(=O)(O)O)[C@@H](O)[C@H]2O)c2ccc([N+](=O)[O-])cc12] |
| I-24 reference example 20 | 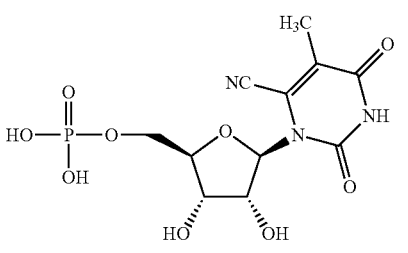 [SMILES: Cc1c(C#N)n([C@@H]2O[C@H](COP(=O)(O)O)[C@@H](O)[C@H]2O)c(=O)[nH]c1=O] |

TABLE 5
| compound No. | structural formula |
| --- | --- |
| I-25 reference example 21 | 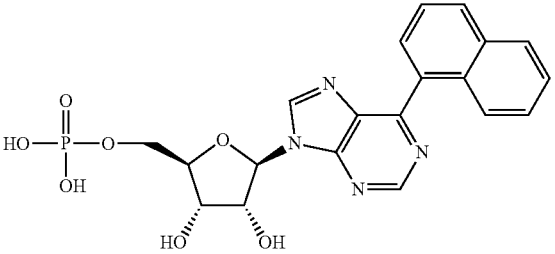 [SMILES: O=P(O)(O)OC[C@H]1O[C@@H](n2cnc3c(-c4cccc5ccccc45)ncnc32)[C@H](O)[C@@H]1O] |
| I-26 reference example 22 | 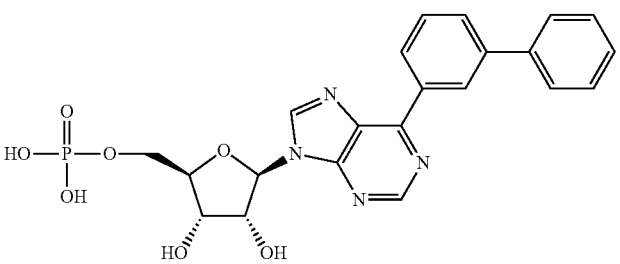 [SMILES: O=P(O)(O)OC[C@H]1O[C@@H](n2cnc3c(-c4cccc(-c5ccccc5)c4)ncnc32)[C@H](O)[C@@H]1O] |
| I-27 reference example 23 | 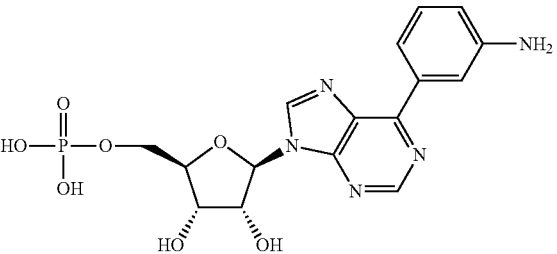 [SMILES: Nc1cccc(-c2ncnc3c2ncn3[C@@H]2O[C@H](COP(=O)(O)O)[C@@H](O)[C@H]2O)c1] |
| I-28 reference example 24 | 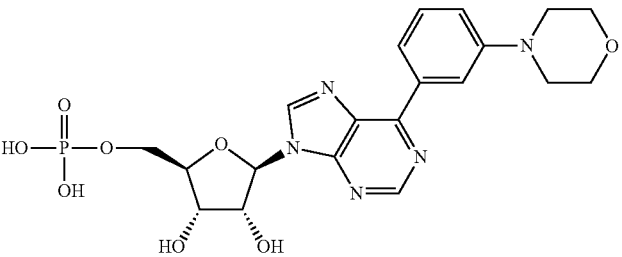 [SMILES: O=P(O)(O)OC[C@H]1O[C@@H](n2cnc3c(-c4cccc(N5CCOCC5)c4)ncnc32)[C@H](O)[C@@H]1O] |
| I-29 reference example 25 | 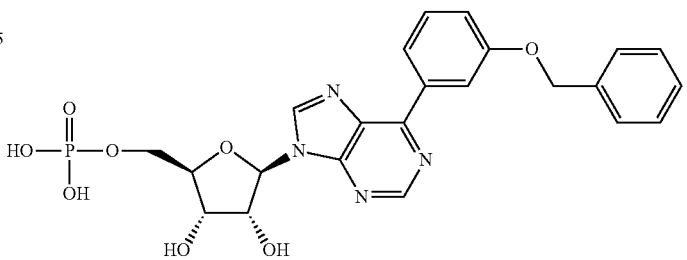 [SMILES: O=P(O)(O)OC[C@H]1O[C@@H](n2cnc3c(-c4cccc(OCc5ccccc5)c4)ncnc32)[C@H](O)[C@@H]1O] |
| I-30 reference example 26 | 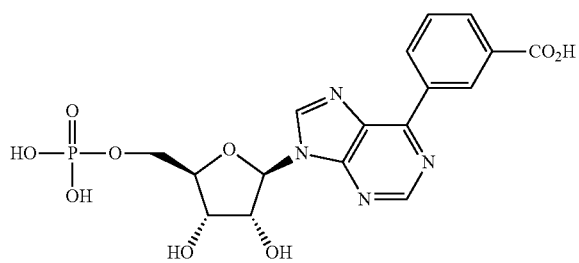 [SMILES: O=C(O)c1cccc(-c2ncnc3c2ncn3[C@@H]2O[C@H](COP(=O)(O)O)[C@@H](O)[C@H]2O)c1] |

TABLE 6

| compound No. | structural formula |
|---|---|
| I-31 reference example 27 | 5-styryl uridine 5′-monophosphate |
| I-32 reference example 28 | 6-styryl-2′-O-methyl adenosine 5′-monophosphate |
| I-33 reference example 29 | 5-methyl uridine 5′-monophosphate |
| I-34 reference example 30 | 6-methyl uridine 5′-monophosphate |

TABLE 7

| compound No. | structural formula |
|---|---|
| I-35 reference example 31 | 7-chloro-6-nitroquinazoline-2,4-dione ribonucleoside 5′-monophosphate |

TABLE 7-continued

| compound No. | structural formula |
| --- | --- |
| I-36<br>reference example 32 | (structure shown) |
| I-37<br>reference example 33 | (structure shown) |
| I-38<br>reference example 34 | (structure shown) |

The oligonucleotide of the present invention can be introduced into a cell by using a carrier for transfection, preferably a cationic carrier such as a cationic liposome. Further, it can also be directly introduced into a cell by a calcium phosphate method, an electroporation method, a microinjection method, and the like.

For example, an siRNA can selectively inhibit the expression of any protein through cleavage of an mRNA, and therefore, the application thereof to pharmaceuticals is expected. In an oligonucleotide (for example, an siRNA) having a knockdown activity against an mRNA encoding a protein involved in a disease, by substituting a nucleotide residue or a nucleoside residue at the 5' end of the oligonucleotide with a nucleotide residue or a nucleoside residue represented by formula (I), the knockdown activity against a target mRNA is expected.

Further, in an oligonucleotide (for example, an siRNA) having a knockdown activity against an mRNA encoding a protein involved in a disease, by substituting a base residue at the 5' end of the oligonucleotide with a base residue represented by any of formulae (II) to (V), the affinity of the oligonucleotide for AGO2 is improved and the oligonucleotide has a higher knockdown activity against a target mRNA. Further, in an oligonucleotide in which a base at the 5' end is guanine or cytosine, by substituting the guanine residue or the cytosine residue at the 5' end of the oligonucleotide with an adenine residue (6-aminopurin-9-yl), a thymine residue (5-methyl-1,2,3,4-tetrahydropyrimidine-2, 4-dion-1-yl), an uridine residue (pyrimidin-2,4(1H,3H)-dion-1-yl), or a base residue represented by any of formulae (II) to (V), the affinity of the oligonucleotide for AGO2 is improved and the oligonucleotide has a higher knockdown activity against a target mRNA.

The phosphate moiety at the 5' end or the sugar moiety of the oligonucleotide having a high knockdown activity against a target mRNA obtained according to the present invention may be the same as or different from that of formula (I).

In the present invention, examples of the preferred embodiment of base residues represented by formulae (II) to (V) include base residues represented by formulae (II) to (V) according to the above (4) to (12), (14) to (16), (18) to (22), and (24) to (27), and examples of the more preferred embodiment thereof include base residues represented by formulae (IIA) to (VA) according to the above (34) to (38), (40) to (43), and (45) to (47).

The oligonucleotide of the present invention and the oligonucleotide having a knockdown activity against a target mRNA improved by the method of the present invention can be administered alone as it is. However, usually, it is preferably provided in various pharmaceutical formulations. Further, these pharmaceutical formulations are used for animals and humans.

The pharmaceutical formulations relating to the present invention can contain, as the active ingredient, the oligonucleotide of the present invention alone or as a mixture with any other active ingredient for treatment. Further, these pharmaceutical formulations are prepared by mixing the active ingredient with one or more pharmaceutically acceptable carriers and then produced by any method well known in the technical field of pharmaceutics. Examples of the production method for the pharmaceutical formulation of the present invention include a calcium phosphate method, a DEAE-dextran method, electroporation and microinjection, a virus method, a method using a cationic liposome, and the like (Graham, P. L. and van der Eb, A. J. (1973) Virol. 52, 456; McCutchan, J. H. and Pagano, J. S. (1968) J. Natl. Cancer Inst. 41, 351, Chu, G. et al., (1987) Nucl. Acids Res. 15, 1311, Fraley, R. et al., (1980) J. Biol. Chem. 255, 10431; Capechi, M. R. (1980) Cell, 22, 479, Felgner, P. L. et al., (1987), Proc. Natl. Acad. Sci. USA, 84, 7413).

Further, a method using a nucleic acid-containing cationic lipid particle or cationic polymer, a nucleic acid-encapsulated lipid particle, and the like is included. In addition, modification of the surface of a lipid particle and the like with a water-soluble polymer such as polyethylene glycol (PEG) is generally performed, and also the above-described nucleic acid-containing cationic lipid particle or cationic polymer, nucleic acid-encapsulated lipid particle, and the like described above can be transformed into a PEG-modified lipid particle.

As for the administration route, it is preferred to select the most effective administration route in the treatment. Examples of the administration route include oral administration or parenteral administration such as intravenous administration.

Examples of the dosage form include a tablet, an injection, and the like.

A suitable dosage form for the oral administration, for example, a tablet or the like, can be produced by using an excipient such as lactose, a disintegrator such as starch, a lubricant such as magnesium stearate, a binder such as hydroxypropyl cellulose, and the like.

A suitable dosage form for the parenteral administration, for example, a injection, can be produced by using a salt solution, a glucose solution, or a mixed liquid of a salt solution and a glucose solution, and the like.

The dose and the frequency of administration of the oligonucleotide of the present invention may vary depending upon dosage form, age and body weight of a patient, nature or seriousness of the symptom to be treated, and the like. In general, in the parenteral administration such as intravenous administration a dose of 0.001 to 100 mg, preferably, 0.01 to 10 mg, is administered to an adult once or several times a day. However, these doses and frequencies of administration vary according to the various conditions described above.

Hereinafter, embodiments of the present invention are described with reference to Examples and Reference Examples. Unless otherwise stated, starting materials and reagents used were obtained as commercially available products, or according to known methods. Incidentally, the present invention is not limited to these Examples and Reference Examples.

EXAMPLE 1

The synthesis of luciferase-targeting siRNAs having 8-bromo-2'-deoxyadonosine monophosphate (8-Br-dA) at the 5' end of each of the antisense strands shown in Table 8 (X contained in the sequence of each of the antisense strands denotes 8-Br-dA) were performed on a scale of 0.5 μmol using a nucleic acid synthesizer (Ultra Fast Parallel Synthesizer, Sigma Co., Ltd., hereinafter referred to as UFPS). As a solid-phase support, CPG 500 angstrom, rA.rG(tac), SAFC-PROLIGO was used. Each of DMT-2'-O-TBDMS-rA(tac) amidite (SAFC-PROLIGO), DMT-2'-O-TBDMS-rG (tac) amidite (SAFC-PROLIGO), DMT-2'-O-TBDMS-rC (tac) amidite (SAFC-PROLIGO), and DMT-2'-O-TBDMS-rU amidite (SAFC-PROLIGO) was prepared into a 0.1 mol/L acetonitrile solution, 8-Br-dA-CE phosphoramidite (Glen ResearchCorporation) was prepared into a 0.1 mol/L acetonitrile solution, Chemical Phosphorylation Reagent II (Glen Research Corporation) was prepared into a 0.06 mol/L acetonitrile solution, and these were used for a condensation reaction. As an activating agent of phosphoramidites, 5-benzylthio-1H-tetrazole (SAFC-PROLIGO) was used, and the condensation time was set to 10 minutes in each case. After synthesis in trityl-off mode, it was immersed in a 28% ammonia solution, and the resulting mixture was allowed to stand at 55° C. for 4 hours. After the reaction mixture was concentrated under the reduced pressure, 31% triethylamine trihydrofluoride was added thereto, and the resulting mixture was allowed to stand at 65° C. for 3 hours. Thereafter, 1-butanol was added thereto to stop the reaction. The resulting product was purified by reverse-phase liquid chromatography(SHISEIDO, CAPSELL PAK C18, SG300, 6.0 mm×75 mm, 5% acetonitrile/0.1% triethylammonium acetate buffer, gradient by B solution: 50% acetonitrile/water), whereby a target oligonucleotide was obtained.

The single-stranded oligonucleotide obtained was dissolved in a mixed buffer [100 mmol/L potassium acetate, 30 mmol/L 2-[4-(2-hydroxyethyl)piperazin-1-yl]ethanesulfonic acid (HEPES)-KOH (pH 7.4), and 2 mmol/L magnesium acetate] to give a concentration of 50 μmol/L. Equal amounts of sense and antisense strands were mixed with each other and the resulting mixture was allowed to stand at 80° C. for 10 minutes. The temperature of the mixture was gradually decreased, and the mixture was allowed to stand at 37° C. for 1 hour, whereby a double-stranded oligonucleotide was obtained.

TABLE 8

| | sense strand | | antisense strand | |
| --- | --- | --- | --- | --- |
| | sequence (5'→3') | sequence number | sequence (5'→3') | sequence number |
| 239-BrdA | UGCAGCGAGAAUAGCUUGUAG | 1 | XCAAGCUAUUCUCGCUGCACA | 2 |
| 874-BrdA | UAGCUUCUUCGCUAAGAGUAC | 3 | XCUCUUAGCGAAGAAGCUAAA | 4 |
| 904-BrdA | CAAGUACGACCUAAGCAAUUU | 5 | XUUGCUUAGGUCGUACUUGUC | 6 |
| 1084-BrdA | AGGCAAGGUGGUGCCCUUUUU | 7 | XAAGGGCACCACCUUGCCUAC | 8 |

TEST EXAMPLE 1

RNAi Activity of Luciferase-Targeting siRNA

The RNAi activity of the luciferase-targeting siRNA having 8-Br-dA at the 5' end of the antisense strand obtained in Example 1 was evaluated by using the level of inhibition of luciferase luminescence as an index as described below.

In a culture dish (Assay plate, 96-well, with Lid, Cat. No. 3917, manufactured by Costar Co., Ltd.), human cervical cancer-derived cell line Hela cells (CCL-2, purchased from ATCC) transfected with a luciferase expression vector (pGL4.50 [luc2/CMV/Hygro] Vector, Promega Corporation) were suspended in RPMI medium (Invitrogen Life Technologies, 11875093) containing 10% fetal bovine serum, and the cell suspension was inoculated into each well at 50 µL/well to give 5000 cells/well.

An siRNA was diluted with OPTI-MEM (Invitrogen Life Technologies, 31985-070). Lipofectamine RNAiMAX (Invitrogen Life Technologies, 13778-075) was diluted with OPTI-MEM. These prepared dilute liquids were mixed with each other to form an siRNA-lipofectamine RNAiMAX complex. Ten microliter of a solution of the prepared siRNA-Lipofectamine RNAiMAX (Invitrogen Life Technologies, 13778-075) complex was added to each well containing the cell suspension, so that the siRNA, was introduced into the Hela cells. The final concentration of the siRNA was set to one level: 100 pmol/L, or the following four levels: 3.2 pmol/L, 16 pmol/L, 80 pmol/L, and 400 pmol/L, and N was set to 6. Further, as a negative control group, cells to which only Lipofectamine RNAiMAX was added were inoculated. Further, for comparison, a test was performed in the same manner also for siRNAs having adenosine monophosphate at a posit ion corresponding to 8-Br-dA of each siRNA (referred to as 239-A, 874-A, 904-A, 1084-A, 1203-A, and 1556-A, respectively, shown in Table 9). Further, a test was performed in the same manner also for siRNAs having guanosine monophosphate, cytidine monophosphate, or uridine monophosphate at a position corresponding to 8-Br-dA of 874-BrdA (referred to as 874-G, 874-C, and 874-U, respectively, shown in Table 10).

TABLE 9

| | sense strand | | antisense strand | |
|---|---|---|---|---|
| | sequence (5'→3') | sequence number | sequence (5'→3') | sequence number |
| 239-A | UGCAGCGAGAAUAGCUUGUAG | 1 | ACAAGCUAUUCUCGCUGCACA | 13 |
| 874-A | UAGCUUCUUCGCUAAGAGUAC | 3 | ACUCUUAGCGAAGAAGCUAAA | 14 |
| 904-A | CAAGUACGACCUAAGCAAUUU | 5 | AUUGCUUAGGUCGUACUUGUC | 15 |
| 1084-A | AGGCAAGGUGGUGCCCUUUUU | 7 | AAAGGGCACCACCUUGCCUAC | 16 |
| 1203-A | UUAACAACCCCGAGGCUAUAA | 9 | AUAGCCUCGGGGUUGUUAACG | 17 |
| 1556-A | GACGAGGUGCCUAAAGGAUUG | 11 | AUCCUUUAGGCACCUCGUCCA | 18 |

TABLE 10

| | sense strand | | antisense strand | |
|---|---|---|---|---|
| | sequence (5'→3') | sequence number | sequence (5'→3') | sequence number |
| 874-G | UAGCUUCUUCGCUAAGAGCAC | 19 | GCUCUUAGCGAAGAAGCUAAA | 20 |
| 874-C | UAGCUUCUUCGCUAAGAGGAC | 21 | CCUCUUAGCGAAGAAGCUAAA | 22 |
| 874-U | UAGCUUCUUCGCUAAGAGAAC | 23 | UCUCUUAGCGAAGAAGCUAAA | 24 |

The cells after introduction of each of the siRNAs were cultured under the conditions at 37° C. and 5% $CO_2$ far 24 hours.

To the cells after culture, 40 µL of Steady-Glo Luciferase Assay System (Promega E2520), which is a commercially available luciferase assay reagent, was added to each well according to the attached protocol. After the cells were incubated for 1.0 minutes, the amount of luminescence (cps) per second in each well was measured using ARVO (PerkinElmer) according to the protocol.

By also performing the measurement of the amount of luminescence in the negative control group simultaneously with the measurement of the amount of luminescence in the luciferase-targeting siRNA treated group, the RNAi effect on each of the siRNA-introduced samples was expressed as a relative ratio when the amount of luminescence in the siRNA-unintroduced group (negative control group) was taken as 1.

The results of this test are shown in FIGS. 1 and 2. FIG. 1 is a graph showing comparison between the siRNA of the present invention and the siRNA having adenosine monophosphate at a position corresponding to 8-Br-dA in the sequence thereof at a final concentration of 100 pmol/L. FIG. 2 is a graph showing comparison between 874-BrdA, which is the siRNA of the present invention, and 874-A, 874-G, 874-C, and 874-U having adenosine monophosphate, guanosine monophosphate, cytidine monophosphate, or uridine monophosphate at a position corresponding to 8-Br-dA in the sequence thereof at final concentrations of 3.2 pmol/L, 16 pmol/L, 80 pmol/L, and 400 pmol/L (in FIGS. 1 and 2, the ordinate represents the ratio of the amount of luminescence when the amount of luminescence in the negative control group was taken as 1). Additionally, by the Kruskal-Wallis test, it was determined whether or not there is a significant difference. In the statistical analysis, statistical analysis software SAS (Release 9.2, SAS Institute, Inc.) was used. In Table 11, the results of the significant difference test for comparison between the ratio of inhibition of luminescence by 239-BrdA, 874-BrdA, 904-BrdA, 1084-BrdA, 1203-BrdA, and 1556-BrdA and the ratio of inhibition of luminescence by 239-A, 874-A, 904-A, 1084-A, 1203-A, and 1556-A, respectively, are shown. A p-value of 0.05 or less was obtained in all the cases, and it is found that the ratio of inhibition of luminescence was significantly improved in the case of the siRNA in which adenosine monophosphate was substituted with 8-Br-dA.

TABLE 11

| | 239-BrdA | 874-BrdA | 904-BrdA | 1084-BrdA | 1203-BrdA | 1566-BrdA |
|---|---|---|---|---|---|---|
| p | 0.01 | 0.004 | 0.004 | 0.01 | 0.02 | 0.04 |

TEST EXAMPLE 2

RNAi Activity of Luciferase-Targeting siRNA

The RNAi activity of the luciferase-targeting siRNA having 8-Br-dA at the 5' end of the antisense strand obtained in Example 1 was evaluated by measuring the inhibitory effect on the expression of Luciferase GL4 mRNA (GenBank Accession No. EU921840) as described below.

In a culture dish (Multidish 24 wells, Cat. No. 142475, manufactured by Nunc, Inc.), human cervical cancer-derived cell line Hela cells (CCL-2, purchased from ATCC) were suspended in RPMI medium (Invitrogen Life Technologies, 11875093) containing 10% fetal bovine serum, and 500 μL of the resulting cell suspension was inoculated into each well to give 50000 cells/well. Thereto, 100 μL of a solution of an siRNA-Lipofectamine RNAiMAX (Invitrogen Life Technologies, 13778-075) complex mixed in OPTI-MEM (Invitrogen Life Technologies, 31985-070) was added, whereby the siRNA was introduced into the Hela cells. The final concentration of the siRNA was set to the following seven levels: 10000 pmol/L, 2000 pmol/L, 400 pmol/L, 80 pmol/L, 16 pmol/L, 3.2 pmol/L, and 0.64 pmol/L. Further, as a negative control group, cells to which only Lipofectamine RNAiMAX was added were inoculated.

The cells after introduction of the siRNA were cultured under the conditions of 37° C. and 5% $CO_2$ for 24 hours. In order to collect RNA, an RNA extraction kit (RNeasy 74106) of Qiagen, Inc. was used. The cells after culture were washed once with phosphate buffer, and then lysed with RLT buffer (attached to Rneasy) attached to the RNeasy kit and collected. Then, the total RNA was collected according to the instruction attached to the kit. By using the total RNA (1 μg) as a template, a reverse transcription reaction was performed by using Transcriptor First Strand cDNA Synthesis Kit (Roche, 4897030001), whereby a cDNA was prepared. By using this cDNA as a template for the PCR reaction, a GL4 (GenBank Accession No. EU921840) gene and, as a control, D-glyceraldehyde-3-phosphate dehydrogenase (GAPDH, GenBank Accession No. NM_001256799) were subjected to the PCR reaction by the Taqman probe method using ABI 7900HT Fast (Applied Biosystems, Inc. (ABI)), and each level of amplified mRNAs was measured. Then, a semi-quantitative level of mRNA of GL4 was calculated using the level of the amplified mRNA of GAPDH as an internal control. In the measurement of GAPDH, Taqman probe Hs99999905 ml (Applied Biosystems, Inc. (ABI)) was used. In the measurement of GL4, the probe #20 in the universal probe library (Roche, 04686934001), and as the amplification primers, a DNA having a base sequence represented by SEQ ID NO: 63 (forward primer) and a DNA having a base sequence represented by SEQ ID NO: 64 (reverse primer) were used. Further, in the negative control group, the level of mRNA of GL4 and the level of the amplified mRNA of GAPDH were measured in the same manner, respectively, and a semi-quantitative level of mRNA of GL4 was calculated using the level of amplified mRNA of GAPDH as an internal control.

The level of the target mRNA in the siRNA-introduced sample was represented as a relative ratio when the level of the mRNA of GL4 in the siRNA-unintroduced group (negative control group) was taken as 1.

An $IC_{50}$ value was calculated by the Logit method. A statistical analysis was performed using statistical analysis software SAS (Release 9.2, SAS institute, Inc.)

In Table 12, the $IC_{50}$ values of 874-BrdA, which is the siRNA of the present invention, and 874-A and 874-U, which have adenosine monophosphate or uridine monophosphate at a position corresponding to 8-Br-dA in the sequence thereof as a comparison, are shown.

TABLE 12

| | 874-BrdA | 874-U | 874-A |
|---|---|---|---|
| $IC_{50}$(pmol/L) | 1.8 | 3.3 | 13.3 |

From the results of Test Examples 1 and 2, it is found that the siRNA having 8-Br-dA at the 5' end of the antisense strand (874-BrdA) shows a higher knockdown activity against the expression of luciferase than the siRNA having a corresponding natural nucleotide at the 5' end of the antisense strand.

EXAMPLE 2

A luciferase-targeting siRNA having 8-oxo-2'-deoxyadenosine monophosphate at the 5' end of the antisense strand shown in Table 13 (referred to as 874-8-oxo-dA, X which is contained in the sequence of the antisense strand denotes 8-oxo-2'-deoxyadenosine monophosphate) was obtained by synthesis in the same manner as in Example 1 using a commercially available 8-oxo-dA-CE phosphoramidite.

EXAMPLE 3

An siRNA having 5-bromo-2'-deoxyuridine monophosphate at the 5' end of the antisense strand shown in Table 13 (referred to as 874-5-Br-dU, X which is contained in the sequence of the antisense strand denotes 5-bromo-2'-deoxyuridine monophosphate) was obtained by synthesis in the same manner as in Example 1 using a commercially available 5-Br-dU-CE phosphoramidite.

EXAMPLE 4 siRNAs having 5-fluoro-2'-deoxyuridine monophosphate at the 5' end of the antisense strand shown in Table 13 (referred to as 454-5-F-dU and 1556-5-F-dU, X which is contained in the sequence of each of the antisense strands denotes 5-fluoro-2'-deoxyuridine monophosphate) were obtained by synthesis in the same manner as in Example 1 using a commercially available 5-F-dU-CE phosphoramidite.

MALDI-TOF/MS
454-5-F-dU (antisense strand): theoretical value: 6668.85 (M-H), actual value: 6673.35
1556-5-F-dU (antisense strand): theoretical value: 6669.03 (M-H), actual value: 6671.33

From the results of Test Example 3, it is found that the siRNAs having 5-fluoro-2'-deoxyuridine monophosphate at the 5' end of the antisense strand (454-5-F-dU and 1556-5-F-dU) show a higher knockdown activity against the expression of luciferase than the siRNAs having a corresponding natural nucleotide at the 5' end of the antisense strand, respectively.

TABLE 13

|  | sense strand | | antisense strand | |
| --- | --- | --- | --- | --- |
|  | sequence (5'→3') | sequence number | sequence (5'→3') | sequence number |
| 874-8-oxo-dA | UAGCUUCUUCGCUAAGAGUAC | 3 | XCUCUUAGCGAAGAAGCUAAA | 4 |
| 874-5-Br-dU | UAGCUUCUUCGCUAAGAGAAC | 23 | XCUCUUAGCGAAGAAGCUAAA | 4 |
| 454-5-F-dU | GGAUAGCAAGACCGACUAACA | 25 | XUAGUCGGUCUUGCUAUCCAU | 26 |
| 1556-5-F-dU | GACGAGGUGCCUAAAGGAAUG | 27 | XUCCUUUAGGCACCUCGUCCA | 12 |

TEST EXAMPLE 3

RNAi Activity of Luciferase-Targeting siRNA

The RNAi activity of each of the luciferase-targeting siRNAs obtained in Example 4 (Table 13, having 5-F-dU at the position of X) was measured and evaluated in the same manner as in Test Example 2. Each of them was compared with an siRNA having a corresponding natural nucleotide at the 5' end of the antisense strand (Table 14).

In Table 15, the respective $IC_{50}$ values are shown.

EXAMPLE 5

D-Glyceraldehyde-3-phosphate dehydrogenase (GAPDH)-targeting siRNAs having 8-oxo-2'-deoxyadenosine monophosphate at the 5' end of each of the antisense strands shown in Table 16 (X contained in the sequence of each of the antisense strands denotes 8-oxo-2'-deoxyadenosine monophosphate) were obtained by synthesis in the same manner as in Example 1.

TABLE 14

|  | sense strand | | antisense strand | |
| --- | --- | --- | --- | --- |
|  | sequence (5'→3') | sequence number | sequence (5'→-3') | sequence number |
| 454-U | GGAUAGCAAGACCGACUAACA | 25 | UUAGUCGGUCUUGCUAUCCAU | 28 |
| 1556-U | GACGAGGUGCCUAAAGGAAUG | 27 | UUCCUUUAGGCACCUCGUCCA | 29 |

TABLE 15

|  | KD(Luc assay) $IC_{50}$(pM) |
| --- | --- |
| 454-U | 85 |
| 454-5-F-dU | 49 |
| 1556-U | 300 |
| 1556-5-F-dU | 132 |

TABLE 16

|  | sense strand | | antisense strand | |
| --- | --- | --- | --- | --- |
|  | sequence (5'→3') | sequence number | sequence (5'→3') | sequence number |
| 217-BrdA | GCGCCUGGUCACCAGGGCUGC | 30 | XGCCCUGGUGACCAGGCGCCC | 31 |
| 278-BrdA | CCCUUCAUUGACCUCAACUAC | 32 | XGUUGAGGUCAAUGAAGGGGU | 33 |
| 516-BrdA | GAGCCAAAAGGGUCAUCAUCU | 34 | XUGAUGACCCUUUUGGCUCCC | 35 |

TABLE 16-continued

| | sense strand | | antisense strand | |
|---|---|---|---|---|
| | sequence (5'→3') | sequence number | sequence (5'→3') | sequence number |
| 624-BrdA | CCUGCACCACCAACUGCUUAG | 36 | XAGCAGUUGGUGGUGCAGGAG | 37 |
| 715-BrdA | CACUGCCACCCAGAAGACUGU | 38 | XGUCUUCUGGGUGGCAGUGAU | 39 |
| 816-BrdA | AGGCUGUGGGCAAGGUCAUCC | 40 | XUGACCUUGCCCACAGCCUUG | 41 |
| 936-BrdA | AUGAUGACAUCAAGAAGGUGG | 42 | XCCUUCUUGAUGUCAUCAUAU | 43 |
| 1096-BrdA | CAAGCUCAUUUCCUGGAUAGA | 44 | XUACCAGGAAAUGAGCUUGAC | 45 |
| 1134-BrdA | GCAACAGGGUGGUGGACCUCA | 46 | XGGUCCACCACCCUGUUGCUG | 47 |

TEST EXAMPLE 4

RNAi Activity of D-Glyceraldehyde-3-Phosphate Dehydrogenase (GAPDH)-Targeting siRNA The RNAi activity of a GAPDH-targeting siRNA having 8-Br-dA at the 5' end of the antisense strand was evaluated by measuring an inhibitory effect on the expression of mRNA of GAPDH as described below.

In a culture dish (Multidish 24 wells, Cat. No. 142475, manufactured by Nunc, Inc.), human cervical cancer-derived cell line Hela cells (CCL-2, purchased from ATCC) were suspended in RPMI medium (Invitrogen Life Technologies, 11875093) containing 10% fetal bovine serum, and 500 μL of the resulting cell suspension was inoculated into each well to give 50000 cells/well. Thereto, 100 μL of a solution of an siRNA-Lipofectamine RNAiMAX (Invitrogen Life Technologies, 13778-075) complex mixed in OPTI-MEM (Invitrogen Life Technologies, 31985-070) was added, whereby the siRNA was Introduced into the Hela cells. The final concentration of the siRNA was set to one level: 100 pmol/L. Further, as a negative control group, cells to which only Lipofectamine RNAiMAX was added were inoculated.

The cells after introduction of the siRNA were cultured under the conditions of 37° C. and 5% $CO_2$ for 24 hours. In order to collect RNA, an RNA extraction kit (RNeasy 74106) of Qiagen, Inc. was used. The cells after culture were washed once with phosphate buffer, and then lysed with RLT buffer (attached to RNeasy) attached to the RNeasy kit and collected. Then, the total RNA was collected according to the instruction attached to the kit. By using the total RNA (1 μg) as a template, a reverse transcription reaction was performed using Transcriptor First Strand cDNA Synthesis Kit (Roche, 4897030001), whereby the cDNA was prepared. By using this cDNA as a template for a PCR reaction, a GADPH gene and, as a control, a peptidyl-prolyl cis-trans isomerase B (PPIB) gene (GenBank Accession No. NM_000942) were subjected to a PCR reaction by the Taqman probe method using ABI 7900HT Fast (ABI), and the levels of amplified mRNAs of the respective genes were measured. Then, a semi-quantitative level of mRNA of GAPDH was calculated using the level of the amplified mRNA of PPIB as an internal control. In the measurement of GAPDH, Taqman probe Hs99999905 ml (Applied Biosystems, Inc. (ABI)) was used. In the measurement of PPIB, Hs01018502 ml (Applied Biosystems, Inc. (ABI)) was used. Further, in the negative control group, the level of the mRNA of GAPDH and the level of the amplified mRNA of PPIB were measured in the same manner, respectively, and a semi-quantitative level of the mRNA of GAPDH was calculated using the level of the amplified mRNA of PPIB as an internal control.

The level of the target mRNA in the siRNA-introduced sample was represented as a relative ratio when the level of the mRNA of GAPDH in the siRNA unintroduced group (negative control group) was taken as 1.

Further, for comparison, a test was performed in the same manner also for siRNAs having adenosine monophosphate at a position corresponding to 8-Br-dA of each siRNA (Table 17).

The results of this test are shown in Table 18 and FIG. 3.

TABLE 17

| | sense strand | | antisense strand | |
|---|---|---|---|---|
| | sequence (5'→3') | sequence number | sequence (5'→3') | sequence number |
| 217-A | GCGCCUCCUCACCAGGGCUGC | 30 | AGCCCUGGUGACCAGGCGCCC | 48 |
| 278-A | CCCUUCAUUGACCUCAACUAC | 32 | AGUUGAGGUCAAUGAAGGGGU | 49 |
| 516-A | GAGCCAAAAGGGUCAUCAUCU | 34 | AUGAUGACCCUUUUGGCUCCC | 50 |
| 624-A | CCUGCACCACCAACUGCUUAG | 36 | AAGCAGUUGGUGGUGCAGGAG | 51 |
| 715-A | CACUGCCACCCAGAAGACUGU | 38 | AGUCUUCUGGGUGGCAGUGAU | 52 |
| 816-A | AGGCUGUGGGCAAGGUCAUCC | 40 | AUGACCUUGCCCACAGCCUUG | 53 |

TABLE 17-continued

| sense strand | | antisense strand | |
|---|---|---|---|
| sequence (5'→3') | sequence number | sequence (5'→3') | sequence number |
| 936-A AUGAUGACAUCAAGAAGGUGG | 42 | ACCUUCUUGAUGUCAUCAUAU | 54 |
| 1096-A CAAGCUCAUUUCCUGGUAUGA | 44 | AUACCAGGAAAUGAGCUUGAC | 55 |
| 1134-A GCAACAGGGUGGUGGACCUCA | 46 | AGGUCCACCACCCUGUUGCUG | 56 |

TABLE 18

| siRNA | level of target mRNA |
|---|---|
| 217-BrdA | 0.743 |
| 217-A | 1.654 |
| 278-BrdA | 0.189 |
| 278-A | 0.361 |
| 516-BrdA | 0.246 |
| 516-A | 0.648 |
| 624-BrdA | 0.273 |
| 624-A | 0.798 |
| 715-BrdA | 0.627 |
| 715-A | 1.321 |
| 816-BrdA | 0.291 |
| 816-A | 0.464 |
| 936-BrdA | 0.217 |
| 936-A | 0.602 |
| 1096-BrdA | 0.027 |
| 1096-A | 0.241 |
| 1134-BrdA | 0.067 |
| 1134-A | 0.597 |

From the results of Test Example 4, it is found that the D-glyceraldehyde-3-phosphate dehydroagenase (GAPDH)-targeting siRNA having 8-Br-dA at the 5' end of the antisense strand shows a higher knockdown activity against the expression of GAPDH than the siRNA having a corresponding natural nucleotide at the 5' end of the antisense strand.

EXAMPLE 6

It was synthesized using a D-glyceraldehyde-3-phosphate dehydrogenase (GAPDH)-targeting siRNA having 5-fluoro-2'-deoxyuridine monophosphate at the 5' end of the antisense strand shown in Table 19 (X contained in the sequence of the antisense strand denotes 5-fluoro-2'-deoxyuridine monophosphate) in the same manner as in Example 1.
MALDI-TOF/MS
1096-5-F-dU (antisense strand): theoretical value: 6801.03 (M-H), actual value: 6797.74

TEST EXAMPLE 5

RNAi Activity of D-Glyceraldehyde-3-Phosphate Dehydrogenase (GAPDH)-Targeting siRNA The activity of the GAPDDH-targeting siRNA obtained in Example 6 was evaluated by measuring an inhibitory effect on the expression of mRNA of GAPDH in the same manner as in Test Example 4.

The level of the target mRNA in the siRNA-introduced sample was represented as a relative ratio when the level of mRNA of GAPDH in the siRNA-unintroduced group (negative control group) was taken as 1. The level of mRNA of GAPDH was calculated using the level of the amplified mRNA of hypoxanthine phosphoribosyltransferase 1 (HPRT1, GenBank Accession No. NM 000194) as an internal control. In the measurement of HPRT1, Taqman probe Hs99999909_m1 (Applied Biosystems, Inc. (ABI)) was used.

Further, for comparison, a test was performed in the same manner also for siRNAs having uracil monophosphate, adenosine monophosphate, or guanine monophosphate at the 5' end of the antisense of each siRNA (Table 19).

The results of this test are shown in Table 20.

TABLE 20

| siRNA | concentration (pM) | level of target mRNA | concentration (pM) | level of target mRNA |
|---|---|---|---|---|
| 1096-5-FU | 10 | 0.059 | 1 | 0.183 |
| 1096-A | 10 | 0.096 | 1 | 0.273 |
| 1096-U | 10 | 0.059 | 1 | 0.238 |
| 1096-G | 10 | 0.102 | 1 | 0.374 |

From the results of Test Example 5, it is found that the D-glyceraldehyde-3-phosphate dehydrogenase (GAPDH)-targeting siRNA having 5-fluoro-2'-deoxyuridine monophosphate at the 5' end of the antisense strand shows a higher

TABLE 19

| sense strand | | antisense strand | |
|---|---|---|---|
| sequence (5'→3') | sequence number | sequence (5'→3') | sequence number |
| 1096-5-F-dU CAAGCUCAUUUCCUGGUAAGA | 57 | XUACCAGGAAAUGAGCUUGAC | 55 |
| 1096-U CAAGCUCAUUUCCUGGUAAGA | 57 | UUACCAGGAAAUGAGCUUGAC | 58 |
| 1096-A CAAGCUCAUUUCCUGGUAUGA | 59 | AUACCAGGAAAUGAGCUUGAC | 60 |
| 1096-G CAAGCUCAUUUCCUGGUACGA | 61 | GUACCAGGAAAUGAGCUUGAC | 62 | knockdown activity against the expression of GAPDH than the siRNA having a corresponding natural nucleotide at the 5' end of the antisense strand.

REFERENCE EXAMPLE 1.0

Compound I-5

Step 1

Commercially available 6,7-dimethoxyquinazoline-2,4 (1H,3H)-dione (220 mg, 0.991 mmol) and 1-O-acetyl-2,3,5-tri-O-benzoyl-β-D-ribofuranose (500 mg, 0.991 mol) were dissolved in acetonitrile (5 mL), and N,O-bis(trimethylsilyl)acetamide (0.735 mL, 2.97 mmol) was added thereto, and the mixture was stirred at 60° C. for 20 minutes. After the reaction solution was cooled to room temperature, methanesulfonyl trimethylsilyl (0.627 mL, 3.47 mmol) was added thereto, and the mixture was stirred at 60° C. for 1 hour. After the reaction solution was cooled to room temperature, a saturated aqueous sodium bicarbonate solution was added thereto, and the mixture was extracted with ethyl acetate. The organic layer was washed with saturated brine, and then dried over sodium sulfate. The residue obtained by evaporating the solvent under reduced pressure was purified by column chromatography (heptane/ethyl acetate) to obtain (2R,3R,4R,5R)-2-((benzoyloxy)methyl)-5-(6,7-dimethoxy-2,4-dioxo-3,4-dihydroquinazolin-1(2H)-yl)tetrahydrofuran-3,4-diyl dibenzoate (599 mg, yield: 91%).

Step 2

(2R,3R,4R,5R)-2-((Benzoyloxy)methyl)-5-(6,7-dimethoxy-2,4-dioxo-3,4-dihydroquinazolin-1(2H)-yl)tetrahydrofuran-3,4-diyl dibenzoate (599 mg, 0.899 mmol) obtained in Step 1 was dissolved in methanol (9 mL), and a methylamine/methanol solution (4.58 mL, 44.9 mmol) was added thereto, and the mixture was stirred overnight at room temperature. To the residue obtained by evaporating the solvent under reduced pressure, diethyl ether was added, and the precipitate was collected by filtration to obtain 1-((2R,3R,4S,5R)-3,4-dihydroxy-5-(hydroxymethyl)tetrahydrofuran-2-yl)-6,7-dimethoxyquinazoline-2,4(1H,3H)-dione (312 mg, yield: 98%).

ESI-MS (m/z): 353 (M−1)

Step 3

1-((2R,3R,4S,5R)-3,4-Dihydroxy-5-(hydroxymethyl)tetrahydrofuran-2-yl)-6,7-dimethoxyquinazoline-2,4(1H,3H)-dione (310 mg, 0.875 mmol) obtained in Step 2 was suspended in acetone (15 mL), and 2,2-dimethoxypropane (0.536 mL, 4.37 mmol) and 4-toluenesulfonic acid monohydrate (183 mg, 0.962 mmol) were added thereto, and the mixture was stirred at room temperature for 2 hours. To the reaction solution was added a saturated aqueous sodium bicarbonate solution, and then, the solvent was evaporated under reduced pressure until the amount of the solvent was decreased to about half, and the resulting residue was purified by column chromatography (chloroform/methanol) to obtain 1-((3aR,4R,6R,6aR)-6-(hydroxymethyl)-2,2-dimethyltetrahydrofuro[3,4-d][1,3]dioxol-4-yl)-6,7-dimethoxyquinazoline-2,4(1H,3H)-dione (315 mg, yield: 91%).

ESI-MS (m/z): 395 (M+1)

Step 4

1-((3aR,4R,6R,6aR)-6-(Hydroxymethyl)-2,2-dimethyltetrahydrofuro[3,4-d][1,3]dioxol-4-yl)-6,7-dimethoxyquinazoline-2,4(1H,3H)-dione (310 mg, 0.786 mmol) obtained in Step 3 was dissolved in dichloromethane (8 mL), and 1H-tetrazole (138 mg, 1.97 mmol) and di-tert-butyl diisopropylphosphoramide (0.522 mL, 1.57 mmol) were added thereto, and the mixture was stirred at room temperature for 5 hours. The reaction solution was cooled to 0° C., and m-chloroperbenzoic acid (452 mg, 1.97 mmol) was added thereto, and the mixture was further stirred at 0° C. for 20 minutes. To the reaction solution was added a saturated aqueous sodium bicarbonate solution, and the mixture was extracted with chloroform and dried over sodium sulfate. The residue obtained by evaporating the solvent under reduced pressure was purified by column chromatography (heptane/ethyl acetate) to obtain di-tert-butyl ((3aR,4R,6R,6aR)-6-(6,7-dimethoxy-2,4-dioxo-3,4-dihydroquinazolin 1(2H)-yl)-2,2-dimethyltetrahydrofuro[3,4-d][1,3]dioxol-4-yl)methyl phosphate (259 mg, yield: 56%).

ESI-MS (m/z): 587 (M+1)

Step 5

Di-tert-butyl ((3aR,4R,6R,6aR)-6-(6,7-dimethoxy-2,4-dioxo-3,4-dihydroquinazolin 1(2H)-yl)-2,2-dimethyltetrahydrofuro[3,4-d][1,3]dioxol-4-yl)methyl phosphate (77.5 mg, 0.132 mmol) obtained in Step 4 was dissolved in trifluoroacetic acid/water (1:1) (2 mL), and the mixture was stirred at room temperature for 2 hours. After the solvent was evaporated under reduced pressure, acetic acid-triethylamine buffer (pH 6.5) (2 mL) was added thereto, and the solvent was evaporated again under reduced pressure. The resulting residue was dissolved in ethanol, and ethyl acetate was added thereto, and the precipitate was collected by filtration to obtain ((2R,3S,4R,5R)-5-(6,7-dimethoxy-2,4-dioxo-3,4-dihydroquinazolin-1(2H)-yl)-3,4-dihydroxytetrahydrofuran-2-yl)methyl phosphate (Compound I-5) triethylammonium salt (64.9 mg, yield: 92%).

$^1$H-NMR (D$_2$O, 300 MHz) δ: 7.43 (s, 1H), 6.91 (s, 1H), 6.08 (d, J=4.0 Hz, 1H), 4.77-4.58 (m, 1H), 4.38 (t, =7.3 Hz, 1H), 4.04-4.02 (m, 3H), 3.90 (s, 3H), 3.81 (s, 3H), 3.08 (q, J=7.3 Hz, 6H), 1.16 (t, J=7.3 Hz, 9H).

EST-MS (m/z): 435 (M+1)

REFERENCE EXAMPLE 1.1

Compound am-1

Step 1

1-((2R,3R,4S,5R)-3,4-Dihydroxy-5-(hydroxymethyl)tetrahydrofur an-2-yl)-6,7-dimethoxyquinazoline-2,4(1H,3H)-dione (812 mg, 2.29 mmol) obtained in Step 2 of Reference Example 1.0 was dissolved in DMF (10.0 mL), and to the mixture was added di-tert-butylsilyl bis(trifluoromethanesulfonate) (1.00 mL, 2.75 mmol) under ice cooling, and the mixture was stirred under ice cooling for 6 hours. To the reaction mixture was added a saturated aqueous sodium bicarbonate solution, and the mixture was extracted with ethyl acetate. Thereafter, the organic layer was washed with saturated brine and dried over anhydrous magnesium sulfate. The solvent was evaporated under reduced pressure, and the residue was purified by silica gel column chromatography (ethyl acetate/heptane) to obtain 1-((4aR,6R,7R,7aS)-2,2-di-tert-butyl-7-hydroxytetrahydro-4H-furo[3,2-d][1,3,2]dioxasilin-6-yl)-6,7-dimethoxyquinazoline-2,4(1H,3H)-dione (1.08 g, 95.0%).

ESI-MS (m/z): 493 (M−1)

Step 2

1-((4aR,6R,7R,7aS)-2,2-Di-tert-butyl-7-hydroxytetrahydro-4H-furo[3,2-d][1,3,2]dioxasilin-6-yl)-6,7-dimethoxyquinazoline-2,4(1H,3H)-dione (1.73 mg, 3.50 mmol) obtained in Step 1 was dissolved in DMF (18.0 mL), and imidazole (1.19 g, 17.5 mmol) and tert-butyldimethylsilyl chloride (791 mg, 5.25 mmol) were added thereto, and the mixture was stirred at 60° C. for 3 hours. To the reaction mixture was added a saturated aqueous sodium bicarbonate solution, and the mixture was extracted with ethyl acetate. Thereafter, the organic layer was washed with saturated brine and dried over anhydrous magnesium sulfate. The solvent was evaporated under reduced pressure, and the residue was purified by silica gel column chromatography (ethyl acetate/heptane) to obtain 1-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6,7-dimethoxyquinazoline-2,4(1H,3H)-dione (1.95 g, 92.0%).

ESI-MS (m/z): 607 (M−1)

Step 3

1-((4aR,6R,7R,7aR)-2,2-Di-tert-butyl-7-((tert-butyldimethylsilyl)oxy)tetrahydro-4H-furo[3,2-d][1,3,2]dioxasilin-6-yl)-6,7-dimethoxyquinazoline-2,4(1H,3H)-dione (500 mg, 0.821 mmol) obtained in Step 2 was dissolved in dichloromethane (8.00 mL), and pyridine (0.531 mL, 6.57 mmol) and hydrogen fluoride-pyridine (0.423 mL, 3.28 mmol) wore added thereto under ice cooling, and the mixture was stirred under ice cooling for 1 hour. To the reaction mixture was added a saturated aqueous sodium bicarbonate solution, and the mixture was extracted with ethyl acetate. Thereafter, the organic layer was washed with saturated brine and dried over anhydrous magnesium sulfate. The solvent was evaporated under reduced pressure, and the residue was purified by silica gel column chromatography (ethyl acetate/heptane) to obtain 1-((2R,3R,4R,5R)-3-((tert-butyldimethylsilyl)oxy)-4-hydroxy-5-(hydroxymethyl)tetrahydrofuran-2-yl)-6,7-dimethoxyquinazoline-2,4(1H,3H)-dione (336 my, 87.0%).

ESI-MS (m/z): 467 (M−1)

Step 4

1-((2R,3R,4R,5R)-3-((Tert-butyldimethylsilyl)oxy)-4-hydroxy-5-(hydroxymethyl)tetrahydrofuran-2-yl)-6,7-dimethoxyquinazoline-2, 4 (1H,3H)-dione (895.0 mg, 0.181 mmol) obtained in Step 3 was dissolved in pyridine (2.00 mL), and p,p'-dimethoxytrityl chloride (184 mg, 0.544 mmol) and 4-dimethylaminopyridine (4.43 mg, 0.0360 mmol) were added thereto, and the mixture was stirred at room temperature for 1 hour. To the reaction mixture, a saturated aqueous sodium bicarbonate solution was added, and the mixture was extracted with ethyl acetate. Thereafter, the organic layer was washed with saturated brine and dried over anhydrous magnesium sulfate. The solvent was evaporated under reduced pressure, and the residue was purified by silica gel column chromatography (ethyl acetate/heptane) to obtain 1-((2R,3R,4R,5R)-5-((bis(4-methoxyphenyl)(phenyl)methoxy)methyl)-3-((tert-butyldimethylsilyl)oxy)-4-hydroxytetrahydrofuran-2-yl)-6,7-dimethoxyquinazoline-2, 4(1H,3H)-dione (138 mg, 99.0%).

ESI-MS (m/z): 769 (M−1)

Step 5

1-((2R,3R,4R,5R)-5-((Bis(4-methoxyphenyl)(phenyl)methoxy)methyl)-3-(tert-butyldimethylsilyl)oxy)-4-hydroxytetrahydrofuran-2-yl)-6,7-dimethoxyquinazoline-2,4 (1H,3H)-dione (74.0 mg, 0.0960 mmol) obtained in Step 4 was dissolved in THF (2.00 mL), and diisopropylamine (0.084 mL, 0.480 mmol) and 2-cyanoethyl chloro(diisopropylamino) phosphinite (0.043 mL, 0.192 mmol) were added thereto under ice cooling, and the mixture was stirred at room temperature for 3 hours. The solvent was evaporated under reduced pressure, and the residue was purified by aminosilica gel column chromatography (ethyl acetate/heptane), and then, further purified by silica gel column chromatography (ethyl acetate/heptane) to obtain (2R,3R,4R,5R)-2-((bis(4-methoxyphenyl)(phenyl)methoxy)methyl)-4-( (tert-butyldimethylsilyl)oxy) -5-(6,7-dimethoxy-2,4-dioxo-3,4-dihy droquinazolin-1(2H)-yl)tetrahydrofuran-3-yl(2-cyanoethyl) diisopropylphosphoramidite (Compound am-1, 63.0 mg, 67.6%).

$^1$H-NMR (CDCl$_3$, 300 MHz) δ: 7.94 (1H, brs), 7.55 (1H, s), 7.47-7.39 (2H, m), 7.38-7.12 (7H, m), 6.93 (1H, s), 6.81-6.70 (4H, m), 5.92 (1H, d, J=4.8 Hz), 5.18-5.08 (1H, m), 4.53-4.38 (1H, m), 4.37-4.26 (1H, m), 3.96-3.48 (16H, m), 3.46-3.23 (1H, m), 2.68-2.52 (1H, m), 2.35-2.27 (1H, m), 1.20-1.00 (1H, m), 0.83, 0.81 (9H, 2 s), 0.05, 0.03, −0.10, −0.09 (6H, 4 s).

ESI-MS (m/z): 971 (M+1)

EXAMPLE 7

An siRNA having Compound I-5 as X at the 5' end of the antisense strand of 454-Xu shown in Table 24 below was synthesized in the same manner as in Example 1 using Compound am-1 obtained in Reference Example 1.1.

MALDI-TOF/MS (antisense strand): theoretical value: 6776.96 (M-H), actual value: 6776.21

REFERENCE EXAMPLE 2.0

Compound I-6

((2R,3,4R,5R)-5-(6-Chloro-2,4-dioxo-3,4-dihydroquinazolin-1(2H)-yl)-3,4-dihydroxytetrahydrofuran-2-yl)methyl phosphate (Compound I-6) was obtained in the same manner as in Reference Example 1.0 using commercially available 6-chloroquinazoline-2,4(1H,3H)-dione.

$^1$H-NMR (D$_2$O, 300 MHz) δ: 7.88 (d, J=3.8 Hz, 1H), 7.64 (dd, J=9.2, 2.6 Hz, 1H), 7.58 (d, J=9.2 Hz, 1H), 6.14 (d, J=5.5 Hz, 1H), 4.70-4.68 (m, 1H), 4.37 (t, J=5.9 Hz, 1H), 4.09-4.02 (m, 3H).

ESI-MS (m/z): 409 (M+1)

REFERENCE EXAMPLE 2.1

Compound am-2

(2R,3R,4R,5R)-2-((Bis(4-methoxyphenyl)(phenyl)methoxy)methyl) 4-((tert-butyldimethylsilyl)oxy)-5-(6-chloro-2,4-dioxo-3,4-dihydroquinazolin-1(2H)-yl)tetrahydrofuran-3-yl(2-cyanoethyl) diisopropylphosphoramidite (Compound am-2) is obtained in the same manner as in Reference Example 1.1 using commercially available 6-chloroquinazoline-2,4(1H,3H)-dione.

EXAMPLE 8

An siRNA having Compound I-6 at the 5' end of the antisense strand is synthesized in the same manner as in Example 1 using Compound am-2 obtained in Reference Example 2.1.

REFERENCE EXAMPLE 3.0

Compound I-7

((2R,3S,4R,5R)-5-(7-Chloro-2,4-dioxo-3,4-dihydroquinazolin-1(2H)-yl)-3,4-dihydroxytetrahydrofuran-2-yl)methyl phosphate (Compound I-7) was obtained in the same manner as in Reference Example 1.0 using commercially available 7-chloroquinazoline-2,4(1H,3H)-dione.

$^1$H-NMR (D$_2$O, 300 MHz) δ: 7.95 (d, J=8.4 Hz, 1H), 7.61 (s, 1H), 7.30 (d, J=8.4 Hz, 1H), 5.99 (d, J=4.4 Hz, 1H), 4.79 (t, J=5.3 Hz, 1H), 4.38 (t, J=6.4 Hz, 1H), 4.04-3.92 (m, 3H).

ESI-MS (m/z): 409 (M+1)

REFERENCE EXAMPLE 3.1

Compound am-3

(2R,3R,4R,5R)-2-((Bis(4-methoxyphenyl)(phenyl)methoxy)methyl) 4-((tert-butyldimethylsilyl)oxy)-5-(7-chloro-2,4-dioxo-3,4-dihydroquinazolin-1(2H)-yl)tetrahydrofuran-3-yl(2-cyanoethyl) diisopropylphosphoramidite (Compound am-3) was obtained in the same manner as in Reference Example 1.1 using commercially available 7-chloroquinazoline-2,4(1H,3H)-dione.

$^1$H-NMR (CDCl$_3$, 500 MHz) δ: 8.11 (d, J=8.5 Hz, 1H), 7.67 (7.63) (d, J=1.7 Hz, 1H), 7.45-6.76 (m, 14H), 6.02 (m, 1H), 5.12 (5.07) (m, 1H), 4.45 (m, 1H), 4.32 (4.28) (m, 1H), 3.97-3.25 (m, 12H), 2.70-2.23 (m, 2H), 1.21-1.01 (m, 12H), 0.80 (0.82) (s, 9H), 0.03 (0.05) (8, 3H), −0.12 (s, 3H).

EXAMPLE 9

An siRNA having Compound I-7 as X at the 5' end of the antisense strand of 454-Xu shown in Table 24 below was synthesized in the same manner as in Example 1 using Compound am-3 obtained in Reference Example 3.1.

MALDI-TOF/MS (antisense strand): theoretical value: 6751.35 (M-H), actual value: 6751.83

REFERENCE EXAMPLE 4.0

Compound I-8

((2R,3S,4R,5R)-5-(5-Chloro-2,4-dioxo-3,4-dihydroquinazolin-1(2H)-yl)-3,4-dihydroxytetrahydrofuran-2-yl)methyl phosphate (Compound I-8) was obtained in the same manner as in Reference Example 1.0 using commercially available 5-chloroquinazoline-2,4(1H,3H)-dione.

$^1$H-NMR (D$_2$O, 300 MHz) δ: 7.66 (d, J=4.8 Hz, 2H), 7.40 (t, J=4.4 Hz, 1H), 6.21 (d, J=5.5 Hz, 1H), 4.80 (c, J=5.9 Hz, 1H), 4.45 (t, J=5.9 Hz, 1H), 4.09 (dd, J=14.5, 7.1 Hz, 3H).
ESI-MS (m/z): 409 (M+1)

REFERENCE EXAMPLE 4.1

Compound am-4

(2R,3R,4R,5R)-2-((Bis(4-methoxyphenyl)(phenyl)methoxy)methyl)-4-((tert-butyldimethylsilyl)oxy)-5-(5-chloro-2,4-dioxo-3,4-dihydroquinazolin-1(2H)-yl)tetrahydrofuran-3-yl(2-cyanoethyl) diisopropyrolphosphoramidite (Compound am-4) is obtained in the same manner as in Reference Example 1.1 using commercially available 5-chloroquinazoline-2,4(1H,3H)-dione.

EXAMPLE 10

An siRNA having Compound I-8 at the 5' end of the antisense strand is synthesized in the same manner as in Example 1 using Compound am-4 obtained in Reference Example 4.1.

REFERENCE EXAMPLE 5.0

Compound I-9

(2R,3S,4R,5R)-5-(2,4-Dioxo-3,4-dihydrothieno[3,2-d]pyrimidin-1(2H)-yl)-3,4-dihydroxytetrahydrofuran-2-yl)methyl phosphate (Compound I-9) triethylammonium salt was obtained in the same manner as in Reference Example 1.0 using commercially available thieno[3,2-d]pyrimidine-2,4(1H,3H)-dione.

$^1$H-NMR (D$_2$O, 300 MHz) δ: 7.96 (d, J=5.5 Hz, 1H), 7.45 (d, J=4.8 Hz, 1H), 6.14 (d, J=6.2 Hz, 1H), 4.73-4.56 (m, 1H), 4.35 (t, J=5.7 Hz, 1H), 4.09 (brs, 1H), 4.02 (c, J=4.8 Hz, 2H), 3.07 (q, J=7.3 Hz, 6H), 1.15 (t, J=7.3 Hz, 9H).
ESI-MS (m/z): 381 (M+1)

REFERENCE EXAMPLE 5.1

Compound am-5

(2R,3R,4R,5R)-2-((Bis(4-methoxyphenyl)(phenyl)methoxy)methyl)-4-((tert-butyldimethylsilyl)oxy)-5-(2,4-dioxo-3,4-dihydrothieno[3,2-d]pyrimidin-1(2H)-yl)tetrahydrofuran-3-yl(2-cyanoethyl) diisopropylphosphoramidite (Compound am-5) is obtained in the same manner as in Reference Example 1.1 using commercially available thieno[3,2-d]pyrimidine-2,4(1H,3H)-dione.

EXAMPLE 11

An siRNA having Compound I-9 at the 5' end of the antisense strand is synthesized in the same manner as in Example 1 using Compound am-5 obtained in Reference Example 5.1.

REFERENCE EXAMPLE 6.0

Compound I-10

Step 1

(2R,3R,4S,5R)-2-(6-Chloro-9H-purin-9-yl)-5-(hydroxymethyl)tetrahydrofuran-3,4-diol (5.47 g, yield: 72%) was obtained according to the process described in the known method (Journal of Organic Chemistry (J. Org. Chem.), 2002, vol. 67, pp. 6708-67963 using (2R,3R,4R,5R)-2-(acetoxymethyl)-5-(6-chloro-9H-purin-9-yl)tetrahydrofuran-3,4-diyl diacetate (10.9 g, 26.4 mmol) synthesized by the method described in the known method [Journal of Medicinal Chemistry (J. Med. Chem.), 2012, vol. 55, pp. 1478-1489].

(2R,3R,4S,5R)-2-(6-Chloro-9H-purin-9-yl)-5-(hydroxymethyl)tetrahydrofuran-3,4-diol (5.48 g, 19.1 mmol) was suspended in acetone (200 mL), and 2,2-dimethoxypropane (11.7 mL, 95.5 mmol) and 4-toluenesulfonic acid monohydrate (9.09 g, 47.8 mmol) were added thereto, and the mixture was stirred at room temperature for 2 hours. To the reaction solution was added a saturated aqueous sodium bicarbonate solution, and the solvent was evaporated under reduced pressure until the amount of the solvent was decreased to about half. Chloroform was added thereto, and the mixture was extracted with chloroform and dried over sodium sulfate. Then, the residue obtained by evaporating the solvent under reduced pressure was purified by silica gel column chromatography (heptane/ethyl acetate) to obtain ((3aR,4R,6R,6aR)-6-(6-chloro-9H-purin-9-yl)-2,2-dimethyltetrahydrofuro[3,4-d][1.3]dioxol-4-yl)methanol (5.17 g, yield: 83%).
ESI-MS (m/z): 327 (M+1)

Step 2

1,4-Dioxane (2 mL) and water (one drop) were added to ((3aR,4R,6R,6aR)-6-(6-chloro-9H-purin-9-yl)-2,2-dimethyltetrahydrofuro[3,4-d][1,3]dioxol-4-yl)methanol (150 mg, 0.459 mmol) obtained in Step 1, (E)-styrylboronic acid (136 mg, 0.918 mmol), 1,1'-bis(diphenylphosphino)ferrocene-palladium(II) dichloride-dichloromethane complex (37.5 mg, 0.031 mmol), and cesium carbonate (449 mg, 1.38 mmol), and the mixture was stirred at 80° C. for 3 hours under a nitrogen atmosphere. After the reaction solution was cooled to room temperature, saturated brine was added thereto, and the mixture was extracted with ethyl acetate and dried over sodium sulfate. The residue obtained by evaporating the solvent under reduced pressure was purified by column chromatography (heptane/ethyl acetate) to obtain ((3aR,4R,6R,6aR)-2,2-dimethyl-6-(6-((E)-styryl)-9H-purin-9-yl)tetrahydrofuro[3,4-d][1,3]dioxol-4-yl)methanol (90.1 mg, yield: 50%).

ESI-MS (m/z): 395 (M+1)

Step 3

((3aR,4R,6R,6aR)-2,2-Dimethyl-6-(6-styryl-9H-purin-9-yl)tetrahydrofuro[3,4-d][1,3]dioxol-4-yl)methanol (90 mg, 0.228 mmol) obtained in Step 2 was dissolved in dichloromethane (2 mL), and 1H-tetrazole (32.0 mg, 0.456 mmol) and di-tert-butyl diisopropylphosphoramide (0.144 mL, 0.456 mmol) were added thereto, and the resulting solution was stirred at 0° C. for 2 hours. To the reaction solution, m-chloroperbenzoic acid (141 mg, 0.612 mmol) was added, and the mixture was stirred at 0° C. for 15 minutes. To the reaction solution were added a saturated aqueous sodium bicarbonate solution and saturated brine, and the mixture was extracted with chloroform and dried over magnesium sulfate. A residue obtained by evaporating the solvent under reduced pressure was purified by column chromatography (heptane/ethyl acetate) to obtain di-tert-butyl ((3aR,4R,6R,6aR)-2,2-dimethyl-6-(6-styryl-9H-purin-9-yl)tetrahydrofuro[3,4-d][1,3]dioxol-4-yl)methyl phosphate (E/Z geometric isomer mixture, 73.2 mg, yield: 55%).

ESI-MS (m/z): 587 (M+1)

Step 4

Di-tert-butyl ((3aR,4R,6R,6aR)-2,2-dimethyl-6-(6-styryl-9H-purin-9-yl)tetrahydrofuro[3,4-d][1,3]dioxol-4-yl)methyl phosphate (73.0 mg, 0.124 mmol) obtained in Step 3 was dissolved in trifluoroacetic acid/water (1:1) (2 mL), and the mixture was stirred at room temperature for 2 hours. To the residue obtained by evaporating the solvent under reduced pressure was added acetic acid-ammonium acetate buffer (pH 5.7), and then, the residue was purified by preparative HPLC (eluent: a 0.01 mmol/L aqueous ammonium acetate solution/methanol) to give the roughly purified product. To the roughly purified product, 2-propanol was added, and the precipitate was collected by filtration to obtain ((2R,3S,4R,5R)-3,4-dihydroxy-5-(6-((E)-styryl)-9H-purin-9-yl)tetrahydrofuran-2-yl)methyl phosphate (Compound I-10, 21.3 mg, yield: 39%).

$^1$H-NMR (D$_2$O, 300 MHz) δ: 8.50 (s, 1H), 8.42 (s, 1H), 7.58 (d, J=15.6 Hz, 1H), 7.19-7.13 (m, 2H), 7.08-6.97 (m, 4H), 5.92 (d, J=4.9 Hz, 1H), 4.60-4.55 (m, 1H), 4.38-4.34 (m, 1H), 4.28-4.23 (m, 1H), 4.10-3.97 (m, 2H).

ESI-MS (m/z): 435 (M+1)

REFERENCE EXAMPLE 6.1

Compound am-6

Step 1

Trifluoroacetic acid/water (1:1) (2 m) was added to ((3aR, 4R,6R,6aR)-2,2-dimethyl-6-(6-((E)-styryl)-9H-purin-9-yl) tetrahydrofuro[3,4-d][1,3]dioxo-4-yl)methanol (100 mg) obtained in Step 2 of Reference Example 6.0, and the mixture was stirred at room temperature for 2 hours. Then, the solvent was evaporated under reduced pressure to obtain (2R,3S,4R,5R)-2-(hydroxymethyl)-5-(6-((E)styryl)-9H-purin-9-yl)tetrahydrofuran-3,4-diol trifluoroacetate.

Step 2

(2R,3R,4R,5R)-2-((Bis(4-methoxyphenyl)(phenyl) methoxy)methyl)-4-((tert-butyldimethylsilyl)oxy)-5-(6-((E) styryl)-9H-purin-9-yl)tetrahydrofuran-3-yl(2-cyanoethyl) diisopropylphosphoramidite (Compound am-6) is obtained in the same manner as in Reference Example 1.1 using (2R,3S,4R,5R)-2-(hydroxymethyl)-5-6-((E)styryl)-9H-purin-9-yl)tetrahydrofuran-3,4-diol trifluoroacetate obtained in Step 1.

EXAMPLE 12

An siRNA having Compound I-10 at the 5' end of the antisense strand is synthesized in the same manner as in Example 1 using Compound am-6 obtained in Reference Example 6.1.

REFERENCE EXAMPLE 7.0

Compound I-11

Step 1

(2R,3R,4R,5R)-2-(Acetoxymethyl)-5-(6-chloro-9H-purin-9-yl)tetrahydrofuran-3,4-diyl diacetate (2.00 g, 4.85 mmol) synthesized by the method described in the known method [Journal of Medicinal Chemistry (J. Med. Chem.), 2012, vol. 55, pp. 1478-1489] was dissolved in THF (15 mL), and dimethylamine hydrochloride (1.19 g, 14.5 mmol) and triethylamine (2.70 mL, 19.38 mL) were added thereto, and the mixture was stirred overnight at 60° C. in a sealed tube. To the reaction solution, dimethylamine hydrochloride (1.19 g, 14.5 mmol) and triethylamine (2.70 mL, 19.39 mL) were added, and the mixture was further stirred overnight at 60° C. To the mixture, water was added, and the mixture was extracted with chloroform and concentrated under reduced pressure to obtain (2R,3R,4R,5R)-2-(acetoxymethyl)-5-(6-(dimethylamino)-9H-purin-9-yl)tetrahydrofuran-3,4-diyl diacetate (2.2 g, yield: 1.08%).

ESI-MS (m/z): 422 (M+1)

Step 2

A 7.0 mol/L ammonia/methanol solution (33.9 mL) was added to (2R,3R,4R,5R)-2-(acetoxymethyl)-5-(6-(dimethylamino)-9H-purin-9-yl)tetrahydrofuran-3,4-diyl diacetate (2.00 g, 4.75 mmol) obtained in Step 1, and the mixture was stirred overnight at room temperature. To the residue obtained by evaporating the solvent under reduced pressure was added an ether/ethyl acetate mixed solution, and the insoluble material was collected by filtration to obtain (2R,3R,4S,5R)-2-(6-(dimethylamino)-9H-purin-9-yl)-5-(hydroxymethyl)tetrahydrofuran-3,4-diol (1.2 g, yield: 86%).

ESI-MS (m/z): 296 (M+1)

Step 3

(2R,3R,4S,5R)-2-(6-(Dimethylamino)-9H-purin-9-yl)-5-(hydroxymethyl)tetrahydrofuran-3,4-diol (1.2 g, 4.06 mmol) obtained in Step 2 was suspended in 0.5 M acetic acid-sodium acetate buffer (pH 4.0) (40 mL), and bromine water (55.8 mL) was added thereto, and the mixture was stirred at room temperature for 4 hours. To the reaction solution, sodium hydrogen sulfate was added until the color of bromine disappeared, and then, the mixture was neutralized with sodium carbonate. The solvent was evaporated under reduced pressure until the amount of the solvent was decreased to about half, and the insoluble material was collected by filtration, washed with water and acetone in order, and then dried under reduced pressure to obtain (2R,3R,4S,5R)-2-(8-bromo-6-(dimethylamino)-9H-purin-9-yl)-5-(hydroxyethyl)tetrahydrofuran-3,4-diol (1.09 g, yield: 72%).

ESI-MS (m/z): 374 (M+1)

Step 4

(2R, R,4S,5R)-2-(8-Bromo-6-(dimethylamino)-9H-purin-9-yl)-5-( hydroxymethyl)tetrahydrofuran-3,4-diol (2.90 g, 7.75 mmol) obtained in Step 3 was suspended in acetone (39 mL), and 2,2-dimethoxypropane (4.75 mL, 38.8 mmol) and 4-toluenesulfonic acid monohydrate (1.62 g, 38.8 mol) were added thereto, and the mixture was stirred overnight at room temperature. To the reaction solution were added a saturated aqueous sodium bicarbonate solution and saturated brine, and then, the solvent was evaporated under reduced pressure until the amount of the solvent was decreased to about half. Chloroform was added thereto, and the mixture was extracted with chloroform and dried over sodium sulfate. Thereafter, the mixture was extracted with chloroform and dried over sodium sulfate. The solvent was evaporated under reduced pressure to obtain ((3aR,4R,6R,6aR)-6-(8-bromo-6-(dimethylamino)-9H-purin-9-yl)-2,2-dimethyltetrahydrofuro[3,4-d][1,3]dioxol-4-yl)methanol (1.96 g, yield: 61%) was obtained.

ESI-MS (m/z): 414 (M+1)

Step 5

((3aR,4R,6R,6aR)-6-(8-Bromo-6-(dimethylamino)-9H-purin-9-yl)-2,2-dimethyltetrahydrofuro[3,4-d][1,3]dioxol-4-yl)methanol (200 mg, 0.483 no.) obtained in Step 4 was dissolved in dichloromethane (2 mL), and 1H-tetrazole (84.6 mg, 1.21 mmol) and di-tert-butyl diisopropylphosphoramide (0.121 mL, 0.966 mmol) were added thereto, and the mixture was stirred at room temperature for 0.5 hours. The reaction solution was cooled to 0° C., and m-chloroperbenzoic acid (222 mg, 0.966 mmol) wan added thereto, and the mixture was further stirred at 0° C. for 15 minutes. To the reaction solution were added a saturated aqueous sodium bicarbonate solution and saturated brine, and the mixture was extracted with chloroform and dried over sodium sulfate. The residue obtained by evaporating the solvent under reduced pressure was purified by column chromatography (heptane/ethyl acetate) to obtain di-tert-butyl ((3aR,4R,6R,6aR)-6-(8-bromo-6-(dimethylamino)-9H-purin-9-yl)-2,2-dimethyltetrahydrofuro[3,4-d][1,3]dioxol-4-yl)methyl phosphate (209 mg, yield: 71%).

ESI-MS (m/z): 606 (M+1)

Step 6

Di-tert-butyl ((3aR,4R,6R,6aR)-6-(8-bromo-6-(dimethylamino)-9H-purin-9-yl)-2,2-dimethyltetrahydrofuro[3,4-d][1,3]dioxol-4-yl)methyl phosphate (50.0 mg, 0.082 mol)) obtained in Step 5 was dissolved in trifluoroacetic acid/water (1:1) (2 mL), and the mixture was stirred at room temperature for 3 hours. To the residue obtained by evaporating the solvent under reduced pressure, acetic acid ammonium acetate buffer (pH 5.7) was added, and then, the residue was purified by preparative HPLC (eluent: a 0.01 mol/L aqueous ammonium acetate solution/methanol) to obtain the roughly purified product. To the roughly purified product, ethanol was added, and the precipitate was collected by filtration to obtain ((2R,3S,4R,5R)-6-(8-bromo-6 (dimethylamino)-9H-purin-9-yl)-3,4-dihydroxytetrahydrofuran-2-yl)methyl phosphate (Compound I-11, 26.2 mg, yield: 70%).

$^1$H-NMR (D$_2$O, 300 MHz) δ: 8.06-7.92 (m, 1H), 5.98-5.93 (m, 1H), 5.15-5.07 (m, 1H), 4.43 (dd, J=5.9, 5.9 Hz, 1H), 4.09 (dd, J=9.8, 4.9 Hz, 1H), 3.99-3.91 (m, 1H), 3.90-3.82 (m, 1H), 3.30-3.12 (m, 6H).

ESI-MS (m/z): 454 (M+1)

REFERENCE EXAMPLE 7.1

Compound am-7

(2R,3R,4R,5R)-2-((Bis(4-methoxyphenyl)(phenyl)methoxy)methyl)-5-(8-bromo-6-(dimethylamino)-9H-purin-9-yl-4-((tert-butyldimethylsilyl)oxy)tetrahydrofuran-3-yl(2-cyanoethyl) diisopropylphosphoramidite (Compound am-7) is obtained in the same manner as in Reference Example 1.1 using (2R,3R,4S,5R)-2-(8-bromo-6-(dimethylamino)-9H-purin-9-yl)-5-(hydroxymethyl)tetrahydrofuran-3,4-diol obtained in Step 3 of Reference Example 7.0.

EXAMPLE 13

An siRNA having Compound I-11 at the 5' end of the antisense strand is synthesized in the same manner as in Example 1 using Compound am-7 obtained in Reference Example 7.1.

REFERENCE EXAMPLE 8.0

Compound I-12

Step 1

Di-tert-butyl ((3aR,4R,6R,6aR)-6-(8-bromo-6-(dimethylamino)-9H-purin-9-yl)-2,2-dimethyltetrahydrofuro[3,4-d][1,3]dioxol-4-yl)methyl phosphate (100 mg, 0.165 mmol) obtained in Step 5 of Reference Example 7.0 was dissolved in DMF (1.5 mL), and tetraethylammonium cyanide (129 mg, 0.824 mmol) was added thereto, and the mixture was stirred at 100° C. for 2 hours. After the reaction solution was cooled to room temperature, saturated brine was added thereto, and the mixture was extracted with ethyl acetate and dried over sodium sulfate. The residue obtained by evaporating the solvent under reduced pressure was purified by column chromatography (heptane/ethyl acetate) to obtain di-tert-butyl ((3aR,4R,6R,6aR)-6-(8-cyano-6-(dimethylamino)-9H-purin-9-yl)-2,2-dimethyltetrahydrofuro[3,4-d][1,3]dioxol-4-yl)methyl phosphate (52.6 mg, 58%).

ESI-MS (m/z): 558 (M+1)

Step 2

Di-tert-butyl ((3aR,4R,6R,6aR)-6-(8-cyano-6-(dimethylamino)-9H-purin-9-yl)-2,2-dimethyltetrahydrofuro[3,4-d][1,3]dioxol-4-yl)methyl phosphate (80.0 mg, 0.145 mmol) obtained in Step 2 was dissolved in trifluoroacetic acid/water (1:1) (4 mL), and the mixture was stirred at room temperature for 3 hours. The residue obtained by evaporating the solvent under reduced pressure was purified by preparative HPLC (eluent: a 0.01 mmol/L, aqueous trifluoroacetic acid solution/acetonitrile) to obtain the roughly purified product. To the roughly purified product, ethanol was added, and the precipitate was collected by filtration to obtain ((2R,3S,4R,5R)-6-(8-cyano-6-(dimethylamino)-9H-purin-9-yl)-3,4-dihydroxytetrahydrofuran-2-yl)methyl phosphate (Compound I-12, 8.4 mg, yield: 15%).

$^1$H-NMR (D$_2$O, 300 MHz) δ: 8.05 (s, 1H), 5.97 (d, J=5.9 Hz, 1H), 4.95-4.53 (m, 1H), 4.37-4.29 (m, 1H), 4.24-4.15 (m, 1H), 4.06-3.93 (m, 2H), 3.66-2.83 (m, 6H).

ESI-MS (m/z): 401 (M+0.1)

REFERENCE EXAMPLE 8.1

Compound am-8

Steps 1 to 2

8-Bromo-9-((4aR,6R,7R,7aR)-2,2-di-tert-butyl-7-(tert-butyldimethylsilyloxy)tetrahydro-4H-furo[3,2-d][1,3,2]dioxasilin-6-yl)-N,N-dimethyl-9H-purin-6-amine was obtained in the same manner as in Steps 1 to 2 of Reference Example 1.1 using (2R,3R,4S,5R)-2-(8-bromo-6-(dimethylamino)-9H-purin-9-yl)-5-(hydroxymethyl)tetrahydrofuran-3,4-diol obtained in Step 3 of Reference Example 7.0.

ESI-MS (m/z): 628 (M+1)

Step 3

8-Bromo-9-((4aR,6R,7R,7aR)-2,2-di-tert-butyl-7-(tert-butyldimethylsilyloxy)tetrahydro-4H-furo[3,2-d][1,3,2]dioxasilin-6-yl)-N,N-dimethyl-9H-purin-6-amine (10.0 mg, 0.0160 mmol) obtained in Step 2 was dissolved in DMF (1.00 mL), and sodium cyanide (7.79 tog, 0.159 mmol) and cesium fluoride (7.25 mg, 0.0480 mmol) were added thereto, and the mixture was stirred at 100° C. for 4 hours. To the reaction solution, a saturated aqueous sodium bicarbonate solution was added, and the mixture was extracted with ethyl acetate and dried over sodium sulfate. The residue obtained by evaporating the solvent under reduced pressure was purified by column chromatography (heptane/ethyl acetate) to obtain 9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-(dimethylamino)-9H-purin-8-carbonitrile (8.00 mg, yield: 44.8%) was obtained.

ESI-MS (m/z): 575 (M+1)

Steps 4 to 6

(2R,3R,4R,5R)-2-((Bis(4-methoxyphenyl)(phenyl)methoxy)methyl)-4-((tert-butyldimethylsilyl)oxy)-5-(8-cyano-6-(dimethylamino)-9H-purin-9-yl)tetrahydrofuran-3-yl(2-cyanoethyl) diisopropylphosphoramidite (Compound am-s) is obtained in the same manner as in Steps 3 to 5 of Reference Example 1.1 using 9-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-(dimethylamino)-9H-purin-8-carbonitrile obtained in Step 3.

EXAMPLE 14

An siRNA having Compound I-12 at the 5' end of the antisense strand is synthesized in the same manner as in Example 1 using Compound am-8 obtained in Reference Example 8.1.

REFERENCE EXAMPLE 9.0
Compound I-13

((2R,3S,4R,5R)-5-(6-Iodo-2,4-dioxo-3,4-dihydropyrimidin-1(2H)-yl)-3,4-dihydroxytetrahydrofuran-2-yl)methyl phosphate triethylamine (Compound I-13) was obtained in the same manner as in Steps 3 to 5 of Reference Example 1.0 using commercially available 1-((2R,3R,4S,5R)-3,4-dihydroxy-5-(hydroxymethyl)tetrahydrofuran-2-yl)-6-iodopyrimidine-2,4(1H,3H)-dione (866 mg, 2.34 mmol).

$^1$H-NMR (D$_2$O, 300 MHz) δ: 6.52 (s, 1H), 5.92 (d, J=3.3 Hz, 1H), 4.69-4.60 (m, 1H), 4.33 (t, J=6.8 Hz, 1H), 4.02-3.86 (m, 3H), 3.07 (q, J=7.3 Hz, 6H), 1.15 (t, J=7.3 Hz, 9H).

ESI-MS (m/z): 451 (M+1)

REFERENCE EXAMPLE 9.1

Compound am-9

(2R,3R,4R,5R)-2-((Bis(4-methoxyphenyl)(phenyl)methoxy)methyl)-4-((tert-butyldimethylsilyl)oxy)-5 (6*-iodo-2,4-dioxo-3,4-dihydropyrimidin-1(2H)-yl)tetrahydrofuran-3-yl(2-cyanoethyl) diisopropylphosphoramidite (Compound am-9) is obtained in the same manner as in Reference Example 1.1 using commercially available 1-((2R,3R,4S,5R)-3,4-dihydroxy-5-(hydroxymethyl)tetrahydrofuran-2-yl)-6-iodopyrimidine-2,4(1H,3H)-dione.

EXAMPLE 15

An siRNA having Compound I-13 at the 5' end of the antisense strand is synthesized in the same manner as in Example 1 using Compound am-9 obtained in Reference Example 9.1.

REFERENCE EXAMPLE 10.0

Compound I-14

Step 1

5-Bromo-1-((3aR,4R,6R,6aR)-6-(hydroxymethyl)-2,2-dimethyltetrahydrofuro[3,4-d][1,3]dioxol-4-yl) pyrimidine-2,4(1H,3H)-dione (2.58 g, yield: 69%) was obtained in the same manner as in Step 3 of Reference Example 1.0 using commercially available 5-bromo-1-((2R,3R,4S,5R)-3,4-dihydroxy-5-(hydroxymethyl)tetrahydrofuran-2-yl)pyrimidine-2,4(1H,3H)-dione (3.34 g, 10.3 mmol).

ESI-MS (m/z): 363 (M+1)

Step 2

5-Bromo-1-((3aR,4R,6R,6aR)-6-(hydroxymethyl)-2,2-dimethyltetrahydrofuro[3,4-d][1,3]dioxol-4-yl)pyrimidine-2,4(1H,3H)-dione (200 mg, 0.551 mmol) obtained in Step 1 and tetrakis(triphenylphosphine)palladium (63.6 mg, 0.055 mmol) were dissolved in 1,4-dioxane, and tributyl(2-pyridyl)tin (0.62 mL, 1.93 mmol) was added thereto, and the mixture was stirred overnight at 110° C. After the reaction mixture was cooled to room temperature, a saturated aqueous sodium bicarbonate solution was added thereto, and the mixture was filtered through Presep (registered trademark, diatomaceous earth, Granular Type M, 4.5 g/25 mL), and then, the solvent was evaporated under reduced pressure. The residue obtained was purified by column chromatography (chloroform/methanol) to obtain 1-((3aR,4R,6R,6aR)-6-(hydroxymethyl)-2,2-dimethyltetrahydrofuro[3,4-d][1,3]dioxol-4-yl)-5-(pyridin-2-yl)pyrimidine-2,4(1H,3H)-dione (45.2 mg, yield; 23%).

ESI-MS (m/z): 362 (M+1)

Steps 3 to 4

((2R,3S,4R,5R)-5-(2,4-Dioxo-5-(pyridin-2-yl)-3,4-dihydropyrimidin-1(2H)-yl)-3,4-dihydroxytetrahydrofuran 2-yl) methyl phosphate (Compound I-14) was obtained in the same manner as in Steps 4 to 5 of Reference Example 1.0 using 1-((3aR,4R,6R,6aR)-6-(hydroxymethyl)-2,2-dimethyltetrahydrofuro[3,4-d][1,3]dioxol-4-yl)-5-(pyridin-2-yl)pyrimidine-2,4(1H,3H)-dione obtained in Step 2.

$^1$H-NMR (D$_2$O, 300 MHz) δ: 8.66 (s, 1H), 8.56 (d, J=5.5 Hz, 1H), 8.40 (t, J=7.9 Hz, 1H), 8.20 (d, J=8.4 Hz, 1H), 7.77 (t, J=6.8 Hz, 1H), 5.92 (d, J=4.0 Hz, 1H), 4.35 (t, J=4.2 Hz, 1H), 4.27-4.26 (m, 2H), 4.15 (dd, J=12.1, 2.9 Hz, 1H), 4.04 (dd, J=13.0, 5.7 Hz, 1H).

ESI MS (m/z): 402 (M+1)

REFERENCE EXAMPLE 10.1

Compound am-10

Step 1

1-((2R,3R,4S,5R)-3,4-Dihydroxy-5-(hydroxymethyl)tetrahydrofuran-2-yl)-5-(pyridin-2-yl)pyrimidine 2,4(1H,3H)-dione is obtained in the same manner as in Step 1 of Reference Example 6.1 using 1-((3aR,4R,6R,6aR)-6-(hydroxymethyl)-2,2-dimethyltetrahydrofuro[3,4-d][1,3]dioxol-4-yl)-5-(pyridin-2-yl)pyrimidine-2,4(1H, 3H)-dione obtained in Step 2 of Reference Example 10.0.

Step 2

(2R,3R,4R,5R)-2-((Bis(4-methoxyphenyl)(phenyl)methoxy)methyl)-4-((tert-butyldimethylsilyl)oxy)-5-(2,4-dioxo-5-(pyridin-2-yl)-3,4-dihydropyrimidin-1(2H)-yl)tetrahydrofuran-3-yl (2-cyanoethyl) diisopropylphosphoramidite (Compound am-10) is obtained in the same manner as in Reference Example 1.1 using 1-((2R,3R,4S,5R)-3,4-dihydroxy-5-(hydroxymethyl)tetrahydrofuran-2-yl)-5-(pyridin-2-yl)pyrimidine-2,4(1H,3H)-dione.

EXAMPLE 16

An siRNA having Compound I-14 at the 5' end of the antisense strand is synthesized in the same manner as in Example 1 using Compound am-10 obtained in Reference Example 10.1.

REFERENCE EXAMPLE 11.0

Compound I-15

((2R,3S,4R,5R)-3,4-Dihydroxy-5-(5-(oxazol-2-yl)-2,4-dioxo-3,4-dihydropyrimidin-1(2H)-yl)tetrahydrofuran-2-yl)methyl phosphate (Compound I-15) was obtained in the same manner as in Steps 2 to 4 of Reference Example 10.0 using 2-(tri-n-butylstannyl)oxazole.

$^1$H-NMR (D$_2$O, 300 MHz) δ: 8.52 (s, 1H), 7.84 (s, 1H), 7.19 (s,1H), 5.93 (d, J=4.9 Hz, 1H), 4.36 (t, J=4.9 Hz, 1H), 4.28-4.24 (m, 2H), 4.11 (dq, J=11.7, 2.0 Hz, 1H), 4.03 (dq, J=11.7, 2.6 Hz, 1H).

REFERENCE EXAMPLE 11.1

Compound am-11

(2R,3R,4R,5R)-2-((Bis(4-methoxyphenyl)(phenyl)methoxy)methyl)-4-((tert-butyldimethylsilyl)oxy)-5-(5-(oxazol-2-yl)-2,4-dioxo-3,4-dihydropyrimidin-1(2H)-yl)tetrahydrofuran-3-yl(2-cyanoethyl)diisopropylphosphoramidite (Compound am-11) is obtained in the same manner as in Reference Example 10.1 using 1-((3aR,4R,6R,6aR)-6-(hydroxymethyl)-2,2-dimethyltetrahydrofuro[3,4-d][1,3]dioxol-4-yl)-5-(oxazol-2-yl) pyrimidine-2,4(1H,3H)-dione synthesized in the same manner as in Step 2 of Reference Example 10.0 using 2-(tri-n-butylstannyl)oxazole.

EXAMPLE 17

An siRNA having Compound I-15 at the 5' end of the antisense strand is synthesized in the same manner as in Example 1 using Compound am-11 obtained in Reference Example 11.1.

REFERENCE EXAMPLE 12.0

Compound I-16

Step 1

(2R,3R,4R,5R)-2-((Benzoyloxy)methyl)-5-(5-iodo-2,4-dioxo-3,4-dihydropyrimidin-1(2H)-yl)tetrahydrofuran-3,4-diyl dibenzoate was obtained in the same manner as in Step 1 of Reference Example 1.0 using commercially available 5-iodopyrimidine-2,4(1H,3H)-dione.

ESI-MS (m/z): 683 (M+1)

Step 2

1,4-Dioxane (3 mL) was added to (2R,3R,4R,5R)-2-((benzoyloxy)methyl)-5-(5-iodo-2,4-dioxo-3,4-dihydropyrimidin-1 (2H)-yl)tetrahydrofuran-3,4-diyl dibenzoate (200 mg, 0.293 mmol) obtained in Step 1, (4-methoxyphenyl)boronic acid (134.0 mg, 0.879 mmol), 1,1'-bio(diphenylphosphino)ferrocene-palladium(II) dichloride-dichloromethane complex (23.9 mg, 0.029 mmol), and a 2 M aqueous cesium carbonate solution (0.6 mL), and the mixture was stirred at 120° C. for 1 hour. After the reaction solution was cooled to room temperature, a saturated aqueous sodium bicarbonate solution was added thereto, and the mixture was filtered through Presep (registered trademark, diatomaceous earth, Granular Type M, 4.5 g/25 mL), and then, the solvent was evaporated under reduced pressure. The residue obtained was purified by column chromatography (chloroform/methanol) to obtain (2R,3R,4R,5R)-2-((benzoyloxy)methyl)-5-(5-(4-methoxyphenyl)-2,4-dioxo-3,4-dihydropyrimidin-1(2H)-yl)tetrahydrofuran-3,4-diyl dibenzoate (118 mg, yield: 61%) was obtained.

ESI-MS (m/z): 663 (M+1)

Step 3

((2R,3S,4R,5R)-3,4-Dihydroxy-5-(5-(4-methoxyphenyl)-2,4-dioxo-3,4-dihydropyrimidin-1(2H)-yl)tetrahydrofuran-2-yl)methyl phosphate (Compound I-16) was obtained in the same manner as in Steps 2 to 5 of Reference Example 1.0 using (2R,3R,4R,5R)-2-((benzoyloxy)methyl)-5-(5-(4-methoxyphenyl)-2,4-dioxo-3,4-dihydropyrimidin-1(2H)-yl) tetrahydrofuran-3,4-diyldibenzoate obtained in Step 2.

$^1$H-NMR (D$_2$O, 300 MHz) δ: 7.77 (s, 1H), 7.42 (d, J=8.8 Hz, 2H), 7.01 (d, J=8.8 Hz, 2H), 5.97 (d, J=5.5 Hz, 1H), 4.39 (t, J=5.9 Hz, 1H), 4.27 (t, J=4.4 Hz, 1H), 4.22-4.21 (m, 1H), 4.04-4.02 (m, 2H), 3.81 (s, 3H).

ESI-MS (m/z): 431 (M+1)

REFERENCE EXAMPLE 12.1

Compound am-12

(2R,3R,4R,5R)-2-((Bis(4-methoxyphenyl)(phenyl)methoxy)methyl)-4-((tert-butyldimethylsilyl)oxy)-5-(5-(4-methoxyphenyl)-2,4-dioxo-3,4-dihydropyrimidin-1(2H)-yl)tetrahydrofuran-3-yl (2-cyanoethyl) diisopropylphosphoramidite (Compound am-12) is obtained in the same manner as in Reference Example 1.1 using (2R,3R,4R,5R)-2-((benzoyloxy)methyl)-5-(5-(4-methoxyphenyl)-2,4-dioxo-3,4-dihydropyrimidin-1(2H)-yl)tetrahydrofuran-3,4-diyl dibenzoate obtained in Step 2 of Reference Example 12.0.

EXAMPLE 18

An siRNA having Compound I-16 at the 5' end of the antisense strand is synthesized in the same manner as in Example 1 using Compound am-12 obtained in Reference Example 12.1.

REFERENCE EXAMPLE 13.0

Compound I-17

Step 1

Di-tert-butyl ((3aR,4R,6R,6aR)-6-(5-bromo-2,4-dioxo-3,4-dihydropyrimidin-1(2H)-yl)-2,2-dimethyltetrahydrofuro[3,4-d][1,3]dioxol-4-yl)methyl phosphate was obtained in the same manner as in Step 4 of Reference Example 1.0 using 5-bromo-1-((3aR,4R,6R,6aR)-6-(hydroxymethyl)-2,2-dimethyltetrahydrofuro[3,4-d][1,3]dioxol-4-yl)pyrimidine-2,4(1H, 3H)-dione obtained in Step 1 of Reference Example 10.0.

ESI-MS (m/z): 555 (M+1)

Step 2

Di-tert-butyl ((3aR,4R,6R,6aR)-6-(5-bromo-2,4-dioxo-3,4-dihydropyrimidin-1(2H)-yl)-2,2-dimethyltetrahydrofuro[3,4-d][1,3]dioxol-4-yl)methyl phosphate (200 mg, 0.360 mmol) obtained in Step 1 was dissolved in DMF (7 mL), and sodium cyanide (88.0 mg, 1.801 mmol) wan added thereto, and the mixture wan stirred overnight at room temperature. To the reaction solution was added a saturated aqueous sodium bicarbonate solution, and the mixture was extracted with ethyl acetate and dried over sodium sulfate. The residue obtained by evaporating the solvent under reduced pressure was purified by column chromatography (heptane/ethyl acetate) to obtain di-tert-butyl ((3aR,4R,6R,6aR)-6-(6-cyano-2,4-dioxo-3,4-dihydropyrimidin-1(2H)-yl)-2,2-dimethyltetrahydrofuro[3,4-d][1,3]dioxol-4-yl)methyl phosphate (150 mg, yield: 83%).

ESI-MS (m/z): 502 (M+1)

Step 3

((2R,3S,4R,5R)-5-(6-Cyano-2,4-dioxo-3,4-dihydropyrimidin-1(2H)-yl)-3,4-dihydroxytetrahydrofuran-2-yl)methyl phosphate (Compound I-17) was obtained in the same manner as in Step 5 of Reference Example 1.0 using di-tert-butyl ((3aR,4R,6R,6aR)-6-(6-cyano-2,4-dioxo-3,4-dihydropyrimidin-1(2H)-yl)-2,2-dimethyltetrahydrofuro[3,4-d][1,3]dioxol-4-yl)methyl phosphate obtained in Step 2.

$^1$H-NMR (D$_2$O, 300 MHz) δ: 6.51 (d, J=0.7 Hz, 1H), 5.81 (d, J=4.0 Hz, 1H), 4.28 (t, J=6.2 Hz, 1H), 4.01-3.95 (m, 4H).

ESI-MS (m/z): 350 (M+1)

REFERENCE EXAMPLE 13.1

Compound am-13

Steps 1 to 2

5-Bromo-1-((4aR,6R,7R,7aR)-2,2-di-tert-butyl-7-((tert-butyldimethylsilyl)oxy)tetrahydro-4H-furo[3,2-d][1,3,2]dioxasilin-6-yl)pyrimidine-2,4(1H, 3H)-dione was obtained in the same manner as in Steps 1 to 2 of Reference Example 1.1 using commercially available 5-bromo-1-((2R,3R,4S,5R)-3,4-dihydroxy-5-(hydroxymethyl)tetrahydrofuran-2-yl)pyrimidine-2,4(1H,3H)-dione.

ESI-MS (m/z): 577 (M+1)

Step 3

3-((4aR,6R,7R,7aR)-2,2-Di-tert-butyl-7-((tert-butyldimethylsilyl)oxy)tetrahydro-4H-furo[3,2-d][1,3,2]dioxasilin-6-yl)-2,6-dioxo-1,2,3,6-tetrahydropyrimidine-4-carbonitrile was obtained in the same manner as in Step 2 of Reference Example 13.0 using 5-bromo-1-((4aR,6R,7R,7aR)-2,2-di-tert-butyl-7-((tert-butyldimethylsilyl)oxy)tetrahydro-4H-furo[3,2-d][1,3,2]dioxasilin-6-yl)pyrimidine-2,4(1H,3H)-dione obtained in Step 2.

ESI-MS (m/z): 524 (M+1)

Step 4

(2R,3R,4R,5R)-2-((Bis(4-methoxyphenyl)(phenyl)methoxy)methyl)-4-((tert-butyldimethylsilyl)oxy)-5-(6-cyano-2,4-dioxo-3,4-dihydropyrimidin-1(2H)-yl)tetrahydrofuran-3-yl(2-cyanoethyl) diisopropylphosphoramidite (Compound am-13) was obtained in the same manner as in Steps 3 to 5 of Reference Example 1.1 using 3-((4aR,6R,7R,7aR)-2,2-di-tert-butyl-7-((tert-butyldimethylsilyl)oxy)tetrahydro-4H-furo[3,2-d][1,3,2]dioxasilin-6-yl)-2,6-dioxo-1,2,3,6-tetrahydropyrimidine-4-carbonitrile obtained in Step 3.

$^1$H-NMR (CDCl$_3$, 500 MHz) δ: 7.47-6.78 (m, 13H), 6.27 (6.26) (s, 1H), 5.84 (m, 1H), 4.95 (4.89) (m, 1H), 4.35-4.19 (m, 2H), 3.96-3.27 (m, 12H), 2.31 (2.59) (m, 2H), 1.19-1.06 (m, 12H), 0.87 (0.88) (s, 9H), 0.06 (0.08) (s, 3H), 0.01 (s, 3H).

EXAMPLE 19

An siRNA having Compound I-17 as X at the 5' end of the antisense strand of 454-Xu shown in Table 24 below was synthesized in the same manner as in Example 1 using Compound am-13 obtained in Reference Example 13.1.

MALDI-TOF/MS (antisense strand): theoretical value: 6691.86 (M-H), actual value: 6691.25

REFERENCE EXAMPLE 14.0

Compound I-18

Step 1

((3aR,4R,6R,6aR)-2,2-Dimethyl-6-(6-((E)-styryl)-9H-purin-9-yl)tetrahydrofuro[3,4-d][1,3]dioxol-4-yl)methanol (249 mg, 0.631 mmol) obtained in Step 2 of Reference Example 6.0 was dissolved in chloroform (6.00 mL), and imidazole (86 mg, 1.26 mmol) and tert-butyldimethylsilyl chloride (105 mg, 0.694 mmol) were added thereto under ice cooling, and the mixture was stirred at room temperature for 3 hours. Thereafter, imidazole (86 mg, 1.26 mmol) and tert-butyldimethylsilyl chloride (105 mg, 0.694 mmol) were added thereto under ice cooling, and the mixture was further stirred at room temperature for 1 hour. The residue obtained by evaporating the solvent under reduced pressure was purified by column chromatography (heptane/ethyl acetate) to obtain 9-((3aR,4R,6R,6aR)-6-((tert-butyldimethylsilyloxy)methyl)-2,2-dimethyltetrahydrofuro[3,4-d][1,3]dioxol-4 yl)-6-((E)-styryl)-9H-purine (310 mg, 97.0%).

ESI-MS (m/z): 509 (M+1)

Step 2

9-((3aR,4R,6R,6aR)-6-((Tert-butyldimethylsilyloxy)methyl)-2,2-dimethyltetrahydrofuro[3,4-d][1,3]dioxol-4-yl)-6-((E)-styryl)-9H-purine (200 mg, 0.393 mmol) obtained in Step 1 was dissolved in THF (3.00 mL), and lithium diisopropylamide (0.393 mL, 0.786 mmol) was added thereto at −78° C. After stirring the mixture for 30 minutes, the solution obtained by dissolving 1,2-dibromo-1,1,2,2-tetrachloroethane (384 mg, 1.18 mmol) in THF (2.00 mL) was added thereto at −78° C. Thereafter, the temperature of the mixture was raised to room temperature over 1 hour while stirring. To the reaction mixture, a saturated aqueous sodium bicarbonate solution was added, and the mixture was extracted with ethyl acetate and dried over anhydrous sodium sulfate. The residue obtained by evaporating the solvent under reduced pressure was purified by column chromatography (heptane/ethyl acetate) to obtain 8-bromo-9-((3aR,4R,6R,6aR)-6-((tert-butyldimethylsilyloxy)

methyl)-2,2-dimethyltetrahydrofuro[3,4-d][1,3]dioxol-4-yl)-6-((E)-styryl)-9H-purine (198 mg, 86.0%).

ESI-MS (m/z): 587 (M+1)

Step 3

8-Bromo-9-((3aR,4R,6R,6aR)-6-((tert-butyldimethylsilyloxy)methyl)-2,2-dimethyltetrahydrofuro[3,4-d][1,3]dioxol-4-yl)-6-((E)-styryl)-9H-purine (198 mg, 0.337 mmol) obtained in Step 2 was dissolved in trifluoroacetic acid/water (1:1) (2 mL), and the mixture was stirred at room temperature for 2 hours. The residue obtained by evaporating the solvent under reduced pressure wan purified by column chromatography (heptane/ethyl acetate) to obtain (2R,3R,4S,5R)-2-(8-bromo-6-((E)-styryl)-9H-purin-9-yl)-5-(hydroxy methyl)tetrahydrofuran-3,4-diol (140 mg, 96.0%).

ESI-MS (m/z): 433 (M+1)

Step 4

((3aR,4R,6R,6aR)-6-(8-Bromo-6-((E)-styryl)-9H-purin-9-yl)-2,2-dimethyltetrahydrofuro[3,4-d][1,3]dioxol-4-yl)methanol (66.0 mg, 43.2%) was obtained in the same manner as in Step 3 of Reference example 1.0 using (2R,3R,4S,5R)-2-(8-bromo-6-((E)-styryl)-9H-purin-9-yl)-5-(hydroxy methyl)tetrahydrofuran-3,4-diol (140 mg, 0.323 mmol) obtained in Step 3.

ESI-MS (m/z): 473 (M+1)

Steps 5 to 6

((2R,3S,4R,5R)-5-(8-Bromo-6-((E)-styryl)-9H-purin-9-yl)-3,4-dihydroxytetrahydrofuran-2-yl)methyl phosphate (Compound I-18, 68.5 mg, 75.0%) was obtained in the same manner as in Steps 3 to 4 of Reference Example 6.0 using ((3aR,4R,6R,6aR)-6-(8-Bromo-6-((E)-styryl)-9H-purin-9-yl)-2,2-dimethyltetrahydrofuro[3,4-d][1,3]dioxol-4-yl)methanol (65.0 mg, 0.137 mmol) obtained in Step 4.

$^1$H-NMR (D$_2$O, 400 MHz) δ: 8.45 (1H, s), 7.54 (1H, d, J=15.6 Hz), 7.24-7.17 (2H, m), 7.11-7.00 (3H, m), 6.95 (1H, d, J=15.6 Hz), 5.96 (1H, d, J=4.9 Hz), 5.18 (1H, dd, J=5.4, 5.4 Hz), 4.54 (1H, dd, J=5.4, 5.4 Hz), 4.19-4.13 (1H, m), 4.12-3.95 (2H, m).

ESI-MS (m/z): 513 (M+1)

REFERENCE EXAMPLE 14.1

Compound am-14

3-((2R,3R,4R,5R)-2-((Bis(4-methoxyphenyl)(phenyl)methoxy)methyl)-5-(8-bromo-6-((E)-styryl)-9H-purin-9-yl)-4-(tert-butyldimethylsilyloxy)tetrahydrofuran-3-yl(2-cyanoethyl) diisopropylphosphoramidite (Compound am-14) is obtained in the same manner as in Reference Example 1.1 using (2R,3R,4S,5R)-2-(8-bromo-6-((E)-styryl)-9H-purin-9-yl)-5-(hydroxy methyl)tetrahydrofuran-3,4-diol obtained in Step 3 of Reference Example 14.0.

EXAMPLE 20

An siRNA having Compound I-18 at the 5' end of the antisense strand is synthesized in the same manner as in Example 1 using Compound am-14 obtained in Reference Example 14.1.

REFERENCE EXAMPLE 15.0

Compound I-19

((2R,3S,4R,5R)-5-(5,6-Dimethyl-2,4-dioxo-3,4-dihydrothieno[2,3-d]pyrimidin-1 (2H)-yl)-3,4-dihydroxytetrahydrofuran-2-yl)methyl phosphate (Compound I-19) triethylammonium salt was obtained in the same manner as in Reference Example 1.0 using commercially available 5,6-dimethylthieno[2,3-d]pyrimidine-2,4(1H,3H)-dione.

$^1$H-NMR (D$_2$O, 300 MHz) δ: 6.10 (d, J=5.5 Hz, 1H), 4.75-4.73 (m, 1H), 4.40 (t, J=5.7 Hz, 10), 4.24-4.14 (m, 3H), 2.32 (s, 3H), 2.31 (s, 3H).

ESI-MS (m/z): 411 (M+1)

REFERENCE EXAMPLE 15.1

Compound am-15

(2R,3R,4R,5R)-2-((Bis(4-methoxyphenyl)(phenyl)methoxy)methyl)-4-(tert-butyldimethylsilyloxy)-5-(5,6-dimethyl-2,4-dioxo-3,4-dihydrothieno[2,3-d]pyrimidin-1 (2H)-yl)tetrahydrofuran-3-yl 2-cyanoethyl diisopropylphosphoramidite (Compound am-15) was obtained in the same manner as in Reference Example 1.1 using commercially available 5,6-dimethylthieno[2,3-d]pyrimidine-2,4(1H,3H)-dione.

$^1$H-NMR (CDCl$_3$, 500 MHz) δ: 7.62 (s, 1H), 7.50-6.78 (m, 13H), 5.98 (m, 1H), 4.92 (m, 1H), 4.34-4.25 (m, 2H), 4.00-3.34 (m, 121), 2.29 (2.64) (m, 2H), 2.35 (s, 3H), 2.13 (s, 3H), 1.23-1.03 (m, 12H), 0.83 (0.84) (s, 9H), 0.02 (d, J=6.0 Hz, 3H), −0.10 (d, J=5.0 Hz, 3H).

EXAMPLE 21

An siRNA (referred to as di-Me-thienyl-dU) having Compound I-19 as X at the 5' end of the antisense strand of 454-Xu shown in Table 24 below was synthesized in the same manner as in Example 1 using Compound am-15 obtained in Reference Example 15.1.

MALDI-TOP/MS (antisense strand): theoretical value: 6750.99 (M-H), actual value: 6754.34

REFERENCE EXAMPLE 16.0

Compound I-20

Step 1

((3aR,4R,6R,6aR)-6-(6-(3-Isopropylphenyl)-9H-purin-9yl)-2,2-dimethyltetrahydrofuro[3,4-d][1,3]dioxol-4-yl)methanol (167 mg, 133%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and 3-isopropylphenylboronic acid (100 mg, 0.612 mmol).

ESI-MS (m/z): 411 (M+1)

Step 2

Di-tert-butyl ((3aR,4R,6R,6aR)-6-(6-(3-isopropylphenyl)-9H-purin-9-yl)-2,2-dimethyltetrahydrofuro[3,4-d][1,3]dioxol-4-yl)methyl phosphate (96.2 mg, 52.0%) was obtained in the same manner as in Step 3 of Reference Example 6.0 using ((3aR,4R,6R,6aR)-6-(6-(3-isopropylphenyl)-9H-purin-9-yl)-2,2-dimethyltetrahydrofuro[3,4-d][1,3]dioxol-4-yl)methanol (126 mg, 0.307 mmol) obtained in Step 1.

ESI-MS (m/z): 603 (M+1)

Step 3

Di-tert-butyl ((3aR,4R,6R,6aR)-6-(6 (3-isopropylphenyl)-9H-purin-9-yl)-2,2-dimethyltetrahydrofuro[3,4-d][1,3]dioxol-4-yl)methyl phosphate (96.0 mg, 0.159 mmol) obtained in Step 1 was dissolved in trifluoroacetic acid/water (1:1) (2 mL), and the mixture was stirred at room temperature for 3 hours. The residue obtained by evaporating the solvent under reduced pressure was purified by preparative HPLC (eluent: 0.01 mmol/L acetic acid-triethylamine buffer (pH 6.5)/acetonitrile) to obtain ((2R,3S,4R,5R)-3,4-dihydroxy-5-(6-(3-isopropylphenyl)-9H-purin-9-yl)tetrahydrofuran-2-yl)methyl phosphate (Compound I-20) triethylammonium salt (70.0 ing, 80.0%).

¹H-NMR (D₂O, 300 MHz) δ: 8.72 (2H, d, J=7.0 Hz), 7.97 (1H, s), 7.92-7.83 (1H, m), 7.43-7.33 (2H, m), 6.14 (1H, d, J=5.5 Hz), 4.73-4.64 (14H, m), 4.44-4.38 (1H, m), 4.32-4.25 (1H, m), 4.08-3.93 (2H, s), 3.06 (11H, q, J=7.3 Hz), 2.94-2.81 (1H, m), 1.20-1.08 (22H, m).

ESI-MS (m/z): 451 (M+1)

REFERENCE EXAMPLE 16.1

Compound am-16

(2R,3R,4R,5R)-2-((Bis(4-methoxyphenyl)(phenyl)methoxy)methyl)-4-(tert-butyldimethylsilyloxy)-5-(6-(3-isopropylphenyl)-9H-purin-9-yl)tetrahydrofuran-3-yl 2-cyanoethyl diisopropylphosphoramidite (Compound am-16) is obtained in the same manner as in Reference Example 6.1 using ((3aR,4R,6R,6aR)-6-(6-(3-isopropylphenyl)-9H-purin-9-yl)-2,2-dimethyltetrahydrofuro[3,4-d][1,3]dioxol-4-yl)methanol obtained in Step 1 of Reference Example 16.0.

EXAMPLE 22

An siRNA having Compound I-20 at the 5' end of the antisense strand is synthesized in the same manner as in Example 1 using Compound am-16 obtained in Reference Example 16.1.

REFERENCE EXAMPLE 17.0

Compound I-21

Step 1
((3aR,4R,6R,6aR)-2,2-Dimethyl-6-(6-(naphthalen-2-yl)-9H-purin-9-yl)tetrahydrofuro[3,4-d][1,3]dioxol-4-yl)methanol (14.1 mg, 114%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and 2-naphthaleneboronic acid (105 mg, 0.612 mmol).

ESI-MS (m/z): 419 (M+1)
Step 2
Di-tert-butyl ((3aR,4R,6R,6aR)-2,2-dimethyl-6-(6-(naphthalen-2-yl)-9H-purin-9-yl)tetrahydrofuro[3,4-d][1,3]dioxol-4-yl)methyl phosphate (90.0 mg, 48.2%) was obtained in the same manner as in Step 3 of Reference Example 6.0 using ((3aR,4R,6R,6aR)-2,2-dimethyl-6-(6-(naphthalen-2-yl) 9H-purin-9-yl)tetrahydrofuro[3,4-d][1,3]dioxol-4-yl)methanol (128 mg, 0.306 mmol) obtained in Step 1.

ESI-MS (m/z): 611 (M+1)
Step 3
((2R,3S,4R,5R)-3,4-Dihydroxy-5-(6-(naphthalen-2-yl)-9H-purin-9-yl)tetrahydrofuran-2-yl)methyl phosphate (Compound I-21) triethylammonium salt (20.0 mg, 29.61) was obtained in the same manner as in Step 5 of Reference Example 1.0 using di-tert-butyl ((3aR,4R,6R,7aR)-2,2-dimethyl-6-(6-(naphthalen-2-yl)-9H-purin-9-yl)tetrahydrofuro[3,4-d][1,3]dioxol-4-yl)methyl phosphate (77.0 mg, 0.126 mmol) obtained in Step 2.

¹H-NMR (D₂O, 400 MHz) δ: 8.30 (1H, s), 8.05 (1H, s), 7.80 (1H, s), 7.55-7.40 (1H, m), 7.27-6.92 (5H, m), 5.73 (1H, s), 4.52-4.10 (3H, m), 4.15-3.92 (2H, m), 3.06-2.96 (6H, m), 1.16-1.04 (9H, m).

REFERENCE EXAMPLE 17.1

Compound am-17

Steps 1 to 2
6-Chloro-9-((4aR,6R,7R,7aS)-2,2-di-tort-butyl-7-(tert-butyldimethylsilyloxy)tetrahydro-4H-furo[3,2-d][1,3,2]dioxasilin-6-yl)-9H-purine was obtained in the same manner as in Steps 1 to 2 of Reference Example 1.1 using commercially available (2R,3R,4S,5R)-2-(6-chloro-9H-purin-9-yl)-5-(hydroxymethyl)tetrahydrofuran-3,4-diol.

ESI-MS (m/z): 541 (M+1)
Step 3
9-((4aR,6R,7R,7aS)-2,2-Di-tert-butyl-7-(tert-butyldimethylsilyloxy)tetrahydro-4H-furo[3,2-d][1,3,2]dioxasilin-6-yl)-6-(naphthalen-2-yl)-9H-purine was obtained in the same manner as in Step 1 of Reference Example 17.0 using 6-chloro-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine obtained in Step 2.

ESI-ME (m/z): 633 (M+1)
Steps 4 to 6
(2R,3R,4R,5R)-2-((Bis(4-methoxyphenyl)(phenyl)methoxy)methyl)-4-(tert-butyldimethylsilyloxy)-5-(6-(naphthalen-2-yl)-9H-purin-9-yl)tetrahydrofuran-3-yl 2-cyanoethyl diisopropylphosphoramidite (Compound am-17) was obtained in the same manner as in Steps 3 to 5 of Reference Example 1.1 using 9-((4aR,6R,7R,7aS)-2,2-di-tert-butyl-7-(tert-butyldimethylsilyloxy)tetrahydro-4H-furo[3,2-d][1,3,2]dioxasilin-6-yl)-6-(naphthalen-2-yl)-9H-purine obtained in Step 3.

¹H-NMR (CDCl₃, 500 MHz) δ: 9.43 (m, 1H), 8.96 (m, 1H), 8.88 (m, 1H), 8.40 (m, 1H), 8.08 (m, 1H), 8.02 (m, 1H), 7.91 (m, 1H), 7.59-7.52 (m, 2H), 7.52-6.81 (m, 13H), 6.19 (6.13) (m, 1H), 5.11 (m, 1H), 4.50-4.38 (m, 2H), 4.02-3.32 (m, 12H), 2.67 (2.32) (m, 2H), 1.23-1.05 (m, 12H), 0.76 (0.77) (s, 9H), −0.03 (0.00) (s, 3H), −0.19 (−0.17) (s, 3H).

EXAMPLE 23

An siRNA (referred to as 6-napht-2-yl-dPu) having Compound I-21 as X at the 5' end of the antisense strand of 454-Xa shown in Table 24 below was synthesized in the same manner as in Example 1 using Compound am-37 obtained in Reference Example 17.1.

MALDI-TOF/MS (antisense strand): theoretical value: 6801.03 (M-H), actual value: 6805.40

REFERENCE EXAMPLE 18.0

Compound I-22

Step 1
((3aR,4R,6R,6aR)-6-(6-(3-Formylphenyl)-9H-purin-9-yl)-2,2-dimethyltetrahydrofuro[3,4-d][1,3]dioxol-4-yl)methanol (216 mg, 89%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (200 mg, 0.612 mmol) obtained in Step 1 of Reference Example 6.0 and 3-formylphenylboronic acid (184 mg, 1.22 mmol).

ESI-MS (m/z): 397 (M+1)

Step 2

Di-tert-butyl ((3aR,4R,6R,6aR)-6-(6-(3-formylphenyl)-9H-purin-9-yl)-2,2-dimethyltetrahydrofuro[3,4-d][1,3]dioxol-4-yl)methyl phosphate (35.0 mg, 11.0%) was obtained in the same manner as in Step 3 of Reference Example 6.0 using ((3aR,4R,6R,6aR)-6-(6-(3-formylphenyl)-9H-purin-9-yl)-2,2-dimethyltetrahydrofuro[3,4-d][1,3]dioxol-4-yl)methanol (215 mg, 0.542 mmol) obtained in Step 1.

ESI-MS (m/z): 589 (M+1)

Step 3

((2R,3S,4R,5R)-3,4-Dihydroxy-5-(6-(3-formylphenyl)-9H-purin-9-yl)tetrahydrofuran-2-yl)methyl phosphate (Compound I-22, 20.0 mg, 29.6%) was obtained in the same manner as in Step 5 of Reference Example 1.0 using di-tert-butyl ((3aR,4R,6R,6aR)-6-(6-(3-formylphenyl)-9H-purin-9-yl)-2,2-dimethyltetrahydrofuro[3,4-d][1,3]dioxol-4-yl)methyl phosphate (33.0 mg, 0.0560 mmol) obtained in Step 1.

$^1$H-NMR (D$_2$O, 300 MHz) δ: 9.93 (1H, s), 8.88 (1H, s), 8.76 (1H, s), 8.67-8.60 (1H, m), 8.47-8.40 (1H, m), 8.06-7.99 (1H, m),7.74-7.66 (1H, m), 6.20 (1H, d, J=5.5 Hz), 4.76-4.68 (2H, m), 4.46-4.41 (1H, m), 4.34-4.29 (1H, m), 4.12-4.00 (2H, m).

ESI-MS (m/z): 437 (M+1)

REFERENCE EXAMPLE 18.1

Compound am-18

(2R,3R,4R,5R)-2-((Bis(4-methoxyphenyl)(phenyl)methoxy)methyl)-4-(tert-butyldimethylsilyloxy)-5-(6-(3-formylphenyl)-9H-purin-9-yl)tetrahydrofuran-3-yl 2-cyanoethyl diisopropylphosphoramidite (Compound am-18) is obtained in the same manner as in Reference Example 6.1 using ((3aR,4R,6R,6aR)-6-(6-(3-formylphenyl)-9H-purin-9-yl)-2,2-dimethyltetrahydrofuro[3,4-d][1,3]dioxol-4-yl)methanol obtained in Step 1 of Reference Example 18.0.

EXAMPLE 24

An siRNA having Compound I-22 at the 5' end of the antisense strand is synthesized in the same manner as in Example 1 using Compound am-18 obtained in Reference Example 18.1.

REFERENCE EXAMPLE 19.0

Compound I-23

((2R,3S,4R,5R)-3,4-Dihydroxy-5-(6-nitro-2,4-dioxo-,4-dihydroquinazolin-1 (2H)-yl)tetrahydrofuran-2-yl)methyl phosphate (Compound I-23) triethylammonium salt was obtained in the same manner as in Reference Example 1.0 using commercially available 6-nitro-1H-quinazoline-2,4-dione.

$^1$H-NMR (D$_2$O, 300 MHz) δ: 8.82 (d, J=2.9 Hz, 1H), 8.49 (dd, J=9.3, 2.4 Hz, 1H), 7.89 (d, J=9.5 Hz, 1H), 6.27 (d, J=5.9 Hz, 1H), 4.73 (t, J=6.2 Hz, 1H), 4.42 (t, J=5.9 Hz, 1H), 4.09-4.04 (m, 3H), 3.08 (q, J=7.3 Hz, 6H), 1.16 (t, J=7.3 Hz, 9H).

ESI-MS (m/z): 420 (M+1)

REFERENCE EXAMPLE 19.1

Compound am-19

(2R,3R,4R,5R)-2-((Bis(4-methoxyphenyl)(phenyl)methoxy)methyl)-4-(tert-butyldimethylsilyloxy)-5-(6-nitro-2,4-dioxo-3,4-dihydroquinazolin-1(2H)-yl)tetrahydrofuran-3-yl 2-cyanoethyl diisopropylphosphoramidite (Compound am-19) is obtained in the same manner as in Reference Example 1.1 using commercially available 6-nitro-1H-quinazoline-2,4-dione.

EXAMPLE 25

An siRNA having Compound I-23 at the 5' end of the antisense strand is synthesized in the same manner as in Example 1 using Compound am-19 obtained in Reference Example 19.1.

REFERENCE EXAMPLE 20.0

Compound I-24

Steps 1 to 4

Di-tert-butyl ((3aR,4R,6R,6aR)-6-(5,6-dimethyl-2,4-dioxo-3,4-dihydropyrimidin-1 (2H)-yl)-2,2-dimethyltetrahydrofuro[3,4-d][1,3]dioxol-4-yl)methyl phosphate was obtained in the same manner as in Steps 1 to 4 of Reference Example 1 using commercially available 5,6-dimethylpyrimidine-2,4(1H,3H)-dione.

ESI-MS (m/z): 505 (M+1)

Step 5

Di-tert-butyl ((3aR,4R,6R,6aR)-6-(5,6-dimethyl-2,4-dioxo-3,4-dihydropyrimidin-1 (2H)-yl)-2,2-dimethyltetrahydrofuro[3,4-d][1,3]dioxol-4-yl)methyl phosphate (200 mg, 0.396 mmol) obtained in Step 4 was dissolved in 1,4-dioxane (4.00 mL), and selenium dioxide (440 mg, 3.96 mmol) was added thereto, and the mixture was stirred overnight under reflux. The reaction solution was filtered through Celite, and the residue obtained by evaporating the solvent under reduced pressure was purified by column chromatography (heptane/ethyl acetate) to obtain di-tert-butyl ((3aR,4R,6R,6aR)-6-(6-(hydroxymethyl)-5-methyl 2,4-dioxo-3,4-dihydropyrimidin-1(2H)-yl)-2,2-dimethyltetrahydrofuro[3,4-d][1,3]dioxol-4-yl)methyl phosphate (38.6 mg, yield: 19%) was obtained.

ESI-MS (m/z): 521 (M+1)

Step 6

Di-tert-butyl ((3aR,4R,6R,6aR)-6-(6-(hydroxymethyl)-5-methyl 2,4-dioxo-3,4-dihydropyrimidin-1(2H)-yl)-2,2-dimethyltetrahydrofuro[3,4-d][1,3]dioxol-4-yl)methyl phosphate (38.6 mg, 0.074 mmol) obtained in Step 5 was dissolved in acetonitrile (1.00 mL), and pyridine (0.06 mL, 0.742 mmol) and Dess-Martin periodinane (62.9 mg, 0.148 mmol) were added thereto, and the mixture was stirred overnight at 60° C. After the reaction solution was cooled to room temperature, a saturated aqueous sodium bicarbonate solution was added thereto, and the mixture was filtered through Presep (registered trademark, diatomaceous earth, Granular Type M, 4.5 g/25 mL), and the solvent was evaporated under reduced pressure. The residue obtained was purified by preparative thin-layer chromatography (hexane/ethyl acetate=20/80) to obtain di-tert-butyl ((3aR,4R,6R,6aR)-6-(6-(hydroxymethyl)-5-methyl-2,4-dioxo-3,4-dihydropyrimidin-1(2H)-yl)-2,2-dimethyltetrahydrofuro[3,4-d][1,3]dioxol-4-yl)methyl phosphate (32.8 mg, yield: 85%).

ESI-MS (m/z): 519 (M+1)

Step 7

Di-tert-butyl ((3aR,4R,6R,6aR)-6-(6-(hydroxymethyl)-5-methyl-2,4-dioxo-3,4-dihydropyrimidin-1 (2H)-yl)-2,2-dimethyltetrahydrofuro[3,4-d][1,3]dioxol-4-yl)methyl phosphate (46.0 mg, 0.089 mmol) obtained in Step 6 was dissolved in THP (1.00 mL), and hydroxylamine hydrochloride (30.8 mg, 0.444 mmol) was added thereto, and the mixture was stirred at 60° C. for 2 hours. After the reaction solution was cooled to room temperature, a saturated aqueous sodium bicarbonate solution was added thereto, and the mixture was filtered through Presep (registered trademark, diatomaceous earth, Granular Type M, 4.5 g/25 mL), and the solvent was evaporated under reduced pressure. The residue was purified by preparative thin-layer chromatography (chloroform/methanol a 90/10) to obtain di-tert-butyl ((3aR, 4R,6R,6aR)-6-(6-((E)-(hydroxyimino)methyl)-5-methyl 2,4-dioxo-3,4-dihydropyrimidin-1(2H)-yl)-2,2-dimethyltetrahydrofuro[3,4-d][1,3]dioxol-4-yl)methyl phosphate (33.7 mg, yield: 71%) was obtained.

ESI-MS (m/z): 534 (M+1)

Step 8

Triphenylphosphine oxide (1.76 mg, 0.006 mmol) was dissolved in ethyl acetate (1.00 mL), and oxalyl chloride (0.017 mL, 0.19 mmol) was added thereto, and the mixture was stirred at room temperature for 5 minutes to prepare a reaction mixture. Di-tert-butyl ((3aR,4R,6R,6aR)-6-(6-((E)-(hydroxyimino)methyl)-5-methyl-2,4-dioxo-3,4-dihydropyrimidin-1(2H)-yl) 2,2-dimethyltetrahydrofuro[3,4-d][1,3]dioxol-4-yl)methyl phosphate (33.7 mg, 0.063 mmol) obtained in Step 7 was dissolved in ethyl acetate (1.00 mL), and the reaction solution was gradually added thereto, and the mixture was stirred overnight at room temperature. The residue obtained by evaporating the solvent was dissolved in trifluoroacetic acid/water (1:1) (2 mL), and the mixture was stirred at room temperature for 2 hours. After the solvent was evaporated under reduced pressure, acetic acid-triethylamine buffer (pH 6.5) (2 mL) was added thereto, and the solvent was evaporated again under reduced pressure. The resulting residue was dissolved in ethanol, and ethyl acetate was added thereto, and the precipitate was collected by filtration to obtain ((2R,3S,4R,5R)-5-(6-cyano-5-methyl-2,4-dioxo-3,4-dihydropyrimidin-1(2H)-yl)-3,4-dihydroxytetrahydrofuran-2-yl)methyl phosphate (Compound I-24) triethylammonium salt (1.6 mg (two batches), yield: 74%) was obtained.

$^1$H-NMR (D$_2$O, 300 MHz) δ: 5.96 (d, J=4.0 Hz, 1H), 4.41 (t, J=6.4 Hz, 1H), 4.19-4.06 (m, 3H), 3.21 (q, J=7.2 Hz, 6H), 2.19 (8, 3H), 1.28 (t, J=7.5 Hz, 9H).

ESI-MS (m/z): 404 (M+1)

REFERENCE EXAMPLE 20.1

Compound am-20

Step 1

(2R,3R,4R,5R)-2-(Benzoyloxymethyl)-5-(6-(hydroxymethyl)-5-methyl-2,4-dioxo-3,4-dihydropyrimidin-1(2H)-yl) tetrahydrofuran-3,4-diyl benzoate was obtained in the same manner as in Step 5 of Reference Example 20.0 using (2R,3R,4R,5R)-2-(benzoyloxyethyl)-5-(5,6-dimethyl-2,4-dioxo-3,4-dihydropyrimidin 1(2H)-yl)tetrahydrofuran-3,4-diyl benzoate obtained in Step 1 of Reference Example 20.0.

ESI-MS (m/z): 601 (M+1)

Step 2

(2R,3R,4R,5R)-2-(benzoyloxymethyl)-5-(6-formyl-5-methyl-2,4-dioxo-3,4-dihydropyrimidin-1(2H)-yl)tetrahydrofuran-3,4-diyl benzoate was obtained in the same manner as in Step 6 of Reference Example 20.0 using (2R,3R,4R,5R)-2-(benzoyloxymethyl)-5-(6-hydroxymethyl)-5-methyl-2,4-dioxo-3,4-dihydropyrimidin-1(2H)-yl)tetrahydrofuran-3,4-diyl benzoate obtained in Step 1.

ESI-MS (m/z): 599 (M+1)

Step 3

(2R,3R,4R,5R)-2-(Benzoyloxymethyl)-5-(6-((E)-(hydroxyimino)methyl)-5-methyl-2,4-dioxo-3,4-dihydropyrimidin-1(2H)-yl)tetrahydro furan-3,4-diyl benzoate was obtained in the same manner as in Step 7 of Reference Example 20.0 using (2R,3R,4R,5R)-2-(benzoyloxymethyl)-5-(6-formyl-5-methyl-2,4-dioxo-3,4-dihydropyrimidin 1 (2H)-yl)tetrahydrofuran-3,4-diyl benzoate obtained in Step 2.

ESI-MS (m/z): 614 (M+1)

Step 4

Triphenylphosphine oxide (11.0 mg, 0.039 mmol) was dissolved in ethyl acetate (5.00 mL), and oxalyl chloride (0.104 mL, 1.183 mmol) was added thereto, and the mixture was stirred at room temperature for 5 minutes to obtain a reaction mixture solution. (2R,3R,4R,5R)-2-(Benzoyloxymethyl)-5-(6-((E)-(hydroxyimino)methyl-5-methyl-2,4-dioxo-3,4-dihydropyrimidin-1(2H)-yl)tetrahydrofuran-3,4-diyl benzoate (242 mg, 0.394 mmol) obtained in Step 3 was dissolved in ethyl acetate (5.00 mL), and the reaction solution was gradually added thereto, and the mixture was stirred at room temperature for 2 hours. The residue obtained by evaporating the solvent under reduced pressure was purified by column chromatography (heptane/ethyl acetate) to obtain (2R,3R,4R,5R)-2-(benzoyloxymethyl)-5-(6-cyano-5-methyl-2,4-dioxo-3,4-dihydropyrimidin-1 (2H)-yl) tetrahydrofuran-3,4-diyl benzoate (207 mg, yield: 88%) was obtained.

ESI-MS (m/z): 596 (M+1)

Step 5

3-((2R,3R,4S,5R)-3,4-Dihydroxy-5-(hydroxymethyl)tetrahydrofuran-2-yl)-5-methyl-2,6-dioxo-1,2,3,6-tetrahydropyrimidine-4-carbonitrile was obtained in the same manner as in Step 2 of Reference Example 1.0 using (2R,3R,4R, 5R)-2-(benzoyloxymethyl)-5-(6-cyano-5-methyl-2,4-dioxo-3,4-dihydropyrimidin-1(2H)-yl)tetrahydrofuran-3,4-diyl benzoate obtained in Step 4.

ESI-MS (m/z): 284 (M+1)

Steps 6 to 10

(2R,31R,4S,5R)-2-((Bis(4-methoxyphenyl)(phenyl) methoxy)methyl)-4-(tert-butyldimethylsilyloxy)-5-(6-cyano-5-methy-2,4-dioxo-3,4-dihydropyrimidin-1 (2H)-yl) tetrahydrofuran-3-yl 2-cyanoethyl diisopropylphosphoramidite (Compound am-20) is obtained in the same manner as in Steps 1 to 5 of Reference Example 1.1 using 3-1 (2R,3R,4S,5R)-3,4-dihydroxy-5-(hydroxymethyl)tetrahydrofuran-2-yl)-5-methyl-2,6-dioxo-1,2,3,6-tetrahydropyrimidin-4-carbonitrile obtained in Step 5.

EXAMPLE 26

An siRNA having Compound I-24 at the 5' end of the antisense strand is synthesized in the same manner as in Example 1 using Compound am-20 obtained in Reference Example 20.1.

REFERENCE EXAMPLE 21.0

Compound I-25

Step 1

((3aR,4R,6R,6aR)-2,2-Dimethyl-6-(6-(naphthalen-1-yl)-9H-purin 9-yl)tetrahydrofuro[3,4-d][1,3]dioxol-4-yl)methanol (150 mg, 117%) was obtained in the same manner as in Step 2 of Reference Example 6.0 using ((3aR,4R,6R,6aR)-6-(6-chloro-9H-purin 9-yl)-2,2-dimethyltetrahydrofuro[3,4-d][1,3]dioxol-4-yl)methanol (100 mg, 0.306 mmol)

obtained in Step 1 of Reference Example 6.0 and naphthalen-1-yl boronic acid (105 mg, 0.612 mmol).

ESI-MS (m/z): 419 (M+1)

Step 2

Di-tert-butyl ((3aR,4R,6R,6aR)-2,2-dimethyl-6-(6-(naphthalen-1-yl)-9H-purin-9-yl)tetrahydrofuro[3,4-d][1,3]dioxol-4-yl)methyl phosphate (70.0 mg, 37.5%) was obtained in the same manner as in Step 3 of Reference Example 6.0 using ((3aR,4R,6R,6aR)-2,2-dimethyl-6-(6-naphthylen-1-yl)-9H-purin-9-yl)tetrahydrofuro[3,4-d][1,3]dioxol-4-yl)methanol (128 mg, 0.306 mmol) obtained in Step 1.

ESI-MS (m/z): 611 (M+1)

Step 3

((2R,3S,4R,5R)-3,4-Dihydroxy-5-(6-(naphthalen-1-yl)-9H-purin-9-yl)tetrahydrofuran-2-yl)methyl phosphate (Compound 7-25) triethylammonium salt (10.8 mg, 15.3%) was obtained in the same manner as in Step 3 of Reference Example 16.0 using di-tert-butyl ((3aR,4R,6R,6aR)-2,2-dimethyl-6-(6-(naphthalen-1-yl)-9H-purin-9-yl)tetrahydrofuro[3,4-d][1,3]dioxol-4-yl)methyl phosphate (77.0 mg, 0.126 mmol) obtained in Step 2.

$^1$H-NMR (D$_2$O, 300 MHz) δ: 8.87 (1H, s), 8.60 (1H, s), 8.07-7.84 (2H, m), 7.73-7.60 (2H, m), 7.58-7.40 (2H, s), 7.38-7.28 (1H, m), 6.21 (1H, d, J=5.5 Hz), 4.75-4.66 (1H, m), 4.45-4.38 (1H, m), 4.35-4.28 (1H, m), 4.10-3.98 (2H, m), 3.05 (6H, q, J=7.3 Hz), 1.13 (9H, t, J=7.3 Hz).

ESI-MS (m/z): 459 (M+1)

REFERENCE EXAMPLE 21.1

Compound am-21

Step 1

9-((4aR,6R,7R,7aS)-2,2-Di-tert-butyl-7-(tert-butyldimethylsilyloxy)tetrahydro-4H-furo[3,2-d][1,3,2]dioxasilin-6-yl)-6-(naphthalen-1-yl)-9H-purine was obtained in the same manner as in Step 1 of Reference Example 21.0 using 6-chloro-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine obtained in Step 2 of Reference Example 17.1.

ESI-MS (m/z): 633 (M+1)

Steps 2 to 4

(2R,3R,4R,5R)-2-((Bis(4-methoxyphenyl)(phenyl)methoxy)methyl)-4-(tert-butyldimethylsilyloxy)-5-(6-(naphthalen-1-yl)-9H-purin-9-yl)tetrahydrofuran-3-yl 2-cyanoethyl diisopropylphosphoramidite (Compound am-21) was obtained in the same manner as in Steps 3 to 5 of Reference Example 1.1 using 9-((4aR,6R,7R,7aS) 2,2-di-tert-butyl-7-(tert-butyldimethylsilyloxy)tetrahydro-4H-furo[3,2-d][1,3,2]dioxasilin-6-yl)-6-(naphthalen-1-yl)-9H-purine obtained in Step 1.

$^1$H-NMR (CDCl$_3$, 500 MHz) δ: 9.04 (m, 1H), 8.34 (m, 1H), 8.20 (m, 1H), 8.04-7.91 (m, 2H), 7.93 (m, 1H), 7.64 (m, 1H), 7.54-7.45 (m, 4H), 7.39-6.79 (m, 11H), 6.21 (6.15) (m, 1H), 5.16 (m, 1H), 4.51-4.39 (m, 2H), 4.04-3.32 (m, 12H), 2.68 (2.32) (m, 2H), 1.25-1.06 (m, 12H), 0.76 (0.77) (s, 9H), −0.01 (0.01) (s, 3H), −0.16 (−0.15) (s, 3H).

EXAMPLE 27

An siRNA (6-napht-1-yl-dPu) having Compound I-25 as X at the 5' end of the antisense strand of 454-Xa shown in Table 24 below was synthesized in the same manner as in Example 1 using Compound am-21 obtained in Reference Example 21.1.

MALDI-TOF/MS (antisense strand): theoretical value: 6801.03 (M-H), actual value: 6800.94

REFERENCE EXAMPLE 22.0

Compound I-26

Step 1

((3aR,4R,6R,6aR)-6-(6-(Biphenyl-3-yl)-9H-purin-9-yl)-2,2-dimethyltetrahydrofuro[3,4-d][1,3]dioxol-4-yl)methanol (130 mg, 95%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and (1,1'-biphenyl)-3-yl boronic acid (121 mg, 0.612 mmol).

ESI-MS (m/z): 445 (M+1)

Step 2

Di-tert-butyl ((3aR,4R,6R,6aR)-6-(6-(biphenyl-3-yl)-9H-purin-9-yl)-2,2-dimethyl tetrahydrofuro[3,4-d][1,3]dioxol-4-yl)methyl phosphate (107 mg, 59.8%) was obtained in the same manner an in Step 3 of Reference Example 6.0 using ((3aR,4R,6R,6aR)-6-(6-(biphenyl-3-yl)-9H-purin-9-yl)-2,2-dimethyl tetrahydrofuro[3,4-d][1,3]dioxol-4-yl)methanol. (125 mg, 0.281 mmol) obtained in Step 1.

ESI-MS (m/z): 637 (M+1)

Step 3

((2R,3S,4R,5R)-5-(6-(Biphenyl-3-yl)-9H-purin-9-yl)-3,4-dihydroxytetrahydrofuran-2-yl)methyl phosphate (Compound I-26) (47.0 mg, 61.8%) was obtained in the same manner as in Step 5 of Reference Example 1.0 using di-tert-buty ((3aR,4R,6R,6aR)-6-(6-(biphenyl-3-yl)-9H-purin-9-yl)-2,2-dimethyl tetrahydrofuro[3,4-d][1,3]dioxol-4-yl)methyl phosphate (100 mg, 0.157 mmol) obtained in Step 2.

$^1$H-NMR (DMSO-d$_6$, 300 MHz) δ: 9.14 (1H, s), 9.06 (1H, s), 8.89 (1H, s), 8.82 (1H, d, J=7.7 Hz), 7.09 (1H, d, J=7.7 Hz), 7.79-7.68 (3H, m), 7.58-7.50 (2H, m), 7.47-7.40 (1H, m), 6.15 (1H, d, J=5.5 Hz), 4.72-4.65 (1H, m), 4.27-4.22 (1H, m), 4.20-3.98 (3H, m).

ESI-MS (m/z): 485 (M+1)

REFERENCE EXAMPLE 22.1

Compound am-22

Step 1

6-(Biphenyl-3-yl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine is obtained in the same manner as in Step 1 of Reference Example 22.0 using 6-chloro-9-((4aR,6R,7R,7aS)-2,2-di-tert-butyl-7-(tert-butyldimethylsilyl(oxy)tetrahydro-4H-furo[3,2-d][1,3,2]dioxasilin-6-yl)-9H-purine obtained in Step 2 of Reference Example 17.1.

Steps 2 to 4

(2R,3R,4R,5R)-5-(6-(biphenyl-3-yl)-9H-purin-9-yl)-2-((bis(4-methoxyphenyl)(phenyl)methoxy)methyl)-4-(tert-butyldimethylsilyloxy)tetrahydrofuran-3-yl 2-cyanoethyl diisopropylphosphoramidite (Compound am-22) is obtained in the same manner as in Steps 3 to 5 of Reference Example 1.1 using 6-(biphenyl-3-yl)-9-((4aR,6R,7R,7aR)-2,2-di-tertbutyl-7-(tert-butyldimethylsilyloxy)tetrahydro-4H-furo[3,2-d][1,3,2]dioxasilin-6-yl)-9H-purine obtained in Step 1.

EXAMPLE 28

An siRNA having Compound I-26 at the 5' end of the antisense strand is synthesized in the same manner as in Example 1 using Compound am-22 obtained in Reference Example 22.1.

REFERENCE EXAMPLE 23.0

Compound I-27

Step 1
((3aR,4R,6R,6aR)-6-(6-(3-Aminophenyl)-9H-purin-9-yl)-2,2-dimethyltetrahydrofuro[3,4-d][1,3]dioxol-4-yl)methanol (77.2 mg, 65.8%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and (3-aminophenyl)boronic acid (84 mg, 0.612 mmol).
ESI-MS (m/z): 384 (M+3)
Step 2
Di-tert-butyl ((3aR,4R,6R,6aR)-6-(6-(3-aminophenyl)-9H-purin-9-yl)-2,2-dimethyl tetrahydrofuro[3,4-d][1,3]dioxol-4-yl)methyl phosphate (38.4 mg, 33.2%) was obtained in the same manner as in Step 3 of Reference Example 6.0 using ((3aR,4R,6R,6aR)-6-(6-(3-aminophenyl)-9H-purin-9-yl)-2,2-dimethyl tetrahydrofuro[3,4-d][1,3]dioxol-4-yl)methanol (77.0 mg, 0.201 mmol) obtained in Step 1.
ESI-MS (m/z): 576 (M+1)
Step 3
((2R,3S,4R,5R)-5-(6-(3-Aminophenyl)-9H-purin-9-yl)-3,4-dihydroxytetrahydrofuran-2-yl)methyl phosphate (Compound I-27) (13.0 mg, 43.3%) was obtained in the same manner as in Step 5 of Reference Example 1.0 using di-tert-butyl ((3aR,4R,6R,6aR)-6-(6-(3-aminophenyl)-9H-purin-9-yl)-2,2-dimethyl tetrahydrofuro[3,4-d][1,3]dioxol-4-yl)methyl phosphate (38.0 mg, 0.0660 mmol) obtained in Step 2.
$^1$H-NMR (D$_2$O, 300 MHz) δ: 8.82 (1H, s), 8.73 (1H, s), 8.22-8.15 (2H, m), 7.66-7.58 (1H, m), 7.55-7.48 (1H, m), 6.16 (1H, d, J=5.5 Hz), 4.72-4.65 (1H, m), 4.45-4.38 (1H, m), 4.35-4.26 (1H, m), 4.14-3.98 (2H, m).
ESI-MS (m/z): 424 (M+1)

REFERENCE EXAMPLE 23.1

Compound am-23

Step 1
6-(3-Aminophenyl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine is obtained in the same manner as in Step 1 of Reference Example 23.0 using 6-chloro-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine obtained in Step 2 of Reference Example 17.1.
Steps 2 to 4
(2R,3R,4R,5R)-5-(6-(3-Aminophenyl)-9H-purin-9-yl)-2-((bis(4-methoxyphenyl)(phenyl)methoxy)methyl)-4-(tert-butyldimethylsilyloxy)tetrahydrofuran-3-yl 2-cyanoethyl diisopropylphosphoramidite (Compound am-23) is obtained in the same manner as in Steps 3 to 5 of Reference Example 1.1 using 9-((4aR,6R,7R,7aS)-2,2-di-tert-butyl-7-(tert-butyldimethylsilyloxy)tetrahydro-4H-furo[3,2-d][1,3,2]dioxasilin-6-yl)-6-(3-aminophen yl)-9H-purine obtained in Step 1.

EXAMPLE 29

An siRNA having Compound I-27 at the 5' end of the antisense strand is synthesized in the same manner as in Example 1 using Compound am-23 obtained in Reference Example 23.1.

REFERENCE EXAMPLE 24.0

Compound I-28

Step 1 ((3aR,4R,6R,6aR)-2,2-Dimethyl-6-(6-(3-morpholinophenyl)-9H-purin-9-yl)tetrahydrofuro[3,4-d][1,3]dioxol-4-yl)methanol (127 mg, 92%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and (3-morpholinophenyl)boronic acid (127 mg, 0.612 mmol).
ESI-MS (m/z): 454 (M+1)
Step 2
Di-tert-butyl ((3aR,4R,6R,6aR)-2,2-dimethyl-6-(6-(3-morpholinophenyl)-9H-purin-9-yl)tetrahydrofuro[3,4-d][1,3]dioxol-4-yl)m methyl phosphate (65.0 mg, 38.0%) was obtained in the name manner as in Step 3 of Reference Example 6.0 using ((3aR,4R,6R,6aR)-2,2-dimethyl-6-(6-(3-morpholinophenyl)-9H-purin-9-yl)tetrahydrofuro[3,4-d][1,3]dioxol-4-yl)methanol (120 mg, 0.265 mmol) obtained in Step 1.
ESI-MS (m/z): 646 (M+1)
Step 3 ((2R,3S,4R,5R)-3,4-Dihydroxy-5-(6-(3-morpholinophenyl)-9H-purin-9-yl)tetrahydrofuran-2-yl)methyl phosphate (Compound I-28) triethylammonium salt (9.00 mg, 15.51) was obtained in the same manner as in Step 3 of Reference Example 16.0 using di-tert-butyl ((3aR,4R,6aR)-2,2-dimethyl-6-(6-(3-morpholinophenyl)-9H-purin-9-yl)tetrahydrofuro[3,4-d][1,3]dioxol-4-yl)methyl phosphate (63.0 mg, 0.0980 mmol) obtained in Step 2.
$^1$H-NMR (D$_2$O, 300 MHz) δ: 8.83 (1H, s), 8.72 (1H, s), 7.85-7.75 (2H, m), 7.52-7.44 (1H, m), 7.28-7.20 (1H, m), 6.21-6.19 (1H, m), 4.76-4.68 (1H, m), 4.45-4.40 (1H, m), 4.34-4.28 (1H, m), 4.06 (2H, s), 3.88-3.80 (4H, m), 3.23-3.15 (4H, m), 3.08 (6H, q, J=7.3 Hz), 1.16 (9H, t, J=7.3 Hz).
ESI-MS (m/z): 494 (M+1)

REFERENCE EXAMPLE 24.1

Compound am-24

Step 1
9-((4aR,6R,7R,7aS)-2,2-Di-tert-butyl-7-(tert-butyldimethylsilyloxy)tetrahydro-4H-furo[3,2-d][1,3,2]dioxasilin-6-yl)-6-(3-morpholinophenyl)-9H-purine is obtained in the same manner as in Step 1 of Reference Example 24.0 using 6-chloro-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine obtained in Step 2 of Reference Example 17.1.
Steps 2 to 4
(2R,3R,4R,5R)-2-((Bis(4-methoxyphenyl)(phenyl)methoxy)methyl)-4-(tert-butyldimethylsilyloxy)-b-(6-(3- morpholinophenyl)-9H-purin-9-yl)tetrahydrofuran-3-yl 2-cyanoethyl diisopropylphosphoramidite (Compound am-24) is obtained in the same manner as in Steps 3 to 5 of Reference Example 1.1 using 9-((4aR,6R,7R,7aS)-2,2-di-tert-butyl-7-(tert-butyldimethylsilyloxy)tetrahydro-4H-furo[3,2-d][1,3,2]dioxasilin-6-yl)-6-(3-morpholinophenyl)-9H-purine obtained in Step 1.

EXAMPLE 30

An siRNA having Compound I-28 at the 5' end of the antisense strand is synthesized in the same manner as in Example 1 using Compound am-24 obtained in Reference Example 24.1.

REFERENCE EXAMPLE 25.0

Compound I-29

Step 1

((3aR,4R,6R,6aR)-6-(6-(3-(Benzyloxy)phenyl)-9H-purin-9-yl)-2,2-dimethyltetrahydrofuro[3,4-d][1,3]dioxol-4-yl)methanol (180 mg, 130%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and (3-(benzyloxy)phenyl)boronic acid (140 mg, 0.612 mmol).

ESI-MS (m/z): 475 (14.1)

Step 2

Di-tert-butyl ((3aR,4R,6R,6aR)-6-(6-(3-(benzyloxy)phenyl)-9H-purin-9-yl)-2,2-dimethyltetrahydrofuro[3,4-d][1,3]dioxol-4-yl)methyl phosphate (95.0 mg, 48.3%) was obtained in the same manner as in Step 3 of Reference Example 6.0 using ((3aR,4R,6R,6aR)-6 (6-(3-(benzyloxy)phenyl)-9H-purin-9-yl)-2,2-dimethyltetrahydrofuro[3,4-d][1,3]dioxol-4-yl)methanol (140 mg, 0.295 mmol) obtained in Step 1.

ESI-MS (m/z): 667 (M+1)

Step 3

((2R,3S,4R,5R)-5-(6-(3-(Benzyloxy)phenyl)-9H-purin-9-yl)-3,4-dihydroxytetrahydrofuran-2-yl)methyl phosphate (Compound I-29) triethylammonium salt (32.0 mg, 36.5%) was obtained in the same manner as in Step 3 of Reference Example 16.0 using di-tert-butyl ((3aR,4R,6R,6aR)-6 (6-(3-(benzyloxy)phenyl)-9H-purin 9-yl)-2,2-dimethyltetrahydrofuro[3,4-d][1,3]dioxol-4-yl)methyl phosphate (95.0 mg, 0.142 mmol) obtained in Step 2.

$^1$H-NMR (D$_2$O, 400 MHz) δ: 8.63 (1H, s), 8.59 (1H, s), 7.67-7.55 (2H, m), 7.30-7.1.6 (6H, m), 6.94-6.88 (1H, m), 6.06 (1H, d, J=5.9 Hz), 4.88 (2H, s), 4.71-4.62 (1H, m), 4.39-4.34 (1H, m), 4.28-4.22 (1H, m), 4.06-3.95 (2H, m), 3.14-2.95 (6H, q, J=7.3 Hz), 1.12 (9H, t, J=7.3 Hz).

ESI-MS (m/z): 515 (M+1)

REFERENCE EXAMPLE 25.1

Compound am-25

Step 1

6-(3-(Benzyloxy)phenyl)-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine is obtained in the same manner as in Step 1 of Reference Example 25.0 using 6-chloro-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine obtained in Step 2 of Reference Example 17.1.

Steps 2 to 4

(2R,3R,4R,5R)-5-(6-(3-(Benzyloxy)phenyl-9H-purin-9-yl)-2-((bis(4-methoxyphenyl)(phenyl)methoxy)methyl)-4-(tert-butyldimethylsilyloxy)tetrahydrofuran-3-yl 2-cyanoethyl diisopropylphosphoramidite (Compound am-25) is obtained in the same manner as in Steps 3 to 5 of Reference Example 1.1 using 6-(3-(benzyloxy)phenyl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine obtained in Step 1.

EXAMPLE 31

An siRNA having Compound I-29 at the 5' end of the antisense strand is synthesized in the same manner as in Example 1 using Compound am-25 obtained in Reference Example 25.1.

REFERENCE EXAMPLE 26.0

Compound I-30

Step 1

((3aR,4R,6R,6aR)-6-(6-(3-(Methoxycarbonyl)phenyl)-9H-purin-9-yl)-2,2-dimethyltetrahydrofuro[3,4-d][1,3]dioxol-4-yl)methanol (160 mg, 123%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxol-4-yl)methanol (100 mg, 0.306 mmol) obtained in Step 1 of Reference Example 6.0 and (3-(methoxycarbonyl)phenyl)boronic acid (110 mg, 0.612 mmol).

ESI-MS (m/z): 427 (M+1)

Step 2

Di-tert-butyl ((3aR,4R,6R,6aR)-6-(6-(3-(methoxycarbonyl)phenyl)-9H-purin-9-yl)-2,2-dimethyltetrahydrofuro[3,4-d][1,3]dioxol-4-yl)methyl phosphate (100 mg, 53.0%) was obtained in the same manner as in Step 3 of Reference Example 6.0 using ((3aR,4R,6R,6aR)-6-(6-(3-(methoxycarbonyl)phenyl)-9H-purin-9-yl)-2,2-dimethyltetrahydrofuro[3,4-d][1,3]dioxol-4-yl)methanol (130 mg, 0.305 mmol) obtained in Step 1.

ESI-MS (m/z): 619 (M+1)

Step 3

((2R,3S,4R,5R)-5-(6-(3-(Methoxycarbonyl)phenyl)-9H-purin-9-yl)-3,4-dihydroxytetrahydrofuran-2-yl)methyl phosphate (45.0 mg, 87.0%) was obtained in the same manner as in Step 5 of Reference Example 1.0 using di-tert-butyl ((3aR,4R,6R,6aR)-6-(6-(3-(methoxycarbonyl)phenyl)-9H-purin-9-yl)-2,2-dimethyltetrahydrofuro[3,4-d][1,3]dioxol-4-yl)methyl phosphate (68.7 mg, 0.111 mmol) obtained in Step 2.

ESI-MS (m/z): 467 (M+1)

Step 4

((2R,3S,4R,5R)-5-(6-(3-(Methoxycarbonyl)phenyl)-9H-purin-9-yl)-3,4-dihydroxytetrahydrofuran-2-yl)methyl phosphate (20.0 mg, 0.0430 mmol) obtained in Step 3 was dissolved in a 1 N aqueous sodium hydroxide solution (2 mL), and the mixture was stirred at room temperature for 2 hours. Acetic acid-triethylamine buffer (pH 6.5) was added thereto, and the residue obtained by evaporating the solvent under reduced pressure was purified by preparative HPLC (eluent: a 0.01 mmol/L aqueous ammonium acetate solution/methanol) to obtain ((2R,3S,4R,5R)-5-(6-(3-(carboxy)phenyl)-9H-purin-9-yl)-3,4-dihydroxytetrahydrofuran-2-yl) methyl phosphate (Compound I-30) triethylammonium salt (10.0 mg, 42.1%) was obtained.

$^{1}$H-NMR (D$_{2}$O, 300 MHz) δ: 8.88-8.53 (3H, m), 8.34-8.22 (1H, m), 8.03-7.92 (1H, m), 7.60-7.48 (1H, m), 6.22-6.15 (1H, m), 4.76-4.65 (1H, m), 4.47-4.42 (1H, m), 4.35-4.30 (1H, m), 4.15-4.00 (2H, m), 3.09 (6H, q, J=7.2 Hz), 1.16 (9H, t, J=7.3 Hz).

ESI-MS (m/z): 453 (M+1)

REFERENCE EXAMPLE 26.1

Compound am-26

Step 1
9-((4aR,6R,7R,7aS)-2,2-Di-tert-butyl-7-(tert-butyldimethylsilyloxy)tetrahydro-4H-furo[3,2-d][1,3,2]dioxasilin-6-yl)-6-(3-methoxycarbonyl)-9H-purine is obtained in the same manner as in Step 1 of Reference Example 26.0 using 6-chloro-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine obtained in Step 2 of Reference Example 17.1.

Step 2
9-((4aR,6R,7R,7aS)-2,2-Di-tert-butyl-7-(tert-butyldimethylsilyloxy)tetrahydro-4H-furo[3,2-d][1,3,2]dioxasilin-6-yl)-6-(3-carboxyl)-9H-purine is obtained in the same manner as in Step 4 of Reference Example 26.0 using 9-(4aR,6R,7R,7aS)-2,2-di-tert-butyl-7-(tert-butyldimethoxylsilyloxy)tetrahydro-4H-furo[3,2-d][1,3,2] dioxasilin-6-yl) 6-(3-methoxycarbonyl)-9H-purine obtained in Step 1.

Steps 3 to 5
(2R,3R,4R,5R)-2-((Bis(4-methoxyphenyl)(phenyl) methoxy)methyl)-4-(tert-butyldimethylsilyloxy)-5-(6-(3-carboxylphenyl)-9H-purin-9-yl)tetrahydrofuran-3-yl 2-cyanoethyl diisopropylphosphoramidite (Compound am-26) is obtained in the same manner as in Steps 3 to 5 of Reference Example 1.1 using 9-((4aR,6R,7R,7aS)-2,2-di-tert-butyl-7-(tert-butyldimethylsilytoxy)tetrahydro-4H-furo[3,2-d][1,3,2]dioxasilin-6-yl)-6-(3-carboxyl)-9H-purine obtained in Step 2.

EXAMPLE 32

An siRNA having Compound I-30 at the 5' end of the antisense strand is synthesized in the same manner as in Example 1 using Compound am-26 obtained in Reference Example 26.1.

REFERENCE EXAMPLE 27.0

Compound I-31

Step 1
1-((3aR,4R,6R,6aR)-6-(Hydroxymethyl)-2,2-dimethyltetrahydrofuro[3,4-d][1,3]dioxol-4-yl)-5-styrylpyrimidine-2,4(1H,3H)-dione (43.8 mg, 41%) was obtained in the same manner as in Step 2 of Reference Example 6.0 using 5-bromo-1-((2R,3R,4S,5R)-3,4-dihydroxy-5-(hydroxymethyl)tetrahydrofuran-2-yl)pyrimidine-2,4(1H,3H)-dione (100 mg, 0.275 mmol) obtained in Step 1 of Reference Example 10.0.

ES-MS (m/z): 385 (M−1)

Step 2
1-((3aR,4R,6R,6aR)-6-(Hydroxymethyl)-2,2-dimethyltetrahydrofuro[3,4-d][1,3]dioxol-4-yl)-5-styrylpyrimidine-2,4(1H,3H)-dione (16.3 mg, 0.042 mmol) obtained in Step 1 was dissolved in dichloromethane (2 mL), and 1H-tetrazole (7.39 mg, 0.105 mmol) and di-tert-butyl diisopropylphosphoramide (0.028 mL, 0.084 mmol) were added thereto, and the mixture was stirred at room temperature for 2 hours. After the reaction solution was cooled to 0° C., (2R,8aS)-(+)-(camphorylsulfonyl)oxaziridine (19.4 mg, 0.084 mmol) was added thereto, and the mixture was further stirred at 0° C. for 30 minutes. After the reaction solution was cooled to room temperature, a saturated aqueous sodium bicarbonate solution was added thereto, and the mixture was filtered through Presep (registered trademark, diatomaceous earth, Granular Type M, 4.5 g/25 mL), and then, the solvent was evaporated under reduced pressure. The residue was purified by column chromatography (heptane/ethyl acetate) to obtain di-tert-butyl ((3aR,4R,6R,6aR)-6-(2,4-dioxo-5-styryl-3,4-dihydropyrimidin-1(2H)-yl)-2,2-dimethyltetrahydrofuro[3,4-d][1,3]dioxol-4-yl)methyl phosphate (10.0 mg, 41%).

ESI-MS (m/z): 577 (M−1)

Step 3
((2R,3S,4R, R)-5-(2,4-Dioxo-5-styryl-3,4-dihydropyrimidin-1(2H)-yl)-3,4-dihydroxytetrahydrofuran-2-yl) methyl phosphate (Compound I-31) triethylammonium salt (9.30 mg, 102%) was obtained in the same manner as in Step 5 of Reference Example 1.0 using di-tert-butyl ((3aR,4R,6R,6aR)-6-(2,4-dioxo-5-styryl-3,4-dihydropyrimidin-1(2H)-yl)-2,2-dimethyltetrahydrofuro[3,4-d][1,3]dioxol-4-yl)methyl phosphate (10.0 mg, 0.017 mmol) obtained in step 2.

$^{1}$H-NMR (D$_{2}$O, 300 MHz) δ: 7.96 (s, 1H), 7.49 (d, J=7.3 Hz, 24), 7.37-7.19 (m, 3H), 6.88 (d, J=16.5 Hz, 1H), 5.91 (d, J=5.1 Hz, 1H), 4.32 t, J=5.1 Hz, 1H), 4.26 (t, J=4.8 Hz, 1H), 4.21-4.20 (m, 1H), 4.11-3.99 (m, 2H), 3.09 (q, J=7.3 Hz, 6H), 1.16 (t, J=7.3 Hz, 9H).

ESI-MS (m/z): 425 (M−1)

REFERENCE EXAMPLE 27.1

Compound am-27

Step 1
1-((4aR,6R,7R,7aR)-2,2-Di-tert-butyl-7-((tert-butyldimethylsilyl)oxy)tetrahydro-4H-furo[3,2-d][1,3,2]dioxasilin-6-yl)-5-styryl pyrimidine-2,4(1H,3H)-dione is obtained in the same manner as in Step 1 of Reference Example 27.0 using 5-bromo-1-((4aR,6R,7R,7?R)-2,2-di-tert-butyl-7-((tert-butyldimethylsilyl)oxy)tetrahydro-4H-furo[3,2-d][1,3,2]dioxasilin-6-yl)pyrimidine-2,4(1H,3H)-dione obtained in Step 2 of Reference Example 13.1.

Step 2
(2R,3R,4R,5R)-2-((Bis(4-methoxyphenyl)(phenyl) methoxy)methyl)-4-((tert-butyldimethylsilyloxy)-5-(2,4-dioxo-5-styryl-3,4-dihydropyrimidin-1(2H)-yl)tetrahydrofuran-3-yl(2-cyanoethyl) diisopropylphosphoramidite is obtained in the same manner as in Steps 3 to 5 of Reference Example 1.1 using 1-((4aR,6R,7R,7aR)-2,2-di-tert-butyl-7-((tert-butyldimethylsilyl)oxy)tetrahydro-4H-furo[3,2-d][1,3,2]dioxasilin-6-yl)-5-styrylpyrimidine-2,4(1H,3H)-dione obtained in Step 1.

EXAMPLE 33

An siRNA having Compound I-31 at the 5' end of the antisense strand is synthesized in the same manner as in Example 1 using Compound am-27 obtained in Reference Example 27.1.

REFERENCE EXAMPLE 28.1
Compound am-28

Step 1

Commercially available (2R,3R,4S,5R)-2-(6-chloro-9H-purin-9-yl)-5-(hydroxymethyl)tetrahydrofuran-3,4-diol (5.00 g, 17.4 mmol) was dissolved in pyridine (42 mL), and 1,3-dichloro-1,1,3,3-tetraisopropyldisiloxane (6.70 ml, 20.9 mmol) was added thereto, and the mixture was stirred at room temperature for 2 hours. To the reaction solution, water was added, and the mixture was extracted with ethyl acetate. The organic layer was washed with saturated brine and dried over sodium sulfate. The residue obtained by evaporating the solvent under reduced pressure was purified by column chromatography (hexane/ethyl acetate) to obtain (6aR,8R,9R,9aS)-8-(6-chloro-9H-purin-9-yl)-2,2,4,4-tetraisopropyl tetrahydro-6H-furo[3,2-f][1,3,5,2,4]trioxadisilocin-9-ol (8.64 g, yield: 94%).

ESI-MS (m/z): 530 (M+1)

Step 2

(6aR,8R,9R,9aS)-2,2,4,4-Tetraisopropyl-8-(6-((E)-styryl)-9H-purin-9-yl)tetrahydro-6H-furo[3,2-f][1,3,5,2,4]trioxadisilocin-9-ol (4.77 g, yield: 65%) was obtained in the same manner as in Step 2 of Reference Example 6.0 using (6aR,8R,9R,9aS)-8-(6-chloro-9H-purin-9-yl)-2,2,4,4-tetraisopropyl tetrahydro-6H-furo[3,2-f][1,3,5,2,4]trioxadisilocin-9-ol (6.50 g, 12.3 mmol) obtained in Step 1.

ESI-MS (m/z): 598 (M+1)

Step 3

(6aR,8R,9R,9aS)-2,2,4,4-Tetraisopropyl-8-(6-((E)-styryl)-9H-purin-9-yl)tetrahydro-6H-furo[3,2-f][1,3,5,2,4]trioxadisilocin-9-ol (4.50 g, 7.54 mmol) obtained in Step 2 was dissolved in N,N-dimethylformamide (50 mL), and 60% sodium hydride (302 mg, 7.54 mmol) and methyl iodide (0.471 mL, 7.54 mmol) were added thereto at 0° C., and the mixture was stirred at room temperature for 2 hours. To the reaction solution, water was added, and the mixture was extracted with ethyl acetate. The organic layer was washed with saturated brine and dried over sodium sulfate. The residue obtained by evaporating the solvent under reduced pressure was purified by column chromatography (hexane/ethyl acetate) to obtain 6-((E)-styryl)-9-((6aR,8R,9R,9aR)-2,2,4,4-tetraisopropyl-9-methoxytetrahydro-6H-furo[3,2-f][1,3,5,2,4]trioxadisilocin-8-yl)-9H-purine (2.09 g, yield: 45%).

ESI-MS (m/z): 612 (M+1)

Step 4

6-((E)-styryl)-9-((6aR,8R,9R,9aR)-2,2,4,4-Tetraisopropyl-9-methoxytetrahydro-6H-furo[3,2-f][1,3,5,2,4]trioxadisilocin-8-yl)-9H-purine (569 mg, 0.931 mmol) obtained in Step 3 was dissolved in tetrahydrofuran (10 mL), and acetic-acid (0.117 mL, 2.049 mmol) and a solution of tetrabutylammonium fluoride in tetrahydrofuran (1 mol/L, 2.05 ml, 2.05 mmol) were added thereto, and the mixture was stirred at room temperature for 30 minutes. The reaction solution was concentrated under reduced pressure, and the residue was purified by column chromatography (chloroform/methanol) to obtain (2R,3S,4R,5R)-2-(hydroxymethyl)-4-methoxy-5-(6 ((E)styryl)-9H-purin-9-yl)tetrahydrofuran-3-ol (341 mf, yield: 99%).

$^1$H-NMR (CDCl$_3$, 500 MHz) δ: 8.90 (s, 1H), 8.43 (d, J=16.7 Hz, 1H), 8.13 (8, 1H), 7.68-7.75 (m, 3H), 7.37-7.47 (m, 3H), 6.17 (dd, J=2.2, 11.9 Hz, 1H), 5.95 (d, J=7.0 Hz, 1H), 4.77 (dd, J=4.7, 7.4 Hz 1H), 4.61 (d, J=4.4 Hz, 1H)), 4.39-4.41 (m, 1H), 3.99-4.02 (m, 1H), 3.78-3.83 (m, 1H), 3.37 (s, 3H), 2.67 (s, 1H).

ESI-MS (m/z): 369 (M+1)

Step 5

(2R,3R,4R,5R)-2-((Bis(4-methoxyphenyl)(phenyl)methoxy)methyl)-4-methoxy-5-(6-((E)styryl)-9H-purin-9-yl)tetrahydrofuran-3-yl (2-cyanoethyl) diisopropylphosphoramidite (Compound am-28) was obtained in the same manner as in Reference Example 1.1 using ((2R,3S,4R,5R)-2-(hydroxymethyl)-4-methoxy-5-(6-((E)styryl) 0.9H-purin-9-yl)tetrahydrofuran-3-ol obtained in Step 4. This Compound was used in the subsequent Step without purification.

EXAMPLE 34

An siRNA (referred to as 2'-OMe-6-styryl-dA) having Compound I-32 as X at the 5' end of the antisense strand of 454-Xa shown in Table 24 below was synthesized in the same manner as in Example 1 using Compound am-28 obtained in Reference Example 28.1.

ESI-MS (m/z): theoretical value: 6792.04 actual value: 6792.18

REFERENCE EXAMPLE 29.0
Compound I-33

((2R,3S,4R,5R)-3,4-Dihydroxy-5-(5-methyl-2,4-dioxo-3,4-dihydropyrimidin-1(2H)-yl)tetrahydrofuran-2-yl)methyl phosphate (Compound I-33) was obtained in the same manner as in Reference Example 1.0 using commercially available 5-methylpyrimidine-2,4(1H,3H)-dione.

$^1$H-NMR (D$_2$O, 300 MHz) δ: 7.67 (s, 1H), 5.86 (d, J=5.5 Hz, 1H), 4.23 (dt, J=12.8, 4.9 Hz, 2H), 4.13 (dt, J=6.0, 2.6 Hz, 1H), 4.02-3.89 (m, 2H), 1.80 (s, 3H).

ESI-MS (m/z): 337 (M−1)

REFERENCE EXAMPLE 29.1
Compound am-29

Step 1

(2R,3R,4R,5R)-2-((Bis(4-methoxyphenyl)(phenyl)methoxy)methyl)-4-((tert-butyldimethylsilyl)oxy)-5-(5-methyl-2,4-dioxo-3,4-dihyd ropyrimidin-1(2H)-yl)tetrahydrofuran-3-yl(2-cyanoethyl) diisopropylphosphoramidite is obtained in the same manner as in Reference Example 1.1 using commercially available 5-methylpyrimidine-2,4(1H, 3H)-dione.

EXAMPLE 35

An siRNA having Compound I-33 at the 5' end of the antisense strand is synthesized in the same manner as in Example 1 using Compound am-29 obtained in Reference Example 29.1.

REFERENCE EXAMPLE 30.0
Compound I-34

((2R,3S,4R,5R)-3,4-Dihydroxy-5-(6-methyl-2,4-dioxo-3,4-dihydropyrimidin-1(2H)-yl)tetrahydrofuran-2-yl)methyl phosphate (Compound I-34) was obtained in the same manner as in Reference Example 1.0 using commercially available 6-methylpyrimidine-2,4(1H,3H)-dione.

$^1$H-NMR (D$_2$O, 300 MHz) δ: 5.63 (s, 1H), 5.56 (d, J=2.9 Hz, 1H), 4.31 (t, J=6.6 Hz, 1H), 4.05-3.90 (m, 4H), 2.27 (s, 3H), 1.95 (s, 1H).

ESI-MS (m/z): 337 (M−1)

REFERENCE EXAMPLE 30.1

Compound am-30

(2R,3R,4R,5R)-2-((Bis(4-methoxyphenyl)(phenyl)methoxy)methyl)-4-((tert-butyldimethylsilyl)oxy)-5-(6-methyl-2,4-dioxo-3,4-dihydropyrimidin-1(2H)-yl)tetrahydrofuran-3-yl (2-cyanoethyl) diisopropylphosphoramidite (Compound am-30) was obtained in the same manner as in Reference Example 1.1 using commercially available 6-methylpyrimidine-2,4(1H,3H)-dione.

$^1$H-NMR (CDCl$_3$, 500 MHz) δ: 7.80 (m, 1H), 7.48-6.78 (m, 13H), 5.55 (s, 1H), 5.50 (m, 1H), 5.10 (m, 1H), 4.31-4.18 (m, 2H), 3.93-3.22 (m, 12H), 2.66-2.28 (m, 5H), 1.18-1.05 (m, 12H), 0.87 (0.86) (s, 9H), 0.07 (0.06) (s, 3H), 0.00 (−0.01) (s, 3H).

EXAMPLE 36

An siRNA (referred to as 6-Me-dU) having Compound I-34 as X at the 5' end of the antisense strand of 454-Xu shown in Table 24 below was synthesized in the same manner as in Example 1 using Compound am-30 obtained in Reference Example 30.1.

MALDI-TOF/MS (antisense strand): theoretical value: 6680.87 (M-H), actual value: 6681.08

REFERENCE EXAMPLE 31.0

Compound I-35

Step 1
(2R,3R,4R,5R)-2-(Benzoyloxymethyl)-5-(7-chloro-6-nitro-2,4-dioxo-3,4-dihydroquinazolin-1(2H)-yl)tetrahydrofuran-3,4-diyl dibenzoate (0.292 g, 34%) was obtained in the same manner as in Step 1 of Reference Example 1.0 using 7-chloro-6-nitroquinazoline-2,4(1H,3H)-dione (0.626 g, 1.24 mmol) synthesized according to the method described in the known method (Organic Process Research & Development, 2001, vol. 5, pp. 426-433).
ESI-MS (m/z): 684 (M−1)
Step 2
7-Chloro-1-(2R,3R,4S,5R)-3,4-dihydroxy-5-(hydroxymethyl)tetra hydrofuran-2-yl)-6-nitroquinazoline 2,4(1H,3H)-dione (1.26 g, 77%) was obtained in the same manner as in Step 2 of Reference Example 7.0 using (2R,3R,4R,5R)-2-(benzoyloxymethyl)-5-(7-chloro-6-nitro-2,4-dioxo-3,4-dihydroquinazolin-1 (2H)-yl)tetrahydrofuran-3,4-diyl dibenzoate (3.00 g, 4.37 mmol) obtained in Step 1.
ESI-MS (m/z): 372 (M−1)
Step 3
Di-tert-butyl ((3aR,4R,6R,6aR)-6-(7-chloro-6-nitro-2,4-dioxo-3,4-dihydroquinazolin-1(2H)-yl)-2,2-dimethyltetrahydrofuro[3,4-d][1,3]dioxol-4-yl)methyl phosphate was obtained in the same manner as in Steps 3 to 4 of Reference Example 7.0 using 7-chloro-1-(2R,3R,4S,5R)-3,4-dihydroxy-5-(hydroxymethyl)tetrahydrofuran-2-yl)-6-nitroquinazoline-2,4(1H,3H)-dione obtained in Step 2.
ESI-MS (m/z): 604 (M−1)
Step 4
((2R,3S,4R,5R)-5-(7-Chloro-6-nitro-2,4-dioxo-3,4-dihydroquinazolin-1(2H)-yl)-3,4-dihydroxytetrahydrofuran-2-yl)methyl phosphate (Compound I-35) triethylammonium salt (20.0 mg, 67%) was obtained in the same manner as in Step 5 of Reference Example 1.0 using di-tert-butyl ((3aR,4R,6R,6aR)-6-(7-chloro-6-nitro-2,4-dioxo-3,4-dihydroquinazolin-1(2H)-yl)-2,2-dimethyltetrahydrofuro[3,4-d][1,3]dioxol-4-yl)methyl phosphate (32.5 mg, 0.054 mmol) obtained in Step 3.

$^1$H-NMR (D$_2$, 300 MHz) δ: 8.67 (s, 1H), 7.87 (s, 1H), 6.08 (d, J=4.8 Hz, 1H), 4.77 (dd, J=6.6, 4.8 Hz, 1H), 4.42 (t, J=6.4 Hz, 1H), 4.08-3.99 (m, 4H), 3.09 (q, J=7.3 Hz, 6H), 1.17 (t, J=7.3 Hz, 9H).
ESI-MS (m/z): 452 (M−1)

REFERENCE EXAMPLE 31.1

Compound am-31

Step 2
7-Chloro-1-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-nitroquinazoline)-2,4(1H,3H)-dione is obtained in the same manner as in Steps 1 to 2 of Reference Example 1.1 using 7-chloro-1-(2R,3R,4S,5R)-3,4-dihydroxy-5-(hydroxymethyl)tetrahydrofuran-2-yl)-6-nitroquinazoline-2,4(1H,3H)-dione obtained in Step 2 of Reference Example 31.0.
Step 2
((2R,3R,4R,5R)-2-((Bis(4-methoxyphenyl)(phenyl)methoxy)methyl-4-((tert-butyldimethylsilyl)oxy)-5-(7-chloro-6-nitro-2,4-dioxo-3,4-dihydroquinazolin-1(2H)-yl)tetrahydrofuran-3-yl(2-cyanoethyl) diisopropylphosphoramidite (compound am-31) is obtained in the same manner as in Steps 3 to 5 of Reference Example 1.1 using 7-chloro-1-((4aR,6R,7R,7aR)-2,2-di-tert-butyl-7-((tert-butyldimethylsilyl)oxy)tetrahydro-4H-furo[3,2-d][1,3,2]dioxasilin-6-yl)-6-nitroquinazoline)-2,4(1H,3H)-dione obtained in Step 1 of Reference Example 31.1.

EXAMPLE 37

An siRNA having Compound I-35 at the 5' end of the antisense strand is synthesized in the same manner as in Example 1 using Compound am-31 obtained in Reference Example 31.1.

REFERENCE EXAMPLE 32.0

Compound I-36

Step 1
Di-tert-butyl ((3aR,4R,6R,6aR)-6-(7-chloro-6-nitro-2,4-dioxo-3,4-dihydroquinazolin-1(2H)-yl)-2,2-dimethyltetrahydrofuro[3,4-d][1,3]dioxol-4-yl)methyl phosphate (20.0 mg, 0.033 mmol) obtained in Step 3 of Reference Example 10.0 was dissolved in THF (1 mL), and a dimethylamine/THF solution (1 mL, 2.00 mol) was added thereto, and the mixture was stirred at room temperature for 30 minutes. After the solvent was evaporated under reduced pressure, the residue was purified by preparative thin-layer chromatography (heptane/ethyl acetate a 25/75) to obtain di-tert-butyl ((3aR,4R,6R,6aR)-6-(7-(dimethylamino)-6-nitro-2,4-dioxo-3,4-dihydroquinaxolin-1 (2H)-yl)-2,2-dimethyltetrahydrofuro[3,4-d][1,3]diox ol-4-yl)methyl (14.4 mg, 71%).
ESI-MS (m/z): 513 (M−1)
Step 2
((2R,3S,4R,5R)-5-(7-(Dimethylamino)-6-nitro-2,4-dioxo-3,4-dihydroquinazolin-1(2H)-yl)-3,4-dihydroxytetrahydrofuran-2-yl)methyl phosphate (Compound I-36) triethylammonium salt (12.5 mg, 62%) was obtained in the same manner as in Step 5 of Reference Example 1.0 using di-tert-butyl ((3aR,4R,6R,6aR)-6-(7-(dimethylamino)-6-nitro-2,4-dioxo-3,4-dihydroquinazolin-1(2H)-yl)-2,2-dimethyltetrahydrofuro[3,4-d][1,3]dioxol-4-yl)methyl (22.0 mg, 0.036 mmol) obtained in Step 1.

ESI-MS (m/z): 461 (M−1)

$^1$H-NMR (D$_2$O, 300 MHz) δ: 8.46 (s, 1H), 6.75 (s, 1H), 6.05 (d, J=4.4 Hz, 1H), 4.79 (dd, J=6.6, 4.0 Hz, 1H), 4.38 (t, J=7.0 Hz, 1H), 4.11-3.98 (m, 4H), 3.09 (q, J=7.3 Hz, 6H), 2.92 (s, 6H), 1.17 (t, J=7.3 Hz, 9H).

REFERENCE EXAMPLE 32.1

Compound am-33

Step 1

1-((4aR,6R,7R,7aR)-2,2-Di-tert-butyl-7-((tert-butyldimethylsilyl)oxy)tetrahydro-4H-furo[3,2-d][1,3,2]dioxasilin-6-yl)-7-(dimethylamino)-6-nitroquinazoline)-2,4(1H,3)-dione is obtained in the same manner as in Step 1 of Reference Example 32.0 using 7-chloro-1-((4aR,6R,7R,7aR)-2,2-di-tert-butyl-7-((tert-butyldimethylsilyl)oxy)tetrahydro-4H-furo[3,2-d][1,3,2]dioxasilin-6-nitroquinazoline)-2,4(1H, 3H)-dione obtained in Step 1 of Reference Example 31.1.

Step 2

((2R,3R,4R,5R)-2-((Bis(4-methoxyphenyl)(phenyl)methoxy)methyl-4-((tert-butyldimethylsilyloxy)-5-(7-(dimethylamino)-6-nitro-2,4-dioxo-3,4-dihydroquinazolin-1(2H)-yl)tetrahydrofuran-3-yl) (2-cyanoethyl) diisopropylphosphoramidite (Compound am-32) is obtained in the same manner as in Steps 3 to 5 of Reference Example 1.1 using 1-((4aR,6R,7R,7aR)-2,2-di-tert-butyl-7-((tert-butyldimethylsilyl)oxy)tetrahydro-4H-furo[3,2-d][1,3,2]dioxasilin-6-yl)-7-(dimethylamino)-6-nitroquinazoline)-2,4(1H, 3H)-dione obtained in Step 1.

EXAMPLE 38

An siRNA having Compound I-36 at the 5' end of the antisense strand is synthesized in the same manner as in Example 1 using Compound am-32 obtained in Reference Example 32.1.

REFERENCE EXAMPLE 33.0

Compound I-37

Step 1

1-(2R,3R,4S,5R)-3,4-Dihydroxy-5-(hydroxymethyl)tetrahydrofuran-2-yl)-7-(methylamino)-6-nitroquinazoline 2,4(1H,3H)-dione (110 mg, 71%) was obtained in the same manner as in Step 2 of Reference Example 1.0 using (2R,3R,4R,5R)-2-(benzoyloxymethyl)-5-(7-chloro-6-nitro-2,4-dioxo-3,4-dihydroquinazolin-1(2H)-yl)tetrahydrofuran-3,4-diyl dibenzoate (292 mg, 0.426 mmol) obtained in Step 1 of Reference Example 31.0.

ESI-MS (m/z): 367 (M−1)

Step 2

((2R,3R,4R,5R)-3,4-Dihydroxy-5-(7-(methylamino)-6-nitro-2,4-dioxo-3,4-dihydroquinazolin 1 (2H)-yl)tetrahydrofuran-2-yl)methyl phosphate (Compound I-37) triethylammonium salt was obtained in the same manner as in Steps 3 to 5 of Reference Example 1.0 using 1-(2R,3R,4S,5R)-3,4-dihydroxy-5-(hydroxymethyl)tetrahydrofuran-2-yl)-7-(methylamino)-6-nitroquinazoline-2,4(1H,3H)-dione obtained in Step 1.

ESI-MS (m/z): 447 (M−1)

$^1$H-NMR (D$_2$O, 300 MHz) δ: 8.67 (s, 1H), 6.48 (s, 1H), 6.02 (d, J=4.0 Hz, 1H), 4.78 (dd, J=6.6, 4.0 Hz, 1H), 4.37 (t, J=7.0 Hz, 1H), 4.12 (dt, J=13.9, 5.6 Hz, 1H), 4.03-3.97 (m, 2H), 2.97 (s, 3H) (Amine and amide protons are not observed.).

REFERENCE EXAMPLE 33.1

Compound am-33

(2R,3R,4R,5R)-2-((Bis(4-methoxyphenyl)(phenyl)methoxy)methyl)-4-((tert-butyldimethylsilyl)oxy)-5-(7-(methylamino)-6-nitro-2,4-dioxo-3,4-dihydroquinazolin-1(2H)-yl)tetrahydrofuran-3-yl) (2-cyanoethyl) diisopropylphosphoramidite (Compound am-33) was obtained in the same manner as in Reference Example 1.1 using 1-(2R,3R,4S,5R)-3,4-dihydroxy-5-(hydroxymethyl)tetrahydrofuran-2-yl)-7-(methylamino)-6-nitroquinazoline-2,4(1H,3H)-dione obtained in Step 1 of Reference Example 33.0.

$^1$H-NMR (CDCl$_3$, 500 MHz) δ: 9.03 (s, 1H), 8.40 (m, 1H), 7.88 (m, 1H), 7.48-6.73 (m, 13H), 6.64 (m, 1H), 5.88 (m, 1H), 5.13 (5.16) (m, 1H), 4.50-4.29 (m, 2H), 3.93-3.25 (m, 12H), 3.00 (2.96) (d, J=5.1 Hz, 3H), 2.60 (2.32) (m, 2H), 1.20-1.05 (m, 12H), 0.85 (0.82) (s, 9H), 0.07 (0.05) (s, 3H), −0.05 (−0.06) (s, 3H).

EXAMPLE 39

An siRNA (referred to as 6-NO2,7-Me-dQu) having Compound I-37 as X at the 5' end of the antisense strand of 454-Xu shown in Table 24 below was synthesized in the same manner as in Example 1 using Compound am-33 obtained in Reference Example 33.1.

MALDI-TOF/MS (antisense strand): theoretical value: 6790.94 (M−H), actual value: 6794.76

REFERENCE EXAMPLE 34.0

Compound I-38

Step 1

((3aR,4R,6R,6aR)-6-(6-(3-Chlorostyryl)-9H-purin-9-yl)-2,2-dimethyltetrahydrofuro[3,4-d][1,3]dioxol-4-yl)methanol (118 mg, 90%) was obtained in the same manner as in Step 2 of Reference Example 6.0 using ((3aR,4R,6R,6aR)-6-(6-chloro-9H-purin-9-yl)-2,2-dimethyltetrahydrofuro[3,4-d][1,3]dioxo-4-yl)methanol (100 mg, 0.306 mmol) obtained in Step 1 of Reference Example 6.0 and (E)-2-(3-chlorostyryl)-4,4,5,5-tetramethyl-dioxaborolane 1,3,2-(81.0 mg, 0.306 mmol).

ESI-MS (m/z): 429 (M+1)

Step 2

Di-tert-butyl ((3aR,4R,6R,6aR)-6-(6-(3-chlorostyryl)-9H-purin-9-yl)-2,2-dimethyltetrahydrofuro[3,4-d][1,3]dioxol-4-yl)methyl phosphate (107 mg, 59.8%) was obtained in the same manner as in Step 3 of Reference Example 6.0 using ((3aR,4R6R,6aR)-6-(6-(3-chlorostyryl)-9H-purin-9-yl)-2,2-dimethyltetrahydrofuro[3,4-d][1,3]dioxol-4-yl)methanol (115 mg, 0.268 mmol) obtained in Step 1.

ESI-MS (m/z): 621 (M+1)

Step 3

((2R,3S,4R,5R)-5-(6-(3-Chlorostyryl)-9H-purin-9-yl)-3,4-dihydroxytetrahydrofuran-2-yl)methyl phosphate (Compound I-38) triethylammonium salt (28.0 mg, 25.4%) was obtained in the same manner as in Step 5 of Reference Example 1.0 using di-tert-butyl ((3aR,4R,6R,6aR)-6-(6-(3- chlorostyryl)-9H-purin-9-yl)-2,2-dimethyltetrahydrofuro[3,4-d][1,3]dioxol-4-yl)methyl phosphate (120 mg, 0.193 mmol) obtained in Step 2.

$^{1}$H-NMR (D$_{2}$O, 400 MHz) δ: 8.45 (1H, s), 8.34 (1H, sa), 7.32-7.20 (1H, m), 6.86-6.70 (3H, m), 6.64-6.50 (2H, m), 5.92-5.85 (1H, m), 4.60-4.54 (1H, m), 4.38-4.32 (1H, m), 4.28-4.20 (1H, m), 4.10-3.92 (2H, m), 3.04 (6H, q, J=7.5 Hz), 1.11 (9H, t, J=127.8 Hz).

ESI-MS (m/z): 469 (M+1)

REFERENCE EXAMPLE 34.1

Compound am-34

Step 1

6-(3-Chlorostyryl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine is obtained in the same manner as in Step 1 of Reference Example 22.0 using 6-chloro-9-((4aR,6R,7R,7aS)-2,2-di-tert-butyl-7-(tert-butyldimethylsilyloxy)tetrahydro-4H-furo[3,2-d][1,3,2]dioxasilin-6-yl)-9H-purine obtained in Step 2 of Reference Example 17.1.

Steps 2 to 4

(2R,3R,4R,5R)-2-((Bis(4-methoxyphenyl)(phenyl)methoxy)methyl)-4-(tert-butyldimethylsilyloxy)-5-(6-(3-chlorostyryl)-9H-purin-9-yl)tetrahydrofuran-3-yl 2-cyanoethyl diisopropylphosphoramidite (Compound am-34) is obtained in the same manner as in Steps 3 to 5 of Reference Example 1.1 using 6-(3-chlorostyryl)-9-((4aR,6R,7R,7aR)-2,2-di-tert-butyl-7-(tert-butyldimethylsilyloxy)tetrahydro-4H-furo[3,2-d][1,3,2]dioxasilin-6-yl)-9H-purine obtained in Step 1.

EXAMPLE 40

An siRNA having Compound I-38 at the 5' end of the antisense strand is synthesized in the same manner as in Example 1 using Compound am-34 obtained in Reference Example 34.1.

TEST EXAMPLE 6

The affinity of the luciferase-targeting siRNAs introduced an unnatural nucleotide residue at the 5' end of the antisense strand obtained in Examples 1 to 4 for AGO2 was evaluated by measuring the competition with the 5' end of an oligo DNA immobilized on the surface of a substrate which immobilizes the affinity of the siRNA and an AGO2-MID domain using Biacore T100 and T200 systems (GE Healthcare Sciences (GE) Company) as described below.

(1) Preparation of Sample

A running buffer stock solution (HBS-EP+ 10×, GE Company, BR-1006-69) was diluted to 10-fold with pure water, followed by filtration through a filter, and then HPS-EP+ (10 mM HEPES (4-(2-hydroxyethyl)-1-piperazineethanesulfonic acid), 150 mM NaCl, 3 mM EDTA, 0.05% (v/v) Surfactant P20, pH 7.4) was prepared and used as a running buffer.

To HBS-EP+, dithiothreitol (DTT) was added to give a final concentration of 2 mM, and the siRNA solution was diluted to 200 nM, 100 nM, 50 nM, and 25 nM, and each of the diluted siRNA solutions was mixed with an equal amount of a 5 µg/mL AGO2-MID domain solution obtained by dilution in the same manner, whereby 2.5 µg/mL AGO2-MID domain solutions containing the siRNA at 100 nM, 50 nM, 25 nM, and 12.5 nM, respectively, were prepared.

(2) Measurement Method (2-1) Immobilization of Biotinylated Oligo

A biotinylated single-stranded DNA (dT(16)-Biotin) was immobilized on a chip (Series S Sensor Chip SA, GE Company, BR-1005-31). The flow rate was set to a constant rate of 10 µL/min, and the biotinylated single-stranded DNA solution diluted to 100 nM with HBS-EP+ was used to immobilize on Fc2 or Fc4 according to the following program. At the same time, a blank immobilization operation was performed on Fc1 and Fc3.

1. 1 M NaCl/50 mM NaOH, 60 seconds (INJECT command), 3 times
2. Running buffer (WASH command)
3. Running buffer 120 seconds (INJECT command)
4. Aim for Immobilized Level was set to 750 RU and immobilized (LIGAND INJECT command)
5. 1 M NaCl/50 mM NaOH/50% isopropyl alcohol (WASH command)

In the immobilized cells, an immobilization level of about 700 RU was confirmed.

(2-2) Competition Experiments on Oligonucleotide (siRNA)

A competition experiment by the siRNA was performed using the chip immobilized the biotinylated single-stranded DNA thereon. The flow rate is set to 30 µL/minute throughout the experiment, and one cycle is performed as follows: binding for 60 seconds, dissociation for 5 seconds, and regeneration 1 M NaCl for 5 seconds.

In order to stabilize the machine, the first 10 cycles are performed by adding only HBS-EP+, and thereafter, the measurement is performed for each siRNA in the order of HBS-EP+(BLANK), a 2.5 µg/mL AGO2-MID domain solution (CONTROL), and 2.5 µg/mL AGO2-MID domain solutions (Sample) containing the siRNA at 100 nM, 50 nM, 25 nM, and 12.5 nM, respectively. In the analysis, the binding level of the graph obtained by subtracting the graph for blank immobilization from the graph for the immobilized cell is used, and the residual binding ratio (%) is calculated according to the formula: ([Sample]−[BLANK])/([CONTROL]−[BLANK])×100, and the inhibition ratio (%) is calculated according to 100−(residual binding ratio).

Further, for comparison, siRNAs having a corresponding natural nucleotide at the 5' end of the antisense strand of each of the siRNAs were also tested in the same manner.

In Table 21, the respective inhibition ratios (%) are shown.

TABLE 21

| | inhibition rate (%) (50 nM AGO2-MID domain solutions) |
|---|---|
| 874-A | 21.33 |
| 874-8-Br-dA | 75.67 |
| 874-8-oxo-dA | 31.77 |
| 874-U | 38.94 |
| 874-5-Br-dU | 45.07 |
| 454-5-U | 60.59 |
| 454-5-F-dU | 66.67 |
| 1556-5-U | 51.43 |
| 1556-5-F-dU | 57.63 |

From the results of Test Example 6, it was revealed that the luciferase-targeting siRNAs (874-8-Br-dA, 874-8-oxo-dA, 874-5-Br-dU, 454-5-F-dU, and 1556-5-F-dU) introduced an unnatural nucleotide residue at the 5' end of the antisense strand obtained in Examples 1 to 4 have a higher inhibition ratio (%) than the siRNAs (874-A and 874-U) having adenosine monophosphate or uridine monophosphate, which is a corresponding natural nucleotide, at the 5' end thereof, and therefore have a higher affinity for AGO02.

TEST EXAMPLE 7

Biacore of Nucleotide (Monomer)

The affinity of 8-Br-dA (Compound I-1) and 5-fluoro-2'-deoxyuridine monophosphate (Compound I-4), which are unnatural nucleotides at the 5' end of the siRNAs obtained in Examples 1 and 4, respectively, for AGO2 was evaluated by measuring the affinity between each of the siRNAs and an AGO2-MID domain with respect to competition with the 5' end of an oligo DNA immobilized on the surface of a substrate which immobilizes the affinity of the siRNA and an AGO2-MID domain using Biacore T100 and T200 systems (GE Company) as described below.

(1) Preparation of Sample

HBS-EP+10× was diluted to 10-fold with pure water, and DTT was added thereto to give a final concentration of 2 mM, followed by filtration through a filter to prepare an HBS-EP+ 2 mM DTT aqueous solution. To this solution, dimethyl sulfoxide (DMSO) was added to give a final concentration of 1%, whereby a running buffer was prepared.

A monomer solution dissolved in DMSO or distilled water was diluted to 200 µM, 40 µM, 8 µM, and 1.6 µM/(2% DMSO, HES-EP+, 2 mM DTT), and each of the diluted solutions was mixed with an equal amount of a 5 µg/mL AGO2-MID domain solution diluted with the HBS-EP+ 2 mM DTT solution, whereby 2.5 µg/mL AGO2-MID domain solutions containing the monomer at 100 µM, 20 µM, 4 µM, and 0.8 µM, respectively, were prepared as the HBS-EP+, 2 mM DTT, 1% DMSO solution.

(2) Competition Experiment on Nucleotide (Monomer)

A competition experiment by the siRNA was performed using a chip immobilized dT(16)-Biotin oligo thereon in the same manner as in Test Example 6. The flow rate is set to 30 µL/minute throughout the experiment, and one cycle is performed as follows: binding for 60 seconds, dissociation for 5 seconds, and regeneration 1 M NaCl for 5 seconds.

In order to stabilize the machine, the first 10 cycles are performed by adding only HBS-EP+, and thereafter, the measurement is performed for each monomer in the order of HBS-EP+ (BLANK), a 2.5 µg/mL AGO2-MID domain solution (CONTROL), and 2.5 µg/mL AGO2-MID domain solutions (Sample) containing the monomer at 100 µM, 20 µM, 4 µM, and 0.8 µM, respectively, and a 2.5 µg/mL AGO2-MID domain solution (CONTROL).

In the analysis, the binding level of the graph obtained by subtracting the graph for blank immobilization from the graph for the immobilized cell is used, and the residual binding ratio (%) is calculated according to ([Sample]−[BLANK])/((CONTROL)−(BLANK))×100, and the inhibition ratio (%) is calculated according to 100−(residual binding ratio).

In Table 22, the inhibition ratios (%) of 8-Br-dA (Compound I-1) and 5-fluoro-2'-deoxyuridine monophosphate (Compound I-4), and for comparison thereof, the inhibition ratios (%) of adenosine monophosphate (AMP) and uridine monophosphate (UMP) are shown.

TABLE 22

| | inhibition rate (%) (100 µM AGO2-MID domain solutions) |
|---|---|
| compound I-1 | 68.6 |
| compound I-4 | 42.7 |
| AMP | 27.1 |
| UMP | 35.9 |

From the results of Test Example 7, it was revealed that 8-Br-dA and 5-fluoro-2'-deoxyuridine monophosphate, which are unnatural nucleotides introduced at the 5' end of the antisense strands of the siRNAs of the present invention, have a higher inhibition ratio (%) than adenosine monophosphate or uridine monophosphate, which is a natural nucleotide, and therefore have a higher affinity for AGO2.

TEST EXAMPLE 8

Biacore of Monomer

The affinity of Compounds I-5 to I-31, and I-33 to I-38, which are unnatural nucleotides at the 5' end of the siRNAs obtained in Examples 7 to 33, and 35 to 40 for AGO2 wan evaluated in the same manner as in Test Example 7.

The respective inhibition ratios (%) determined are shown in Table 23.

TABLE 23

| | inhibition rate (%) (100 µM AGO2-MID domain solutions) |
|---|---|
| compound I-5 | 87.4 |
| compound I-6 | 70.0 |
| compound I-7 | 71.7 |
| compound I-8 | 77.1 |
| compound I-9 | 70.9 |
| compound I-10 | 73.5 |
| compound I-11 | 60.9 |
| compound I-12 | 74.2 |
| compound I-13 | 63.4 |
| compound I-14 | 63.3 |
| compound I-15 | 73.0 |
| compound I-16 | 65.6 |
| compound I-17 | 86.0 |
| compound I-18 | 94.8 |
| compound I-19 | 89.7 |
| compound I-20 | 76.9 |
| compound I-21 | 78.2 |
| compound I-22 | 91.6 |
| compound I-23 | 85.2 |
| compound I-24 | 88.4 |
| compound I-25 | 33.9 |
| compound I-26 | 82.4 |
| compound I-27 | 92.4 |
| compound I-28 | 77.0 |
| compound I-29 | 77.9 |
| compound I-30 | 73.2 |
| compound I-31 | 73.6 |
| compound I-33 | 82.9 |
| compound I-34 | 31.8 |
| compound I-35 | 88.0 |
| compound I-36 | 91.6 |
| compound I-37 | 92.3 |
| compound I-38 | 78.9 |

From the results of Test Example 8, it was revealed that all Compounds I-5 to I-31, and I-33 to I-38, which are unnatural nucleotides at the 5' end of the siRNAs obtained in Examples 7 to 33, and 35 to 40 have a high inhibition ratio (%), and therefore have a high affinity for AGO2. Accordingly, the siRNAs obtained in Examples 7 to 33, and 35 to 40 are oligonucleotides having an improved affinity for AGO2, and therefore are expected to be oligonucleotides having a high knockdown activity against a target mRNA.

TEST EXAMPLE 9

Knockdown Activity of Luciferase-Targeting siRNA

The activity of an siRNA having each compound at the 5' end of the antisense strand obtained in Example 39, 23, 36, or 27 was measured and evaluated in the same manner as in Test Example 1 except that the number of cells per well was set to 7500, the final concentration of the siRNA was set to the following five levels: 10000 pmol/L, 1000 pmol/L, 100 pmol/L, 10 pmol/L, and 1 pmol/L, and N was set to 5. The knockdown activity of each of siRNAs having I-37 (6-NO2, 7-Me-dQu), I-21 (6-napht-2-yl-dPu), I-34 (6-Me-dU), or I-25 (6-napht-1-yl-dPu) at the 5' end of the antisense strand is shown in FIG. 4.

Incidentally, an siRNA having 8-Br-dA as X at the 5' end of the antisense strand of 454-Xa in Table 24 (referred to as 454-BrdA) was synthesized in the same manner as in Example 1 using 8-Br-dA, and the activity of the siRNA was measured and evaluated. Further, also for an siRNA having a natural nucleotide which contains adenosine monophosphate or uridine monophosphate, at the 5' end of the antisense strand (referred to as 454-A or 454-U), the activity of the siRNA was measured and evaluated in the same manner.

From the results of Test Example 9, it is found that the siRNA having a high affinity base analog for Ago2 at the 5' end of the antisense strand shows a higher knockdown activity than the siRNA having a natural nucleotide at the 5' end of the antisense strand.

TEST EXAMPLE 10

Knockdown Activity of Luciferase-Targeting siRNA

The activity of an siRNA having each compound at the 5' end of the antisense strand obtained in Example 34 and 21 was measured and evaluated in the same manner as in Test Example 1 except that the number of cells per well was set to 7500, the final concentration of the siRNA was set to the following five levels: 10000 pmol/L, 1000 pmol/L, 100 pmol/L, 10 pmol/L, and 1 pmol/L, and N was set to 5. The knockdown activity of siRNAs having I-32 (2'-OMe-6-styryl-dA) or I-19 (di-Me-thienyl-dU) at the 5' end of the antisense strand is shown in FIG. 5.

From the results of Test Example 10, it is found that the siRNA having a high affinity base analog for Ago2 at the 5' end of the antisense strand shows a higher knockdown activity than the siRNA having a corresponding natural nucleotide at the 5' end of the antisense strand.

TABLE 24

| | sense strand | | antisense strand | |
|---|---|---|---|---|
| | sequence (5'→3') | sequence number | sequence (5'→3') | sequence number |
| 454-U | GGAUAGCAAGACCGACUAACA | 25 | UUAGUCGGUCUUGCUAUCCAU | 28 |
| 454-A | GGAUAGCAAGACCGACUAUCA | 65 | AUAGUCGGUCUUGCUAUCCAU | 66 |
| 454-Xu | GGAUAGCAAGACCGACUAACA | 25 | XUAGUCGGUCUUGCUAUCCAU | 26 |
| 454-Xa | GGAUAGCAAGACCGACUAUCA | 65 | XUAGUCGGUCUUGCUAUCCAU | 26 |

From the results of the above Test Examples 9 and 10, by applying the siRNA having an improved activity according to the present invention to pharmaceuticals, the dose can be expected to be reduced as compared with the case where a natural siRNA is used.

INDUSTRIAL APPLICABILITY

According to the present invention, an oligonucleotide having an improved affinity for AGO2 and the like are provided.
[Sequence Listing]
1000P12280 Sequence Listing.txt

The invention claimed is:

1. An oligonucleotide, comprising a nucleotide residue or a nucleoside residue represented by formula (I) at the 5' end thereof, wherein the nucleotide residue or the nucleoside residue binds to an adjacent nucleotide residue through the oxygen atom at position 3 :

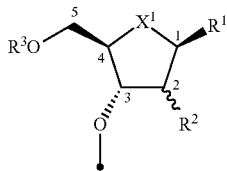

(I)

wherein $X^1$ is an oxygen atom or a sulfur atom,
$R^1$ is formula (II):

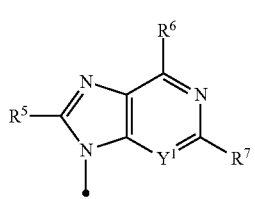

(II)

wherein $Y^1$ is a nitrogen atom,
$R^5$ is a hydrogen atom, halogen, cyano, unsubstituted or substituted lower alkyl, unsubstituted or substituted lower alkenyl, unsubstituted or substituted lower alkynyl, unsubstituted or substituted lower alkoxy, unsubstituted or substituted lower alkylthio, unsubstituted or substituted aryl, an unsubstituted or substituted aromatic heterocyclic group, or —$NR^{10a}R^{10b}$ wherein $R^{10a}$ and $R^{10b}$ may be the same or different, and each is a hydrogen atom or unsubstituted or substituted lower alkyl, $R^6$ is a hydrogen atom, halogen, cyano, unsubstituted or substituted lower alkyl, unsubstituted or substituted lower alkenyl, unsubstituted or substituted lower alkynyl, unsubstituted or substituted lower alkoxy, unsubstituted or substituted lower alkylthio, unsubstituted or substituted lower alkanoyl, unsubstituted or substituted aryl, unsubstituted or substituted aralkyl, unsubstituted or substituted aryloxy, unsubstituted or substituted arylthio, unsubstituted or substituted aroyl, an unsubstituted or substituted aromatic heterocyclic group, unsubstituted or substituted aromatic heterocyclic alkyl, unsubstituted or substituted aromatic heterocyclicoxy, unsubstituted or substituted aromatic heterocyclicthio, unsubstituted or substituted aromatic heterocyclic carbonyl, or —$NR^{11a}R^{11b}$ wherein $R^{11a}$ and $R^{11b}$ may be the same or different, and each is a hydrogen atom, unsubstituted or substituted lower alkyl, unsubstituted or substituted lower alkenyl, unsubstituted or substituted lower alkynyl, unsubstituted or substituted aryl, unsubstituted or substituted aralkyl, unsubstituted or substituted aromatic heterocyclic alkyl, unsubstituted or substituted lower alkanoyl, unsubstituted or substituted lower alkylsulfonyl, unsubstituted or substituted aroyl, unsubstituted or substituted arylsulfonyl, an unsubstituted or substituted aromatic heterocyclic group, unsubstituted or substituted aromatic heterocyclic carbonyl, or unsubstituted or substituted aromatic heterocyclic sulfonyl, $R^7$ is a hydrogen atom, or
$R^1$ is formula (III):

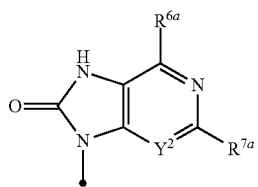

(III)

wherein $Y^2$ is a nitrogen atom, $R^{6a}$ is an amino group and $R^{7a}$ is a hydrogen atom, or $R^1$ is formula (IV):

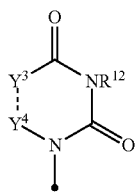

(IV)

wherein $R^{12}$ is a hydrogen atom,
--- is a double bond,
$Y^3$ is $CR^{14e}$ wherein $R^{14e}$ is a hydrogen atom, cyano, unsubstituted or substituted lower alkyl, unsubstituted or substituted lower alkenyl, or unsubstituted or substituted lower alkynyl and
$Y^4$ is $CR^{14f}$ wherein $R^{14f}$ is a hydrogen atom, halogen, cyano, unsubstituted or substituted lower alkyl, unsubstituted or substituted lower alkenyl, unsubstituted or substituted lower alkynyl, unsubstituted or substituted aryl, unsubstituted or substituted aralkyl, an unsubstituted or substituted aromatic heterocyclic group, or unsubstituted or substituted aromatic heterocyclic alkyl, or
$R^1$ is formula (V):

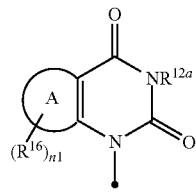

(V)

wherein $R^{12a}$ is a hydrogen atom, ring A is an aromatic ring or a heteroaromatic ring, n1 is an integer of 0 to 4, $R^{16}$ is halogen, hydroxy, sulfanyl, nitro, cyano, unsubstituted or substituted lower alkyl, unsubstituted or substituted lower alkenyl, unsubstituted or substituted lower alkynyl, unsubstituted or substituted lower alkoxy, unsubstituted or substituted lower alkylamino, unsubstituted or substituted di-lower alkylamino, provided that when n1 is an integer of 2 to 4, the respective $R^{16}$'s may be the same or different, with the proviso that when ring A is a benzene ring and n1 is 2, $R^{16}$'s are not lower alkoxy,
$R^2$ is a hydrogen atom, hydroxy, halogen, or unsubstituted or substituted lower alkoxy, and
$R^3$ is a hydrogen atom or

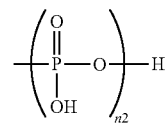

wherein n2 is 1.

2. The oligonucleotide according to claim 1, wherein $X^1$ is an oxygen atom.

3. The oligonucleotide according to claim 1, wherein $R^1$ is formula (II).

4. The oligonucleotide according to claim 1, wherein $R^1$ is formula (III).

5. The oligonucleotide according to claim 1, wherein $R^1$ is formula (IV).

6. The oligonucleotide according to claim 1, wherein $R^1$ is formula (V).

7. The oligonucleotide according to claim 6, wherein ring A is formula (A1):

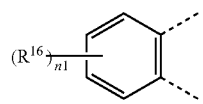

(A1)

provided that the case where ring A is represented by formula (A1'):

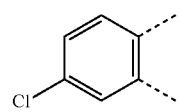

(A1')

is excluded, formula (A2):

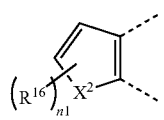

(A2)

wherein n1 is an integer of 0 to 2, and $X^2$ is NH, an oxygen atom, or a sulfur atom, or formula (A3):

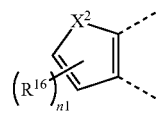

(A3)

wherein n1 is an integer of 0 to 2.

8. The oligonucleotide according to claim 1, wherein $R^3$ is.

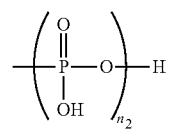
5
9. The oligonucleotide according to claim 1, wherein $R^2$ is a hydrogen atom, hydroxy, a fluorine atom, or methoxy.
10. The oligonucleotide according to claim 1, wherein the oligonucleotide has a length of 10 to 80 bases.
\* \* \* \* \*